United States Patent
Rangaramanujam et al.

(10) Patent No.: US 10,918,720 B2
(45) Date of Patent: Feb. 16, 2021

(54) SELECTIVE DENDRIMER DELIVERY TO BRAIN TUMORS

(71) Applicant: The Johns Hopkins University, Baltimore, MD (US)

(72) Inventors: Kannan Rangaramanujam, Highland, MD (US); Betty M. Tyler, Baltimore, MD (US); Fan Zhang, Baltimore, MD (US); Panagiotis Mastorakos, Charlottesville, VA (US); Manoj K. Mishra, Ellicott City, MD (US); Antonella Mangraviti, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/502,739

(22) PCT Filed: Aug. 13, 2015

(86) PCT No.: PCT/US2015/045104
§ 371 (c)(1),
(2) Date: Feb. 8, 2017

(87) PCT Pub. No.: WO2016/025741
PCT Pub. Date: Feb. 18, 2016

(65) Prior Publication Data
US 2017/0173172 A1    Jun. 22, 2017

Related U.S. Application Data

(60) Provisional application No. 62/036,675, filed on Aug. 13, 2014, provisional application No. 62/036,839, (Continued)

(51) Int. Cl.
*A61K 9/00* (2006.01)
*A61K 45/06* (2006.01)
(Continued)

(52) U.S. Cl.
CPC .......... *A61K 45/06* (2013.01); *A61K 31/4439* (2013.01); *A61K 31/551* (2013.01);
(Continued)

(58) Field of Classification Search
CPC ...................................... A61K 45/06
See application file for complete search history.

(56) References Cited

U.S. PATENT DOCUMENTS

| 4,507,466 A | 3/1985 | Tomalia |
| 4,558,120 A | 12/1985 | Tomalia |

(Continued)

FOREIGN PATENT DOCUMENTS

| CA | 2777682 | 5/2011 |
| EP | 1639029 | 7/2007 |

(Continued)

OTHER PUBLICATIONS

Sk, Comparative study of microtubule inhibitors—Estramustine and natural podophyllotoxin conjugated PAMAM dendrimer on glioma cell proliferation, European Journal of Medicinal Chemistry, 2013, 68, 47-57.*

(Continued)

*Primary Examiner* — Paul W Dickinson
(74) *Attorney, Agent, or Firm* — Pabst Patent Group LLP

(57) ABSTRACT

A composition comprising poly(amidoamine) (PAMAM) hydroxyl-terminated dendrimers covalently linked to at least one therapeutic, prophylactic or diagnostic agent for the treatment or alleviation of one or more symptoms of a brain tumor have been developed. The dendrimers comprise one or more ethylene diamine-core poly(amidoamine) (PAMAM) hydroxyl-terminated generation-4, 5, 6, 7, 8, 9, or 10, most preferably generation 6 (G4-10-OH) dendrimers. The G6 dendrimers have demonstrated unexpectedly high uptake into the brain. The dendrimers provide a means for selective (Continued)

delivery through the blood brain barrier ("BBB") of chemotherapeutic, immunotherapeutic and palliative agents. The dendrimers also have the advantage that two different classes of compounds, having one or more mechanisms of action can be bound to the dendrimers, providing simultaneous delivery. The dendrimers may be administered alone by intravenous injection, or as part of a multi-prong therapy with radiation.

29 Claims, 6 Drawing Sheets

Specification includes a Sequence Listing.

Related U.S. Application Data filed on Aug. 13, 2014, provisional application No. 62/059,240, filed on Oct. 3, 2014.

(51) Int. Cl.
A61K 49/00 (2006.01)
A61K 31/4439 (2006.01)
A61K 47/59 (2017.01)
A61K 31/551 (2006.01)

(52) U.S. Cl.
CPC ........ A61K 47/595 (2017.08); A61K 49/0032 (2013.01); A61K 49/0054 (2013.01)

(56) References Cited

U.S. PATENT DOCUMENTS

| | | | |
|---|---|---|---|
| 4,568,737 | A | 2/1986 | Tomalia |
| 4,587,329 | A | 5/1986 | Tomalia |
| 5,714,166 | A | 2/1998 | Tomalia |
| 5,968,979 | A | 10/1999 | Brusilow |
| 8,148,356 | B2 | 4/2012 | Pavliv |
| 8,399,445 | B2 | 3/2013 | Pavliv |
| 8,404,215 | B1 | 3/2013 | Scharschmidt |
| 8,427,225 | B2 | 4/2013 | Nakatake |
| 8,642,012 | B2 | 2/2014 | Scharschmidt |
| 8,653,061 | B2 | 2/2014 | Pavliv |
| 8,722,738 | B2 | 5/2014 | Pavliv |
| 8,889,101 | B2 | 11/2014 | Kannan |
| 9,095,559 | B2 | 8/2015 | Scharschmidt |
| 2002/0068795 | A1 | 6/2002 | Won |
| 2002/0192843 | A1 | 12/2002 | Kaganove et al. |
| 2003/0135005 | A1 | 7/2003 | Houser et al. |
| 2003/0180250 | A1 | 9/2003 | Chauhan |
| 2004/0151754 | A1 | 8/2004 | Ashton |
| 2006/0041058 | A1 | 2/2006 | Yin |
| 2006/0204443 | A1 | 9/2006 | Kobayashi |
| 2006/0240110 | A1 | 10/2006 | Kick et al. |
| 2007/0088014 | A1 | 4/2007 | Edelman |
| 2007/0128681 | A1 | 6/2007 | Barman et al. |
| 2007/0298006 | A1 | 12/2007 | Tomalia et al. |
| 2008/0031848 | A1 | 2/2008 | Konradi |
| 2009/0104123 | A1 | 4/2009 | Yang |
| 2010/0160299 | A1 | 6/2010 | Baker, Jr. |
| 2011/0034422 | A1 | 2/2011 | Kannan |
| 2011/0189291 | A1 | 8/2011 | Yang |
| 2011/0189299 | A1 | 8/2011 | Okubo |
| 2012/0003155 | A1 | 1/2012 | Kannan |
| 2013/0123330 | A1 | 5/2013 | Lu |
| 2013/0136697 | A1 | 5/2013 | Kannan |
| 2015/0352230 | A1 | 12/2015 | Mullen et al. |
| 2017/0119899 | A1* | 5/2017 | Kannan ............ A61K 47/48215 |

FOREIGN PATENT DOCUMENTS

| | | | |
|---|---|---|---|
| WO | 0018394 | 4/2000 | |
| WO | WO 00/18394 | 4/2000 | |
| WO | 2003080121 | 10/2003 | |
| WO | WO 2003/080121 | 10/2003 | |
| WO | 2004041310 | 5/2004 | |
| WO | WO 2004/041310 | 5/2004 | |
| WO | 2004058272 | 7/2004 | |
| WO | 2005055926 | 11/2004 | |
| WO | 2004106411 | 12/2004 | |
| WO | WO 2004/106411 | 12/2004 | |
| WO | 2006033766 | 3/2006 | |
| WO | WO 2006/033766 | 3/2006 | |
| WO | 2006115547 | 11/2006 | |
| WO | 2007089607 | 8/2007 | |
| WO | WO 2007/089607 | 8/2007 | |
| WO | 2008068531 | 6/2008 | |
| WO | WO 2008/068531 | 6/2008 | |
| WO | 2009046446 | 4/2009 | |
| WO | WO 2009/046446 | 4/2009 | |
| WO | 2009142754 | 1/2010 | |
| WO | WO 2009142754 A4 * | 1/2010 | ....... A61K 47/48207 |
| WO | 2010017181 | 2/2010 | |
| WO | WO 2010/017184 | 2/2010 | |
| WO | 2010147831 | 12/2010 | |
| WO | WO 2010/147831 | 12/2010 | |
| WO | WO 2011/011384 | 1/2011 | |
| WO | WO 2011011384 A2 * | 1/2011 | ....... A61K 47/48107 |
| WO | 2011011384 | 7/2011 | |
| WO | 2011123591 | 10/2011 | |
| WO | WO 2011/123591 | 10/2011 | |
| WO | 2012037457 | 3/2012 | |
| WO | 2014109927 | 7/2014 | |
| WO | WO 2009/142754 | 11/2014 | |
| WO | WO 2014/178892 | 11/2014 | |
| WO | 2014197909 | 12/2014 | |
| WO | WO 2014/197909 | 12/2014 | |
| WO | 2015027068 | 2/2015 | |
| WO | WO 2015/027068 | 2/2015 | |
| WO | 2015038493 | 3/2015 | |
| WO | WO 2015/038493 | 3/2015 | |
| WO | 2015168347 | 11/2015 | |
| WO | WO 2015/168347 | 11/2015 | |
| WO | 2014178892 | 12/2015 | |
| WO | WO 2016/025745 | 2/2016 | |
| WO | 2016025745 | 4/2016 | |
| WO | 2017074993 | 5/2017 | |

OTHER PUBLICATIONS

Jain, Nanobiotechnology-Based Strategies for Crossing the Blood-Brain Barrier, Nanomedicine, 2012, 7(8), 1225-1233.*
Akaishi, et al., "Quantitative Analysis of Major Histocompatibility Complex Class 11—Positive Cells In Posterior Segment of Royal College of Surgeons Rat Eyes," Jpn. J. Ophthalmology, 42:357-62 (1998).
Akinc, et al., "Exploring polyethylenimine-mediaied DNA transfection and the proton sponge hypothesis", J Gene Med, . 7(5): 657-63 (2005).
Alexandre, et al., "Accumulation of hydrogen peroxide is an early and crucial step for paclitaxel-induced cancer cell death both in vitro and in vivo", Int. J. Cancer, 19:41-8 (2006).
Allard, et al., "Convection-enhanced delivery of nanocarriers for the treatment of brain tumors", Biomaterials, 30(12):2302-18 (2009).
Almutairi, et al., "Biodegradable dendritic position emittinf nanoprobes for the nominvasive Imaging of angiogenesis", PNAS, 106(3):685-90 (2009).
Almutairi, et al., "Monitoring the biodfgradation of dendritic nrear-infrared nanoprobes by in vivo fluorescence imaging", Mol Pharm., 5(6):1103-10 (2008).
Alving, et al., "Therapy of leishmaniasis: Superior efficacies of liposome-encapsulated drugs", PNAS, 75(6):2959-63 (1978).
Antoni, et al., "A chemoselective approach for the accelerated synthesis of well-defined dendritic architectures", Chem Commun (Camb), 22(22):2249-51 (2007).
Antoni,et al., "Bifunctional dendrimers: from robust synthesis and accelerated one-pot postfunctionalization strategy to potential applications", Angew Chem Int Ed Engl, 48(12):2126-30 (2009).
Arrick and Nathan, "Glutathione metabolism as a determinant of therapeutic efficacy: a review", Cancer Res., 44:d224-32 (1984).

(56) References Cited

OTHER PUBLICATIONS

Aslam, et al., "Antibacterial and antifungal activity of cicerfuran and related 2-arylbenz.ofurans and stilbenes", *Microbiol Res.*, 164:191-5 (2009).
Augustin, et al., "Effects of Allopurinol and Steroids on Inflammation and OxidativeTissue Damage in Experimental Lens Induced Uveitis: A Biochemical and Morphological Study," *Br. J. Ophthalmol.* 80(5):451-7 (1996).
Baek, et al., "Sybthesis and protein binding properties of T-antigen containing glycoPAMAM dendrimers", *Bioorganic Med Chem.*, 10(1):11-7 (2002).
Ballatori, "N-Acetyl cystelne as an antidote in methyl mercury poisoning", *EnViron. Health Perspect.*, 106 (5):267-71 (1998).
Balogh, et al., "Dendrimer-Silver Complexes and Nanocomposites as Antimicrobial Agents", *Nano Lett.*, 1:18-21 (2001).
Barrett, et al., "Dendrimers in medical nanotechnology", *Eng Med Biol Mag.*, 28(1):12-22 (2009).
Behl, et al., "Neuroprotection Against Oxidative Stress by Estrogens: Structure-Activity Relationship," *Mol. Pharmacol.* 51(4):535-41 (1997).
Bell , et al., "Effects of Intrauterine Inflammation on Developing Rat Brain," *J. Neurosci.Res.*, 70:570-9 (2002).
Bellair, et al., "Investigation of clay modifier effects on the structure and rheology of supercritical carbon dioxide processed polymer nanocomposites", *J. Polymer Sci Part B*, 48(8):823-31 (2010).
Beloosesky, et al., "Maternal N-acetyl cyslein suppress fetal inflammatory cytokine responses to material lipopolysaccharide", *Am J Obstet Gynenol.*, 195:1053-7 (2006).
Beloosesky, et al., "N-acetylcysteine suppresses amniotic fluid and placenta inflammatory cytokine responses to lipopolysaccharide in rats", *Am. J Obstet. Gynecol.*, 194:268-73 (2006b).
Ben-Ari, "N-acetylcysteine in acute hepatic failure (non-paracetamol-induced)", *Hepatogastreonterology*, 47(33):786-9 (2000).
Bennewitz, et al., "Nanotechnology for delivery of drugs to the brain for epilepsy", *Neurotherapeutics*, 6(2):323-36 (2009).
Berk, et al., "The promise of N-acetylcysteine in neuropsychiatry", *Trends Pharma. Sci.*, 34(3):167-77 (2013).
Benz, "Strcture and faction of porins from gram negative bacteria", *Microbial.*, 42:359-93 (1998).
Berger, et al., "Pathophysiology of X-linked adrenoleukodystrophy", *Biochimie*, 98:135-42 (2014).
Bickel, et al., "Delivery of peptides and proteins through the blood-brain barrier",, *Adv Drug Deliv Rev.*, 46:247-79 (2001).
Billiards, et al., "Development of microglia in the cerebral white matter of the human fetus and infant", *J Comp Neurol.*, 497:199-208 (2006).
Block, et al., "Microglia-mediated neurotoxicity: uncovering the molecular mechanisms", *Nat Rev Neurosci.*, 8:57-69 (2007).
Borgstrom, et al., "Pharmacokinetics of N-acetylcysteine in man", *Eu J Clin Pharmacol.*, 31:217-22 (1986).
Bosnjkovic, "A dendrimer-based immunosensor for improved capture and detection of tumor necrosis factor-alpha cytokine", *Analytical Achiica Acta,* 720:118-25 (2012).
Bosnjkovic, et al., "Poly(amidoamine) dendrimer-erythromycin conjugates for drug delivery to macrophages involved in periprosthetic inflammation", *Nanomedicine Nanotech Biol Med.*, 7(3):284 (2011).
Bourges , et al., "Ocular Drug Delivery Targeting the Retina and Retinal PigmentEpithelium Using Polylactide Nanoparticles," *Invest. Opthalmol. & Vis. Sci.*, 44:3562-9 (2003).
Bourne, et al., "Dendrimers, a new class ot candidate topical microbicides with activity against herpes simplex virus infection", *Antimicrobial Agents Chemotherapy*, 44:2471-4 (2000).
Bracci, et al., "Synthetic peptides in the form of dendrimers become resistant to protease activity", *J Biol Chem.*,278:46590-5 (2003).
Brauge, et al., "First divergent strategy using two AB(2) unprotected monomers for the rapid synthesis of dendrimers", *J Am Chem Soc.*,123(27):6698-9 (2001).
Breitkreutz, et al., "Improvement of immune functions of HIV infection by sulfur supplementation: two randomized trails", *J Mol Med.*, 78:55-62 (2000).

Buddi, et al., "Emerging treatments for diabetic eye disease: Update on clinical trials", http://www.retinalphysican.com/articleviewer.aspx?articleID-100022 . *Retinal Physician*, Accessed on line May 2, 2015.
Buhimschi, et al., "Protective effect of n-acetylcysteine against fetal death and preterm labor induced by maternal inflammation", *Am K Obstet Gynecol.*, 188:203-8 (2003).
Cakara, et al., "Microscopic M, Protonation Mechanism of Branched Polyamines: Poly(amidoamine) versus Poly(propyleneimine] Dendrimers Croat", *Chem Acta.*, 80:421-8 (2007).
Cakara, et al., "Microscopic Protonation Equilibria of Poly(amidoamine) Dendrimers from Macroscopic Titrations", *Macromolecules*, 36:4201-7 (2003).
Calabretta, et al., "Antibacterial activities of poly(amidoamine) dendrimers terminated with amino and poly(ethylene 8 ycol) groups", *Biomacromolecules*, 8:1807-11 (2007).
Carbonell, et al., "Migration of perilesional microglia after focal brain injury and modulation by CC chemokine receptor 5: an in situ time-lapse confocal imaging study", *J Neurosci.*, 27:30):7040-7 (2005).
Carmody , et al., "Reactive Oxygen Species as Mediators of Photoreceptor ApoptosisIn Vitro," *Exp. Cell Res.* 248(2):520-30 (1999).
Cerqueira, et al., "Microglia response and in vivo therapeutic potential of methylprednisolone-loaded dendrimer nanoparticles in spinal cord injury", *Nanoparticles*, 5:738-49 (2013).
Chaim,et al, "The relationship between bacterial vaginosis and preterm birth: A Review", *Archives Gen Obst*, 259:51-8 (1997).
Chandrasekar, et al., "The development of folate-PAMAM dendrimer conjugates for targeted delivery of anti-arthritic drugs and their pharmacokinetics and biodtstribution in arthritic rats", *Biomaterials*, 28(3):504-12 (2007).
Chang , et al., "Effects of Glucocorticoids on Fas Gene Expression in Bovine Blood Neutrophils," *J. Endocrinol.* 183:569-83 (2004).
Chang , et al., "Inhibition of Microglial Nitric Oxide Production by Hydrocortisone and Glucocorticoid Precursors," *Neurochem Res.* 25(7):903-8 (2000).
Chang , et al., "Minocycline Partially Inhibits Caspase-3 Activation and Photoreceptor Degeneration After Photic Injury," *Ophthalmic Res.* 37:202-13 (2005).
Chauhan, et al., "Solubility enhancement of indomethacin with poly(amidoamine) dendrimers and targeting to inflammatory regions of arthritic rats", *J Drug Targeting*, 12(9-10):575-83 (2004).
Chen, et at.,"Interaction of Dendrimers (Artificial Proteins) with Biological Hydroxyapatite Crystals", *J. Dent. Res.*, 82(6):443-8 (2003).
Chen, "Quaternary annonium functionalized poly(propylene omine) dendrimers as effective antimicrobials structur-activity studies", *Biomacromolecules*, 1:473-82 (2000).
Chen, et al., "Interactions between dendrimer biocides and vacterial membranes", *Biomaterials*, 23:3359-68 (2002).
Cheng, et al., "Polyamidoamine (PAMAM) dendrimers as biocompatible carriers of quinolone antimicrobials: An invitro study", *Eur J Med Chem.*, 42:1032-8 (2007).
Cheng, et al., "Pharmaceutical applications of dendrimers: promising nanocarriers for drug delivery", *Front. Biosci.*, 13:1447-71 (2008).
Choi, et al., "Dexamethasone conjugated poly(amidoamine) dendrimer as a gene carrier for efficient nuclear translocation", *Int J Pharma*, 320:171-8 (2006).
Chow, et al., "Synthesis and Characterization of Outer Sphereâ 'Outer Sphere Connected Organoplatinum Dendritic Networks from Surface-Difunctionalized and Surface-Trifunctionalized Dendritic Monomers", *Macromolecules*, 37(10):3595-605 (2004).
Cloninger, "Biological applications of dendrimers", *Curr Opin Chem Biol.*, 6:742-8 (2002).
Cox, "Glucocorticoid Treatment Inhibits Apoptosis in Human Neutrophils. Separation of Survival and Activation Outcomes," *J Immunol.*, 154:4719-25 (1995).
Cuchelkar, et al., "Synthesis and biological evaluation of disulfide-linked HPMA copolymer-mesochlorin e6 conjugates", *Macromcl Biesci.*, 8:375-B3 (2008).

(56) References Cited

OTHER PUBLICATIONS

Dai, et al., "Intrinsic targeting of inflammatory cells in the brain-subarachnoid administration", *Nanomedicine*, 5(9):1317-29 (2010).
Darbre and Reymond, "Peptide Dendrimers as Artificial Enzymes, Receptors, and Drug-Delivery Agents", *Accounts Chem Res.*, 39(12):925-34 (2006).
De Jesus, et al., "Polyester dendritic systems for drug delivery applications: in vitro and in vivo evaluation", *Bioconjug Chem.*, 13:453-61 (2002).
De Kozak, et al., "Tumor Necrosis Factor and Nitric Oxide Production by Resident Retinal Glial Cells From Rats Presenting Hereditary Retinal Degeneration," *Ocul. Immunol. Inflamm.* 5(2):85-94 (1997).
De Vries, et al., "The blood-brain barrier in neuroinflammatory diseases", *Pharma Rev.*, 49:143-55 (1997).
Dekhuijzen, "Antiosidant properties of N-acetyl cysteine. their relevance in relation to chronic obstructive pulmonary oisease", *Eur Respir J.*, 23:629-36 (2004).
Dennig, et al., "Gene transfer into eukaryotic cells using activated polyamidoamine dendrimers", *Mole Biotrch.*, 90:339-47 (2002).
Desai, et al., "Synthesis and characterization of photocurable polyamidoamine dendrimer hydrogels as a versatile platform for tissue engineering and drug delivery", *Biomacromolecules*, 11(3):666-73 (2010).
Di Biase, et al., "Free radical release in C6 glial cells enriched in hexacosanoic acid: implication for X-linked adrenoleukodystrophy pathogenesis", *Neurochem. Inc.* 44:215-21 (2004).
Dickinson, et al., "Transient lipopolysaccharide-induced cytokine responses in the material serum and amniotic fluid of the guinea pig", *Am J Obst Gyn*, 200:531-34 (2009).
Dierks, et al., "Electroretinographic Effects of an intravitreal Injection of Triamcinolone in Rabbit Retina," *Arch. Ophthalmol.* 123(11):1563-69 (2005).
Dilger and Baker, "Oral N-acetyl L-cysteine is a safe and effective precursor of cysteine", *J. Anim. Sci.*, 19:1-26 (2007b).
Dilger, et al., "Excess dietary L-cysteine, but not L-cystine, is lethal for chicks but not for rats or dogs", *J. Nutrition*, 322:331-8 (2007).
Dinkel et al., "Novel Glucocorticoid Effects on Acute Inflammation in the CNS," *J.Neurochem.* 84(4):705-16 (2003).
Dodd, et al., "Putative neuroprotective agents in neuropsychiatric disorders", *Progress in Neuro-Psychopharmacology & Biological Psychiatry*, 42:135-45 (2003).
Downs, et al., "Long-Tenn Safety of Repeated Blood-Brain Barrier Opening via Focused Ultrasound with Microbubbles in Non-Human Primates Performing a Cognitive Task", *Plos One*, 10(5):e0125911 (2015).
Drew, et al., "Inhibition of Microglial Cell Activation by Cortisol," *Brain Res. Bull.*52(5):391-6 (2000).
Dumont, et al., "Bezafibrate administration improves behavioral deficits and tau pathology in P301S mice", *Hum Mol Genet.*, 21(23):5091-5105 (2012).
Duncan, "The dawning era of polymer therapeutics", *Nature Reviews*, 2:347-60 (2003).
Duncan and Izzo, "Dendrimer biocompatibility and toxicity", *Adv Drug Deliv Rev.*, 57:2215-37 (2005).
Dunlap, et al., "Nanoscopic structure of DNA condensed for gene delivery", *Nucleic Acids Res*, . 25(15):3095-101 (1997).
Dutta, et al ., "Poly(propyleneimine) dendrimer and dendrosome mediated genetic immunization against hepatitis B", *Vaccine*, 26:3389-94 (2008).
Eichler, et al., "Is microglial apoptosis an early pathogenic change in cerebral X-linked adrenoleukodystrophy", *Ann Neurol.*, 63(6):729-42 (2008).
Ellison, et al., "Damage of the outer membrane of enteric gram-negative bacteria by lactoferrin and transferrin", *Infect Immun.*, 56:2774-81 (1988).
El-Remessy, et al., "Neuroproteclive effects of cannabi diol in endotoxin-induced uveilis: critical role of p38 MAPK activation", *Mol Vis.*, 14:2190-203 (2008).

Engelen, et al., "Bezafibrate lowers very long-chain fatty acids in X-linked adrenoleukodystrophy fibroblasts by inhibiting fatty acid elong", *J Inherit Metab Dis.*, 35(6):1137-45 (2012).
Engelen, et al., "X-linked adrenoleukodystrophy (X-ALD): clinical presentation and guidelines for diagnosis, follow-up and management", *Orphanet J Rare Dis.*, 7:51 (2012b).
Engelen, et al., "Bezafibrate for X-linked adrenoleukodystrophy", *PloS one*, 7(7):e41013 (2012c).
Esfand, et Al., "Poly(amidoamine) (PAMAM) dendrimers: from biomimicry to drug delivery and biomediCBl applications", *Drug Discov Today*, 6:427-36 (2001).
Estensen, et al., "N-Acetyl cysteine suppression of the proliferative index in the colon of patients with previous adenomatous colonic polyps", *Cancer Lett.*, 147:109-14 (1999).
Ethier-Chiasson, et al., "Modulation of placental prolein expression of OLR1: implication in pregnancy-related disorders", *Reproduction*, 136: 491-502 (2008).
Eversole, et al., "Protective Effect of the 21-Aminosteroid Lipid Peroxidation InhibitorTirilazad Mesylate (U74006F) on Hepatic Endothelium in Experimental Hemorrhagic Shock," *Circ. Shock* 40(2):125-31 (1993).
Eye Disorders, mMerck Manual Home Edition, Merck Sharp & Dohme Corp. 2010-2011, 9 pgs, http://www.merckmanuals.com/home/eye_disorders.html, accessed on Jan. 23, 2013.
Fang, et al., "Host-guest chemistry of dendrimer-drug complexes: 7. Formation of stable inclusions between acetylated dendrimers and drugs bearing multiple charges", *J Phys Chem B*, 116:3075-82 (2012).
Ferrari, et al., "NAcetylcysteine (D- and L-stereoisomers) prevents apoptotic death of neuronal cells", *J Neurosci.*, 15:2857-66 (1995).
Filipovska, et al., "Delivery of antisense peptide nucleic acids (PNAs) to the cytosol by disulphide conjugation to a lipophilic cation", *FEBS Lett.*, 556:180-6 (2004).
Fischer-Durand, et al., "Design of a New Multifunctionalized PAMAM Dendrimer with Hydrazide-Terminated Spacer Arm Suitable for Metalâ 'Carbonyl Multilabeling of Aldehyde-Containing Molecules", *Macromolecules*, 40(24):8568-75 (2007).
Flora, et al., "Lead induced oxidative stress and its recovery following co-administration of melatonin or N-acetyl cysteine during chelation with succimer in male rats", *Cell Mol Biol.*, 50: 543-5 (2004).
Fourcade, et al., "Early oxidative damage underlying neurodegeneration in X-adrenoleukodystrophy", *Hum. Mol. Genet.*, 17:1762-73 (2008).
Fourcade, et al., "Thyroid hormone induction of the adrenoleukodystrophy-related gene (ABCD2)", *Mol Pharma.*, 63(6):1296-303 (2003).
Fremount, "Biological effects of resveratrol", *Life Sci.*, 66(8):663-73 (2000).
Fuchs, et al., "A surface-modified dendrimer set for potential application as drug delivery vehicles: synthesis, in vitro toxicity, and intracellular localization", *Chemistry*,10(5):1167-92 (2004).
Fujiki, et al., "Peroxisome biogenesis in mammalian cells", *Front Physiol.*, 5:307 (2014).
Fung, et al., "Chemotherapeutic drugs released from polymers: distribution of 1,3-bis(2-chloroethyl)-1-nitrosourea in the rat brain", *Pharm Res.*, 13:671-82 (1996).
Gal, et al., "Mutations in MERTK, The Human Orthologue of the RCS Rat RetinalDystrophy Gene, Cause Retinitis Pigmentosa," *Nat.. Genet.* 26(3):270-1 (2000).
Galea, et al., "Oxidative stress underlying axonal degeneration in adrenoleukodystrophy: a paradigm for multifactorial neurodegenerative diseases", *Biochim Biophys Acta.*, 1822(9):1475-88 (2012).
Galino, et al., "Oxidative damage compromises energy metabolism in the axonal degeneration mouse model of X-adrenoleukodystrophy", *Antioxid Redox Signal.*, 15(8):2095-107 (2011).
Gibson, et al., "Recent advances in topical therapeutics for vitreoretinal diseases", *US Ophthalmic Review*, 8(1) (2015).
Gillies, et al. "Pioglitazone," *Drugs*, 60(2):333-43 (2000).
Gillies and Frechet, "Dendrimers and dendritic polymers in drug delivery", *Drug Dlivery Today*, 10:35-43 (2005).

(56) References Cited

OTHER PUBLICATIONS

Giri et al., "Stimuli-responsive controlled-release delivery system based on mesoporous silica nanorods capped with magnetic nanoparticles", *Angew. Chem., Int Ed.* 44:5038-44 (2005).
Glezer, et al., "Glucocorticoids: Protectors of the Brain During Innate Immune Responses," *Neuroscientist* 10(6):538-52 ( 2004).
Gomez, et al., "Antibiotic administration to patients with preterm premature rupture of membranes does not eradicate intra-amniotic infection", *J. Matern. Fetal Neonatal Med.* 20:167-73 (2007).
Gondcaille, et al., "Phenylbutyrate up-regulates the adrenoleukodystrophy-related gene as a nonclassical peroxisome proliferator", *J Cell Biol.*, 169(1):93-104 (2005).
Gonzalex, , et al., "Glucocorticoids Antagonize AP-1 by Inhibiting the Activation/Phosphorylation of JNK Without Affecting Its Subcellular Distribution," *J.Cell Biol.* 150(5):1199-208 (2000).
Good, et al., "Lactobacillus rhamnosus HN001 decreases the severity of necrotizing enterocolitis in neonatal mice and preterm piglets: evidence in mice for a role of TLR9", *Am J Physiol Gctstrointest Liver Physiol.*, 306(11):G1021-32 (2014).
Goodwin, et al., "Rapid, Efficient Synthesis of Heterobifunctional Biodegradable Dendrimers", *J Am Chem Soc.*,129(22):6994-5 (2007).
Goyal, et al., "Multifunctionalization of dendrimers through orthogonal transformations", *Chemistry*, 13(31):8801-10 (2007).
Green and Kroemer, "The Pathophysiology of Mitochondrial Cell Death," *Science*, 305(5684):626-9 (2004).
Grinstaff, "Designing hydrogel adhesives for corneal wound repair", *Biomaterials*, 28(35):5205-14 (2007).
Gupta, et al., "Activated Microglia in Human Retinitis Pigmentosa, Late-Onset RetinalDegeneration, and Age-Related Macular Degeneration," *Exp. Eye Res.* 76(4):463-71 (2003).
Gurdag, "Activity of dendrimer-methotrexate conjugates on methotrexate-sensitive and resistant cell lines", *Bioconjugate Chem.*, 17:275-83 (2006).
Halford, "Dendr mers branch out ", *C& EN*, 83:30-6 (2005).
Hall, et al., "Antioxidant effects in brain and spinal cord injury", *J Neurotrauma*, 9(sup.1):165-72 (1992).
Han, et al., "Multifunctional Dendrimer-Templated Antibody Presentation on Biosensor Surfaces for Improved Biomarker Detection", *Adv. Fund. Mater.*, 20:409-21 (2010).
Harada, et al., "Kinetic analysis of covalent binding between N-acetyl-L-cysteine and albumin through the formation of mixed disulfides in human and rat serum in vitro", *Pharm Res.*, 19:1648-54 (2002).
Harnett, et al., "Dose-dependent lipopolysaccharide-induced fetal brain injury in guinea pig", *Am J Obstetrics Gyngcol.*, 197:179 e171 177 (2007).
Heier, et al, "VBP15, a novel anti-inflammatory and membrane-stabilizer, improves muscular dystrophy without side effects", *EMBO Mol Med.*, 5(10): 1569-85 (2013).
Helander, et al., "Fluorometric assessment of gram-negative bacterial permeabilization", *J Appl Microbiol*, 88:213-9 (2000).
Higdon, et al., "Resveratrol," Linus Pauling Institute Micronutrient Information Center, http://lpi.oregonstate.edu/mic/dietary-factors/pbytochemicals/resveratrol, accessed (Oct. 2015).
Hinman, et al., "Upeelacis, Preparation and characterization of monoclonal antibody conjugates of the calicheamicins: A novel and potent family of antitumor antibiotics", *J. Cancer Res.* 53: 3336-42 (1993).
Hollins, et al., "Toxicogenomics of drug delivery systems: exploiting delivery system-induced changes in target gene expression to enhance siRNA activity", *J Drug Targeting*, 15:83-8 (2007).
Hong, et al., "Glutathione-mediated delivery and release using monolayer protected nanoparticle carriers", *J Am. Chem. Soc.*, 128:1078-9 (2006).
Hong, et al., "Interaction of polycationic polymers with supported lipid bilayers and cells: nanoscale hole formation and enhanced membrane permeability", *Bioconjug Chem.*, 17:728-34 (2006b).
Horwitz, et al., "Efficacy of Lipid Soluble, Membrane-Protective Agents Against Hydrogen Peroxide Cytotoxicity in Cardiac Myocytes," *Free Radic. Biol. Med.* 21(6):743-53 (1996).
Hou., et al., "Antimicrobial dendrimer active against *Escherichia coli* biofilms", *Bioorg Med Chem Lett*, 19:5478-81 (2009).
Huang, et al., "Efficient gene delivery targeted to the brain using a transferrin-conjugated polyethyleneglycol-modified polyamidoamine dendrimer", *FASEB*, 21(4):1117-25 (2007).
Hughes, et al., "Minocycline Delays Photoreceptor Death in the RDS Mouse Through a Microglia-Independent Mechanism," *Exp. Eye Res.* 78(6):1077-84 (2004).
Ibrahim, et al., "Antimicrobial Effects of Lysozyme against Gram-Negative Bacteria Due to Covalent Binding of Palmitic Acid", *J Agnc Food Chem.*, 39:, 2077-82 (1991).
Iezzi, et al., "Dendrimer-based targeted intravitreal therapy for sustained attenuation of neuroinflammation in retinal degeneration", *Biomaterials*, 33(3):979-88 (2012).
Ignarro, "Lysosome Membrane Stabilization In Vivo: Effects of Steroidal and Nonsteroidal Anti-Inflammatory Drugs on the Integrity of Rat Liver Lysosomes," *J.Pharmacol Exp. Ther.* 182(1):179-88 (1972).
Inapagollo, "In vivo efficacy of dendrimer-methylprednisolone conjugate formulation for the treatment of lung inflammation", *Intl J Pharma.*, 399(1-2):140-7 (2010).
Islam, et al., "Controlling the cytokine storm in severe bacterial diarrhoea with an oral toll-like receptor 4 antagonist", *Immunology*, 147:178-89 (2015).
Islam, et al., "HPLC Separation of Different Generations of Poly(Amidoamine) Dendrimers Modified With Various Terminal Groups," Anal. Chem, 77:2063-70 (2005).
Jaffe, et al., "Fluocinolone Acetonide Implant (Retisert) for Non-infectious Posterior Uveitis: Thirty-Four-Week Results of a Multicenter Randomized Clinical Study," *Ophthalmol.* 113:1020-7 (2006).
Jaffe, et al., "Fluocinolone Acetonide Sustained Drug Delivery Device to Treat Severe Uveitis," *Ophthalmol.* 107:2024-33 (2000b).
Jaffe, et al., "Safety and Pharmacokinetics of an lntraocular Fluocinolone Acetonide Sustained Delivery Device," *Invest. Ophthalmol. & Vis. Sci.* 41:3569-75 (2000).
Jain, "Nanobiotechnology-based strategies for crossing the blood-brain barrier", *Nanomedicine (Lond)*, 7(8):1225-33 (2012).
Jallouli, et al., "Influence of surface charge and inner composition of porous nanoparticles to cross blood-brain barrier in vitro", *Inl J Pharma*, 344:103-9 (2007).
Je and Kim, "Chitosan derivatives killed bacteria by disrupting the outer and inner membrane", *J Agric Food Chem.*, 54:6629-33 (2006b).
Je and Kim., "Antimicrobial action of novel chitin derivalive", *Biochim Biophys Acta*, 1760:104-9 (2006a).
Jedlitschky, et al.,"Peroxisomal leukotriene degradation: biochemical and clinical implications", *Adv Enzyme Regul.*, 33:181-94 (1993).
Jevpraseshpant, et al., "The influence of surface modification on the cytotoxicity of PAMAM dendrimers", *Int J Pharm.*, 252:263-6 (2003).
Jiang, et at.,"Tumor Imaging by Means of Proteolytic Activation of Cell-Penetrating Peptides", *PNAS*, vol. 101(51):17867-72 (2004).
Jones, et al., "Cationic PAMAM dendrimers aggressively initiate blood clot formation", *ACS Nano*, 6:9900-10 (2012).
Jones, et al., "Cationic PAMAM dendrimers disrupt key platelet functions", *Mol Pharma.*, 9:1599-611 (2012b).
Jou, et al., "Gangliosides Trigger Inflammatory Responses via TLR4 in Brain Glia," *Am. J. Pathol.*, 168:1619-30 (2006).
Jucker, et al., "Adsorption of bacterial surface polysaccharides on mineral oxides is mediated by hydrogen bonds", *Colloids and Surfaces B*, 9:331-43 (1997).
Jucker, et al., "Quantification of Polymer Interactions in Bacterial Adhesion", *Environ Sci Technol.*, 32:2909-15 (1998).
Kam, et al., "Functionalization of carbon nanotubes via cleavable disulf de bonds efficient intracellular delivery of ciRNA and potent gene sllenoing", *J. Am. Chem Soc.*, 127:12492-3 (2005).
Kambharmpati, et al., "Dendrimer nanoparticles for ocular drug delivery", *J Ocular Pharmacol Ther.*, 29(2):151-65 (2013).
Kaminskas, et al., "The impact of molecular weight and PEG chain length on the systemic pharmacokinetics of PEGylated poly 1-lysine dendritners", Mol Pharm., 5(3): 449-63 (2008).

(56) References Cited

OTHER PUBLICATIONS

Kang, et al,., "Tat-conjugated PAMAM dendrimers as delivery agents for antisense and siRNA oligonucleotides", *Pram Res.*, 22:2099-106 (2005).
Kannan, et al., "Dynamics of cellular entry and drug delivery by dendritic polymers into human epithelial carcinoma cells", *J. Biomater. Sci. Polym. Edn.*, 15:311-30 (2004).
Kannan, et al., "Microglial activation in perinatal rabbit brain induced by intrauterine inflammation detection with 11C-(R)-PK11195 an6 small-animal PE1", *J. Nucl Med.*, 48(6):946-54 (2007).
Kannan, et al., "Magnitude of [(11)C]PK11195 binding is related to severity of motor deficits in a rabbit model of cerebral palsy induced by intrauterine endotoxin exposure", *Dev Neurosci.*, 33:231-40 (2011).
Kannan, et al., "Dendrimer-based postnatal therapy for neuroinflammation and cerebral palsy in a rabbit model", *Sci Trans Med.*, 4(130) (2012).
Kansara, et al., "Routes of ocular drug administration", Drug Delivery Research Advances, Mashkevih Ed Nova Sci Publishers, Inc. pp. 4-6 (2007).
Kapadia, et al., "Mechanisms of anti-inflammatory and neuroprotective actions of PPAR-gamma agonists", *Front Biosci.*, 13:1813-26 (2009).
Katai, et al., "Caspaselike Proteases Activated in Apoptotic Photoreceptors of Royal College of Surgeons Rats," *Invest. Ophthalmol. Vis. Sci.*, 40:1802-7 (1999).
Keelan, et al., "Cytokine abundance in placental tissues: evidence of inflammatory activation in gestational membranes with term and preterm parturition", *Am J Obstetrics Gynecology*, 181: 1530-6 (1999).
Kenny, et al., "Multifunctional receptor-targeted nanocomplexes for the delivery of therapeutic nucleic acids to the brain", *Biomaterials*, 34(36):9190-200 (2013).
Khan, et al., "Administration of N-acetyl cysleine after focal cerebral ischemia protects brain and reduces inflammation in a rat model of experimental sboke", *J Neurosci Res.*,4:519-27 (2004).
Khan, et al., "In vivo biodistribution of dendrimers and dendrimer nanocomposites implications for cancer imaging and therapy", *Tech Cancer Res Treat.*, 4(6):603-13 (2005).
Khan, et al., "Bactericidal Action of Egg Yolk Phosvitin against *Echerichia coli* under Thermal Stress", *J Agric Food Chem.*, 48:1503-06 (2000).
Khan, et al., "Very long-chain fatty acid accumulation causes lipotoxic response via 5-lipoxygenase in cerebral adrenoleukodystrophy", *J Lipid Res.*, 51(7):1685-95 (2010).
Khandare, et al., "Synthesis, cellular transport, and activity of polyamidoarnine dendrimer-methylprednisolone conjugates", *Bioconjugate Chem.* 16:330-7 (2005b).
Kiefer, et al., "Effects of Dexamethasone on Microglial Activation In Vivo: Selective Downregulation of Major Histocompatibility Complex Class II Expression in Regenerating Facial Nucleus," *J Neuroimmunol.* 34(2):99-108 (1991).
Kim and Wogan, "Mutagenesis oflhe supF gene of pSP189 replicating in AD293 cells cocultivated with activated macrophages: roles of nitric oxide and reactive oxygen species", *Chem. Res. Toxicol.*, 19:1483-91 (2006).
Kim, et al., "Systematic investigation of polyamidoamine dendrimerc surface-modified with poly(ethylene glycol) for drug delivery applications: synthesis, characterization, and evaluation of cytotoxicity", *Bioconjug Chem.*, 19:1660-72 (2008).
Kim, et al., "Use of single-site-functionalized PEG dendrons to prepare gene vectors that penetrate human mucus barriers", *Angew Chem Int Ed Engl.*, 52(14):3985-8 (2013).
Kirpotin, et al., "Antibody targeting of long-circulating lipidic nanoparticles does not increase tumor localization but does increase internalization in animal models", *Cancer Res.*, 66:6732-40 (2006).
Kitchens, et al., "Transepithelial and endothelial transport of poly (amidoamine) dendrimers", *Adv Drug Deliv Rev.*, 57(15):2163-76 (2005).
Kitchens, et al., "Endocytosis and interaction of poly(amidoamine) Dendrimers with caco-2 cells", *Pharm Res.*, 24:2138-45 (2007).
Kobayashi, et al., "Multimoal nanoprobes for radionuclide and five color near infrared optical lymphatic imaging", *ACS Nano*, 1(4):258-64 (2007).
Kobayashi, et al., "Dynamic micro-magnetic resonance imaging of liver micrometastasis in mice with a novel liver macromolecular magnetic resonance contrast agent DAB-Am64-(1B4M-Gd)(64)", *Cancer Res.*, 61(13):4966-70 (2001).
Kobayashi, et al., "Renal tubular damage detected by dynamic micro-MRI with a dendrimer-based magnetic resonance contrast agent", *Kidney Int.*,61(6):1980-5 (2002).
Kobayashi, et al.,"3D-Micro-MR Angiography of Mice Using Macromolecular MR Contrast Agents With Polyamidoamine Dendrimer Core With Reference to Their Pharmacokinetic Properties", *Magnetic Resonance in Medicine*, 45:454-60 (2001b).
Kobayashi, et aI., "Comparison of the Macromolecular MR Contrast Agents with Ethylenediamine-Core Versus Ammonia-Core Generation-6 Polyamidoamine Dendrimer", *Bioconjugate Chem.*, 12:100-7 (2001c).
Kolhatkar, et al., "Surface acetylation of polyamidoamine (PAMAM) dendrimers decreases cytotoxicity while maintaining membrane permeability",*Bioconjug Chem.*, 18(6):2054-60 (2007).
Kolhe, et al., "Drug complexation, in vitro release and cellular entry of dendrimers and hyperbranched polymer", *Intl. J Pharma*, 259(1-2):143-60 (2003).
Kolhe, et al., "Hyperbranched polymer-drug conjugates with high drug payload for enhanced cellular delivery", *Pharma Research*, 21(12):2185-95 (2004).
Kolhe, et al,, "Preparation cellular transport and activity of polyamidoamine-based dendritic nanodevices with a high drug payload", *Biomaterials*, 27:660-9 (2006).
Kolhatkar, et al., "Surface acetylation of polyamidoamine (PAMAM) dendrimers decreases cytotox! city while maintaining membrane permeability", *Bioconjug Chem.*, 18:2054-60 (2007).
Kommareddy and Arnie, "Preparation and evaluation of thiol-modified gelatin nanoparticles for intracellular DNA delivery in response to glutathione ", *Bioconfugate Chem.*, 16:1423-32 (2005).
Kono, et al., "Transfection activity of polyamidoamine dendrimers having hydrophobic amino acid residues in the periphery", *Bioconjug Chem.*,16(1):208-14 (2005).
Kou, et al., "Glutathione- and cysteine-induced transverse overgrowth on gold nanorods", *J Am Chem. Soc.*, 129:6402-4 (2007).
Kroll, et al., "Outwitting the blood-brain barrier for therapeutic purposes: osmotic opening and other means",*Neurosurgery*, 42(5):1099-100 (1998).
Kukowska-Latallo, et al., "Nanoparticle targeting of anticancer drug improves therapeutic response in animal model of human epithelial cancer", *Cancer Res.*,65:5317-24 (2005).
Kukowska-Latallo et al., "Efficient transfer of genetic material into mammalian cells using starburst polyamidoamine dendrimers", *PNAS*, 93:4897-902 (1996).
Kukowska-Latallo, et al., "Intravascular and endobronchial DNA delivery to murine lung tissue using a novel, nonviral vector", *Hum Gene Ther*, 11(10):1385-95 (2000).
Kurtoglu, et al., "Poly(amidoamine) dendrimer-drug conjugates with disulfide linkages for intracellular drug delivery", *Biomalerials*, 30, 2112-21 (2009).
Kurtoglu, et al., "Drug release characteristics of PAMAM dendrimer-drug conjugates with different linkers", *Intl J Pharma*, 384(1-2):189-94 (2010).
Landers, et al., Prevention of Influenza Pneumonitis by Sialic Acid-conjugated Dendritic Polymers, *J. of Infectious Diseases*, 186:1222-30 (2002).
Lebreton, et al., "Antibacterial single-bead scieening", *Tetrahedron*, 59:10213-22 (2003).
Lee, et al., "A single dose of doxorubicin functionalized bow-tie dendrimer cures mice bearing C-26 colon carcinomas'", *PNAS*, 103:16649-56 (2006).
Lee, et al., "Designing dendrimers for biological applications", *Biotech.*, 23:1517-26 (2005).

(56) References Cited

OTHER PUBLICATIONS

Lee, et al., "Synthesis of symmetrical and unsymmetrical PAMAM dendrimers by fusion between azide- and alkyne-functionalized PAMAM dendrons", Bioconjugate Chem., 18:579-84 (2007).
Lehmann, et al., "Inhibition of Tumor Necrosis Factor-Alpha Release in Rat Experimental Endotoxemia by Treatment With the 21-Aminosteroid U-74389G," Crit. Care Med. 27(6):1164-7 (1999).
Lentz, et al., "Viral vectors for gene delivery to the central nervous system", Neurobiol Dis, 48(2):179-188 (2012).
Lesniak, et al., "Biodistribution of fluorescently labeled PAMAM dendrimers in neonatal rabbits: effect of neuroinflammation", Mol Pharma,10:4560-71 (2013).
Lesniak, et al., "Synthesis and characterization of PAMAM dendrimer based multifunctional nanodevices for targeting alphavbeta3 integrins", Bioconjug Chem., 18(4):114-854 (2007).
Lessio, et al., "Cyclosporine A and NAC on the inducible nitric oxide synthase expression and nitric oxide synthesis to rat renal artery cultured cells", Kidney Int., 68:2508-16 (2005).
Lettéron, et al., ., "Glucocorticoids Inhibit Mitochondrial Matrix Acyl-CoA ehydrogenases and Fatty Acid-Oxidation," Am. J. Physiol. 272:G1141-50 (1997).
Li, et al., "Poly(vinyl alcohol) nanoparticles prepared by freezing-thawing process for protein/peptide drug delivery ", J Controlled Release, 56:117-26 (1998).
Li, et al., "Pharmacokinetics and biodistribution of nanoparticles", Mol Pharm., 5(4):496-504 (2008).
Li, et al., "Peroxynitrite generated by inducible nitric oxide synthase and NADPH oxidase mediates microglial toxicity to oligodendrocytes", PNAS, 102:9936-41 (2005).
Liang, et al., "Long-Term Protection of Retinal Structure But Not Function Using RAAV.CNTF in Animal Models of Retinitis Pigmentosa," Mol. Ther. 4(5):461-72 (2001).
Liang, et al., "PAMAM Dendrimers and Branched Polythyleneglycol (nanoparticles) Prodrugs of (-)-[beta]-D-(2R, 4R)- Dioxolane-Thymine (DOT) and Their Anti-HIV Activity", Antiviral Chemistry and Chemotherapy, 17(6) 321-9 (2006).
Lim and Simanek, "Synthesis of water-soluble dendrimers based on melamine bearing 16 paclitaxel groups", Organic Lett., 10:201-4 (2008).
Liu, et al., "Dendrimeric pyridoxamine enzyme mimics", J Am Chem Soc., 125(40):12110-11 (2003).
Lieb, et al., "Inhibition of LPS-Induced iNOS and NO Synthesis in Primary Rat Microglial Cells," Neurochem. Int. 42(2):131-7 (2003).
Loes, et al., "Adrenoleukodystrophy: a scoring method for brain MR observations", AJNR Am J Neuroradiol, 15:1761-6 (1994).
Lopez, et al., "Antibacterial activity and cytotoxicity of PEGylated poly(amidoamine) dendrimers", Mol Biosyst., 5:1148-56 (2009).
Lopez-Erauskin, et al., "Antioxidants halt axonal degeneration in a mouse model of X-adrenoleukodystrophy", Annals of neurology, 70(1):84-92 (2011).
Louwerse, et al., "Randomized, double-blind, controlled trial of acetylcysteine in amyotrophic lateral sclerosis", Arch. Neural., 52:559-64 (1995).
Lu, et al., "YC-1 attenuates LPS-induced proinflammatory responses and activation of nuclear factor-kB in microglia", Br J Pharmacol. ,151:396-405 (2007).
Mackay, et al., Distribution in brain of liposomes after convection enhanced delivery; modulation by particle charge, particle diameter, and presence of steric coating Brain Res, 1035(2):139-53 (2005).
Majoros, et al., "Acetylation of Poly(amidoamine) Dendrimers", Macromolecules, 36(15):5526-9 (2003).
Majoros, et al., "Poly(amidoamine) dendrimer-based multifunctional engineered nanodevice for cancer therapy", J Med Chem., 48(19):5892-9 (2005).
Makki, et al., "Intrauterine administration of endotoxin leads to motor deceits in a rabbit model: a link between prenatal infection and cerebral palsy", Am. J. Obstet. Gynecol., 199: 651-1651 (2008).
Malik, et al., "Dendrimer-platinate: a novel approach to cancer chemotherapy", Anti Cancer Drugs, 10:767-76 (1999).
Malik, et al., "Dendrimers relationship between structure and biocompatibility in vitro and preliminary studies on the biodistributiom of 125I-labeled polyamidoamine dendrimers in vivo", J Control Release, 65:133-48 (2000).
Mallard, et al., "Astrocytes and microglia in acute cerebral injury underlying cerebral palsy associated with preterm birth",, Pediatr Res., 75:234-40 (2014).
Marano, et al., "Dendrimer Delivery of an Anti-VEGF Oligonucleotide Into the Eye: A Long-Term Study Into Inhibition of Laser-Induced CNV, Distribution, Uptake and Toxicity," Nature Gene Therapy 12:1544-50 (2005).
Marchetti, et al., "Mitochondrial Permeability Transition Is a Central Coordinating Event of Apoptosis," J. Exp. Med., 184(3):1155-60 (1996).
Marquet, et al., "Noninvasive, transient and selective blood-brain barrier opening in non-human primates in vivo",Plos One, 6(7): ):e22598. doi: 10.1371 (2011).
Matsumura and Maeda, "A new concept for macromolecular therapeutics in cancer chemotherapy: mechanism of tumoritropic accumulation of proteins and the antitumor agent", Cancer Res.,46:6387-92 (1986).
Mayhan and Heistad, "Permeability of blood-brain barrier to various sized molecules", Am J Physiol., 248:H712-8 (1985).
Mecke, et al., "Lipid bilayer disruption by polycationic polymers: the roles of size and chemical functional group", Langmuir, 21:10348-54 (2005).
Medline Plus, Blindness and Vision loss, http://www.nlm.nih.gov/medlineplus/ency/article/003040,html, accessed Jan. 23, 2013.
Meister and Anderson, "Glutathione", Annu Rev Biochem.,52:711-60 (1983).
Menjoge, et al., "Transfer of PAMAM dendrimers across human placenta: Prospects of its use as drug carrier during pregnancy", J Controlled Release, 150(3):326-38 (2011).
Menjoge, et al., "Transport and bio distribution of dendrimers across human fetal membranes Implications for intravaginal administration of dendrimer-drug conjugates", Biomaterials, 31(18):50107-21 (2010b).
Menoge et al., "Dendrimer-based drug and imaging conjugates design considerations for nanomedical applications", Drug Deliv Today, 15(5-6):171-85 (2010).
Meyer-Luehmann, et al., "Rspid appearance and local toxicity of amyloid-beta plaques in a mouse model of Alzheimer's disease", Nature; 451:720-4 (2008).
Mignani, et al., "Expand classical drug administration ways by emerging routes using dentrimer drug delivery systems: a concise overview", Adv Drug Delivery Rev., 65(10):1316-30 (2013).
Milovic, et al., "Immobilized N alkylated polyethylenimine avidly kills bacteria by rupturing cell membranes with no resistance developed", Biotechnol Bioeng., 90:715-22 (2005).
Min, et al., "Plasminogen-induced IL-1§ and TNFa production in microglia is regulated by reactive oxygen species", Biophys. Res. Commun., 312:969-74 (2003).
Min, et al., "Gangliosides Activate Microglia via Protein Kinase C and NADPH Oxidase," Glia, 48:197-206 (2004).
Mintzer and Simanek, "Nonviral vectors for gene delivery", Chem Rev, 109(2): 259-302 (2009).
Misha, et al., "Surface-engineered dendrimers: a solution for toxicity issues.", J Biomaterials Sci., 20:141-66 (2009).
Mishra, "PAMAM dendrimer-azithromycin conjugate nanodevices for the treatment of chlamydia trachomatis infections", Nanomed NanoTech, 7(6):935-44 (2011).
Mishra, et al., "Dendrimer-enabled moderation of gene expression in chlamydia trachomatis", Molecular Pharma., 9(3):413 (2012).
Mishra, et al., "Dendrimer brain uptake and targeted therapy for brain injury in a large animal model of hypothermic circulatory arrest", ACS Nano, 8:2134-47 (2014).
Morato, et al., "Pioglitazone halts axonal degeneration in a mouse model of X-linked adrenoleukodystrophy", Brain, 136(Pt 8):2432-43 (2013).
Morato, et al., "Activation of sirtuin 1 as therapy for the peroxisomal disease adrenoleukodystrophy", Cell Death Differ., 22:1742-53 (2015).
Mulders, et al., "Synthesis of a novel amino acid based dendrimer", Tetrahedron Lett., 38(4):631-4 (1997).

(56) References Cited

OTHER PUBLICATIONS

Mumper, et al., "Formulating a sulfonated antiviral dendrimer in a vaginal microbicidal gel having dual mechanisms of action", *Drug Dev Ind Pharma.*, 35:515-24 (2009).
Myers, "The Effect of Hydroxyl Ion Concentration on the Thermal Death Rate of Bacterium Coli", *J Bacterio*, 15:341-56 (1928).
Mythri, et al., "Novel mucoadhesive polymers-A Review", *J App Pharma Sci.*, 1(8):37-42 (2011).
Naberezhnykh, et al., "Interaction of chitosans and their N-acylated derivatives with lipopolysaccharide of gram-negative bacteria", *Biochemistry (Mosc)*, 73:432-41 (2008).
Nagaraju, et al., "Delta 9-11 Compound, VBP15: Potential Therapy for DMD", Children's National Medical Center Washington DC (accessed Oct. 2015).
Najlah, et al., "In vitro evaluation of dendrimer prodrugs for oral drug delivery", *Int J Pharm.*, 336:183-90 (2007).
Najlah, et al., "Synthesis, characterization and stability of dendrimer prodrugs", *Int J Pharm.*,308:175-82 (2006b).
Nance, et al., "A dense poly(ethylene glycol) coating improves penetration of large polymeric nanoparticles within brain tissue", *Sci Transl Med,*, 4:149ra119 (2012).
Nance, et al., "Brain-penetrating nanoparticles improve paclitaxel efficacy in malignant glioma following local administration", *ACS Nano.*,8(10):10655-64 (2014).
Napoli and Neumann, "Microglial clearance function in health and disease", *Neuroscience*, 158:1030-3B (2009).
Navath, et al., "Amino acid-functionalized dendrimers with heterobifunctional chemoselective peripheral groups for drug delivery applications", *Biomacromolecules*, 11(6):1544-63 (2010b).
Navath, et al., "Dendrimer-drug conjugates for tailored intracellular drug release based on glutathione levels", Bioconjugate Chem., 19(12):2446-53 (2008).
Navath, et al., "Injectable PAMAM dendrimer-PEG hydrogels for the treatment of genital infections: formation and in vitro and in vivo evaluation", *Molecular Pharma*, 8(4):1209-23 (2011).
Navath, et al., "Stimuli-responsive star polyethylene glycol) drug conjugates for improved intracellular delivery of the drug in neuroinflammation", *J Controlled Release*, 142(3):447-56 (2010).
Neal, et al., "Discovery and validation of a new class of small molecule toll-like receptor 4 (TLR4) inhibitors ", *Plos One*, 8(6):e65779 (2013).
Neeves, et al., "Dilation and degradation of the brain extracellular matrix enhances penetration of infused polymer nanoparticles", *Brain Res.*, 11B0:121-32 (2007).
Nigavekar, et al., "3H dendrimer nanoparticle organ/tumor distribution", *Pharm Res.*, 21(3):476-83 (2004).
Nimmerjahn, et al., "Resting microglial cells are highly dynamic surveillants of brain parenchyma in vivo", *Science*, 308:1314-18 (2005).
Noack, et al., "Nitrosative stress in primary glial cultures after induction of the inducible isoform of nitric oxide synthase (i-NOS)", *Toxicology*, 148:133-42 (2000).
Oh, et al., "Synthesis, Characterization, and Surface Immobilization of Metal Nanoparticles Encapsulated within Bifunctionalized Dendrimers",*Langmuir*,19(24): 10420-5 (2003).
Okuda, et al., "Biodistribution characteristics of amino acid dendrimers and their PEGylated derivatives after intravenous administration", *J Control Release*, 114(1):69-77 (2006).
Olivas, "ReveraGen BioPharma Announces Start of Phase 1 Clinical Trial of VBP15 Dissociative Steroid Drug," http://www.prnewswire.com/news-releases/reveragen-biopharma-announces-start-of-phase-1-clinical-trial-of-vbp15-dissociative-steroid-drug-300037964.html, media release, (Feb. 18, 2015).
O'Mahony, et al., "Non-viral nanosystems for gene and small interfering RNA delivery to the central nervous system: formulating the solution", *J Pharm Sci*, 102(10):3469-84 (2013).
Ortega, et al., "Amine and ammonium functionalization of chlaromethylsilane-ended dendrimers. Antimicrobial activity studies", *Org Biomol Chem.* 6:3264-9 (2008).

Oupicky, et al., "Laterally stabilized complexes of DNA with linear reducible polycations: strategy for triggered intracellular activation of DNA delivery vectors", *J. Am Chem. Soc.*, 124:, 8-9 (2002).
Padilla, et al., "Polyster dendritic systems for drug delivery applicastions:Vitro and in Vivo evaluation", *Bioonjugate*, 13:453-61 (2002).
Paintlia, et al., "Lipopolysaccharidminduced peroxisomal dysfunction exacerbates cerebral white maner injury attenuation by N-acetyl cysteine", *Exp. Neurol.*, 210:560-76 (2008).
Paleos, et al., "Acid- and salt-triggered multifunctional poly(propylene imine) dendrimer as a prospective drug delivery system", *Biomacromolecules*, 5(2):524-9 (2004).
Palmer, et al., "S-Nitrosothiols signal hypoxia-mimetic vascular pathology", *J Clin Invest.*, 117:2592-601 (2007).
Panyam , et al., "Fluorescence and Electron Microscopy Probes for Cellular and Tissue Uptake of Poly(D,L-Lactide-Co-Glycolide) Nanoparticles," *Met. J. Pharm.* 262:1-11 (2003).
Panyam , et al., "Polymer Degradation and In Vitro Release of a Model Protein From Poly(D,L-Lactide-Co-Glycolide) Nano- and Microparticles," *J. Control.* Release 92:173-87 (2003b).
Pardridge, "GSM: Blood-brain barrier delivery",. *Drug Discov. Today*, 12(1-2):54-61 (2007).
Pardridge, "Drug transport across the blood-brain barrier", *J Cereb Blood Flow Metab*, 32:1959-72 (2012).
Pathak, et al., "Recent trends in non-viral vector-mediated gene delivery", *Biotechnol J*, 4(11):1559-72 (2009).
Patel. et al, "Polymeric nanoparticles for drug delivery to the central nervous system", *Adv Drug Delivery Rev*, 64(7):701-5 (2012).
Patil, et al., "Internally cationic polyamidoamine PAMAM-OH dendrimers for siRNA delivery: effect of the degree of quatermization and cancer targeting", *Biomacromolecules*, 10:258-66 (2009).
Patri, et al., "Targeted drug delivery with dendrimers: comparison of the release kinetics of covalently conjugated drug and non-covalent drug inclusion complex", *Adv Drug Deliv Rev.*, 57:2203-14 (2005).
Patrick, et al., "Developmenl of a guinea pig model of chorioamniotitis and fetal brain injury", *Am J Obstetrics and Gyn.*, 191:1205-11 (2004).
Pawlik and Bing, "Quantitative capillary topography and blood flow in the cerebral cortex of cats: an in vivo microscopic study", *Brain Res.,*, 208(1):35-58 (1981).
Pedrelli, et al., "Thyroid hormones and thyroid hormone receptors: effects of thyromimetics on reverse cholesterol transport", *World J Gastroenterol.*, 16(47):5958-64 (2010).
Perry, et al., "Microglia in neurodegenerative disease", *Nat Rev Neurol.*, 6:193-201 (2010).
Perry, et al., "Glutathione levels and variability in breast tumors and normal tissue", *Cancer*, 72: 783-7 (1993).
Perez-Martinez, et al., "The use of nanoparticles for gene therapy in the nervous system", *J Alzheimers Dis*, 31(4):697-710 (2012).
Perumal, et al., "Effects of branching architecture and linker on the activity of hyperbranched polymer-drug conjugates", *Bioconjugates Chem.*, 20(5):842-96 (2009).
Perumal, et al., "The effect of surface functionality on cellular trafficking of dendrimers", *Biomaterials*, 29(24-25):3469-76 (2008).
Petty, et al., "Junctional complexes of the blood-brain barrier: permeability changes in neuroinflammation", *Prog Neurobiol.*, 68:311-23 (2002).
Pikkemaat, et al.,"Dendritic PARAS EST Contrast Agents for Magnetic Resonance Imaging", *Contrast Media Mol. Imaging*, 2:229-39 (2007).
Powers and Moser, "Peroxisomal disorders: genotype, phenotype, major neuropathologic lesions, and pathogenesis", *Brain Pathol.*, 8(1):101-20 (1998).
Powers, et al., "The dorsal root ganglia in adrenomyeloneuropathy: neuronal atrophy and abnormal mitochondria" *J Neuropathol Exp Neurol.*, 60(5):493-501 (2001).
Pujol, et al., "Late onset neurological phenotype of the X-ALD gene inactivation in mice: a mouse model for adrenomyeloneuropathy", *Hum Mol Gene.,*, 11(5):499-505 (2002).
Pyo , et al., "Gangliosides Activate Cultured Rat Brain Microglia," *J.Biol. Chem.*, 274:34584-9 (1999).

(56) References Cited

OTHER PUBLICATIONS

Qian, et al. "Synergistic inhibition of human glioma cell by temozolomide and PAMAM-mediated miR-21i", *Appl Polymer*, DOI: 10.1002/app.37823 (2013).

Qi, et al., "PEG-conjugated PAMAM Dendrimers Mediate Efficient Intramuscular Gene Expression", *Aaps J*, 11(3):395-405 (2009).

Rajaguru, et al., "Development of improved retinal prosthesis, using local release polymer coatings and sustained release dendrimer-drug nanodevices", Am Inst of Chem Engineers, Annual meeting Session # 447d-(22b), Nov. 2006.

Rajur, et al., "Covalent protein-oligonucleotide conjugates efficient delivery of antisense molecules", *Bioconjugate Chem.*, 8:g3-g40 (1997).

Régina, et al., "Antitumour activity of ANG1005, a conjugate between paclitaxel and the new brain delivery vector Angiopep-2", *Br. J. Pharmacol.*, 155(2):185-97 (2008).

Reiter, et al., "Cytotoxic and antitumor activity of a recombinant immunotoxin composed of disulfide-stabilized anti-TAC Fv fragment and truncated pseudomonas exoloxin", *Int. J. Cancer*, 58:142-149 (1994).

Rinderknecht, et al., "Transfer of dendrimers in the perfused human placental lobule in citro prospects for use as drug carriers during pregnancy", *Birth Defects Res part A*, 88(5):351 (2010).

Romero, et al., "Inflammation in pregnancy: its roles in reproductive physiology, obstetrical complications, and fetal injury", *Nutr Rev.*, 65:5194-202 (2007a).

Romero, et al., "A fetal systemic inflammatory response is followed by the spontaneous onset of preterm parturition", *Am. J Obstet Gynecol.*, 179:186-93 (1998).

Romero, et al., "The preterm panurition syndrome", *Int J Obstet Gynaecol.*, 113:17-42 (2006).

Romero, et al., "The role of inflammation and infection in preterm birth", *Semin Reprod. Med.*, 25:21-39 (2007b).

Romero, et al. "Micronutrients and intrauterine infection, preterm birth and the fetal inflammatory response syndrome", *J Nutrition*, 16685-16735 (2003).

Roy et al., "Reactive oxygen species up-regulate CD11b in microglia via nitric oxide: implications for neurodegenerative diseases", *Free Radic. Biol. Med.*, 26:116-21 (2008).

Roy, et al., "Oral gene delivery with ehitosan-DNA nanopartieles gnerates immunologic protection in a murine model of peanut allergy", Nature Med., 5:387-91 (1999)., *Free Radic Biol Med.*, 45:686-99 (2008).

Rui, et al., "Displasmenyleholine-folate liposomes: an efficient vehicle for intracellular drug delivery", *J Am Chem Soc.*, 120(44):11213-18 (1998).

Saad, et al., "Receptor targeted polymers, dendrimers, liposomes: which nanocarrier is the most efficient for tumor-specific treatment and imaging", *J Control Release*, 130(2):107-14 (2008).

Saadani-Makki, et al, "Intrauterine administration of endotoxin leads to motor deficits in a rabbit model: a link between prenatal infection and cerebral palsy", *Am J Obstet Gynecol.*, 199(6):651-9 (2009b).

Saadani-Makki, et al., "Intrauterine endotoxin administration leads to white matter diffusivity changes in newborn rabbits", *J. Child Neurol.*, 24:1179-89 (2009).

Sadekar, et al., "Comparative pharmacokinetics of PAMAM-OH dendrimers and HPMA copolymers in ovarian tumor-bearing mice", *Drug Deliv Transl Res.*, 3(3):260-71 (2013).

Sadekar, et al., "Transepithelial transport and toxicity of PAMAM dendrimers for oral drug delivery", *Adv Drug Del Rev.*, 64:571-88 (2012).

Sahoo, et al., "Residual Polyvinyl Alcohol Associated With Poly (D,L-Lactide-Co-Glycolide) Nanoparticles Affects Their Physical Properties and Cellular Uptake," *J. Control. Release*, 82:105-14 (2002).

Saito, et al., "Drug delivery strategy utilizing conjugation via reversible disulfide linkages: role and site of cellular reducing activities", *Adv Drug Deliv Rev.*, 55:199-215 (2003).

Sakurai, et al., "Effect of Particle Size of Polymeric Nanospheres on Intravitreal Kinetics," *Ophthalmic Res.* 33:31-6 (2001).

Sanvicens, et al., "Oxidative Stress-Induced Apoptosis in Retinal Photoreceptor Cells Is Mediated by Calpains and Caspases and Blocked by the Oxygen Radical Scavenger CR-6," *J. Biol. Chem.* 279(38):39268-78 (2004).

Sarin, et al., "Effective transvascular delivery of nanoparticles across the blood-brain tumor barrier into malignant glicoma cells", *J Trans Med.*, 6(80):1-15 (2008).

Sato, et al., "Pharmacokinetics and enhancement patterns of macromolecular MR contrast agents with various sizes of polyamidoamine dendrimer cores", *Magn Reson Med.*, 46:1169-73 (2001).

Sato, et at.,"Tumor Targeting and Imaging of Intraperitoneal Tumors by Use of Antisense Oligo-DNA Complexed with Dendrimers and/or Avidin in Mice1", *Clinical Cancer Research*, 7:3606-12 (2001b).

Schlageter, et al. "Microvessel organization and structure in experimental brain tumors: microvessel populations with distinctive structural and functional properties",, *Microvasc. Res.*, 58:312-28 (1999).

Schonenberger and Kovacs, "Hypoxia signaling pathways: modulators of oxygen-related organelles", *Front Cell Dev Biol.*, 3:42-19 (2015).

Semmler, et al., "Therapy of X-linked adrenoleukodystrophy", *Expert Rev. Neurother*, 8:1367-79 (2008).

Shcharbin, et al. "How to study dendrimers and dendriplexes III. Biodistribution, pharmacokinetics and toxicity in vivo",, *J Controlled Release*, 181:40-2 (2014).

Shi, et al., "Dendrimer-entrapped gold nanoparticles as a platform for cancer-cell targeting and imaging", *Small*, 3:1245-52 (2007).

Shimazawa, et al., "Neuroprotective effects of minocycline against in vitro and in vivo retinal ganglion cell damage", *Brain Res.*, 1053:185-94 (2005).

Shirai, et al., "Lack of carcinogenicity of butylated hydroxytoluene on long term administration of B6C3F Mice", *Fd Chem Toxic*, 20:861-5 (1982).

Sieving, et al., "Ciliarophic factor (CNTF) for human retinal degeneration phase 1 trial of CNTF delivered by encapsulated cell intraocular implants", *PNAS*, 103(10):3896-901 (2006).

Singh, "Peroxisomal fatty acid oxidation and cellular redox", *Methods Enzymol*, 352:36-372 (2002).

Sivanandan, et al., "Functional group diversity in dendrimers", *Org Lett.*,4(21):3751-3 (2002).

Sk, et al., "Comparative study of microtubule inhibitors—Estramustine and natural podophyllotoxin conjugated PAMAM dendrimer on glioma cell proliferation", *Eu J Med Chem.*, 68:47-57 (2013b).

Sk, et al., "Enhancing the efficacy of Ara-C through conjugation with PAMAM dendrimer and linear PEG: a comparative study", *Biomacromolecules*, 14(3):801-10 (2013).

Smith, et al., "Pioglitazone: mechanism of action", *J Clin Pract Suppl*, (121):13-8 (2001).

Southam, et al., "Drug Redeployment to Kill Leukemia and Lymphoma Cells by Disrupting SCD1-Mediated Synthesis of Monounsaturated Fatty Acids", *Cancer Res.*, 75(12):2530-40 (2015).

Spierings, et al., "Connected to death: the (unexpurgated) mitochondrial pathway of apoptosis", *Science*, 310(5745):66-7 (2005).

Steffensen and Simanek, "Synthesis and manipulation of orthogonally protected dendrimers: building blocks for library synthesis", *Angew. Chem.*, 116:5290-2 (2004).

Steinberg, et al., "Peroxisome biogenesis disorders", *Biochim Biophys Acta.*, 1763(12):1733-48 (2006).

Stence, et al., "Dynamics of microglial activation: a confocal time-lapse analysis in hippocampal slices", *Glia.*, 33(3):256-66 (2001).

Stolp, et al., "Effects of neonatal systemic inflammation on blood-brain barrier permeability and behaviour in juvenile and adult rats", *Cardiovasc Psychiatry Neurol.*, 2011:469046 (2011).

Sun and Zhang, "Cationic polymer optimization for efficient gene delivery", *Mini Rev Med Chem*, 10(2):108-25 (2010).

Svenson, et al., "Dendrimers in biomedical applicatioms refections on the field", *Adv Drug Delivery*, 57(15):2106-29 (2005).

(56) References Cited

OTHER PUBLICATIONS

Sykova, and Nicholson, "Diffusion in brain extracellular space", *Physiol Rev*, 88(4):1277-340 (2008).
Tang, et al., "Insertion mode of a novel anionic antimicrobial peptide MDpep5 {Val-Glu-Ser-Trp-Val) from Chinese traditional edible larvae of housefly and its effect on surface potential of bacterial membrane", *J Pharm Biomed Anal.*, 48:1187-94 (2008).
Tanito, et al., "Cytoprotective effects of geranylgeranylacetone against retinal photoxidative damage" *J Neurosci.*, 25(9):2396-404 (2005).
Tao, et al., "Application of encapsulated cell technology for retinal degeneration diseases", *Expert Opin Biol Ther.*, 6(7):717-26 (2006).
Tao, et al., "Encapsulated cell-based delivery of CNFT reduces photoreceptor degeneration in animal models of retinitis pigmentosa", *Invest Opthalmol Vis Sci.*, 43(10):3292-8 (2002).
Tepel, et al., "Prevention of radiographic-contrast-agent-induced reductions in renal function by acetylcysteine", *NEJM*, 343:180-4 (2000).
Teo, et at, "Preventing acute gut wall damage in infectious diarrhoeas with glycosylated dendrimers", *EMBO Mol Med.*, 4:866-81 (2012).
Thanos, et al., "Sick photoreceptors attract activated microglia from the ganglion cell layer: A model to study the inflammatory cascades in rats with inherited retinal dystrophy", *Brain Res.*, 588(1):21-8 (1992).
Thanos, et al., "The migratory potential of vitally labelled microglial cells within the retina of rats with hereditary photoreceptor dystrophy", *Int J Dev Neurosci.*, 11(5):671-80 (1983).
Thomas, et al., "Targeting and inhibition of cell growth by an engineered dendritic nanodevice", *J Med Chem.*, 48:3729-35 (2005).
Thomas, et al., "Progress and problems with the use of viral vectors for gene therapy", *Nat Rev Genet*, 4(5):346-58 (2003).
Thomas, "Paracetamol (acetaminophen) poisoning", *Pharma Ther.*, 60:91-120 (1993).
Thorne and Nicholson, "In vivo diffusion analysis with quantum dots and dextrans predicts the width of brain extracellular space", *PNAS*, 103(14):5567-72 (2006).
Till, et al., "Pexophagy: the selective degradation of peroxisomes", *Int. J. Cell Biol.* 2012:512721(2012).
Tolar, et al,, "N-acetyl-L-cysteine improves outcome of advanced cerebral adrenoleukodystrophy", *Bone Marrow Transplant*, 39(4), 211-215 (2007).
Tolic, et al., "Electrospray ionization Fourier transform ion cyclotron resonance mass spectrometric characterization of high molecular mass Starburst™ dendrimers", *Intl J of Mass Spectrometry and Ion Processes*, 165-166:405-18 (1997).
Tomalia, et aI.,"Dendrimers as Multi-Purpose Nanodevices for Oncology Drug Delivery and Diagnostic Imaging", *Biochemical Society Transactions*, 35(1):61-7 (2007).
Tso, et al., "Apoptosis Leads to Photoreceptor Degeneration in Inherited Retinal Dystrophy of RCS Rats," Invest. *Ophthalmol. Vis. Sci.*, 35(6):2693-9 (1994).
Tulu, et al/. "Synthesis, characterization and antimicrobial activity of water soluble den6ritic macromolecules", *Eur J Med Chem Ed.*, 4:1093-9 (2009).
Tziveleka, et al., "Synthesis and characterization of guanidinylated poll (propylene imine) dendrimers as gene transfection agents", *J Control Release* 117:137-1'16 (2007).
Ugwumadu, "Role of antibiotic therapy for bacterial vaginosis and intermediate flora in pregnancy". *Best Pactice Research*, 21:391-402 (2007).
Ulbrich, et al., "HPMA copolymers with pH-controlled release of doxorubicin in vitro cytotoxicity and in vivo antitumor activity", *J Controlled Release*, 87:33-47 (2003).
Unal, et al., "Gelation and swellinf behavior of end-linked hydrogels prepared from linear poly(ethylene glycol) and poly(amidoamine) dendrimers", *Polymer*, 47(24):8173-82 (2006).
University of Birmingham. "Contraceptive, cholesterol-lowering drugs used to treat cancer." ScienceDaily, https://www.sciencedaily.com/releases/2015/05/150514102813.htm, (May 2015).

Urakuboa, et al.,"Prenatal exposure to maternal infection alters cytokine expression in the placenta, amniotic fluid, and fetal brain", *Schizophrenia Research*. 47: 27-36 (2001).
Vale, et al., "Paracetamol (acetaminophen) poisoning", *Lancet*, 346:547-52 (1995).
Van Schayck, et al., "Are anti-oxidant and anti-ingammatory treatments effective in different subgroups of COPD A hypothesis", *Respir Med.*, 92:1259-64 (1998).
Vargas, et al., "Neuroglial activation and neuroinflammation in the brain of patients with autism", *Ann Neurol.*,57(1):67-81 (2005).
Verma, et al., "Tunable reactivation of nanoparticle-inhibited-galactosidase by glutathione at intracellular concentrations", *J Am Chem Soc.*, 126:13987-91 (2004).
Viers, et al., "Hydrogels formed by Endlinking Peg to dendrimer crosslink agents", *Polymer Reprints*, 41(1):729 (2000).
Villalonga-Barber, et al., "Dendrimers as biopharmaceuticals: Synthesis and properties", *Curr Topic Med Chem.*, 8:1294-309 (2008).
Vincent, et al.,"Efficacy of Dendrimer-Mediated Angiostatin and Timp-2 Gene Delivery on Inhibition of Tumor Growth and Angiogenesis: In Vitro and In Vivo Studies", *Int. J. Cancer*, 105:419-29 (2003).
Voges, et al., "Imaging-guided convection-enhanced delivery and gene therapy of glioblastoma", *Ann Neurol*, 54(4):479-87 (2003).
Wagner, et al., "DNA-binding transferrin conjugates as functional gene-deli\very agents: synthesis by linkage of polylysine or cthldium homodimer to the lransferrin carbohydrate moiety", *Bioconjugate Chem.*, 2:226-31 (1991).
Waite, et al., "Acetylation of PAMAM dendrimers for cellular delivery of siRNA", *BMC Biotechnol.*, 9:38 (2009).
Wanders, "Peroxisomes, lipid metabolism, and human disease." *Cell Biochem Biophys.*,32: Spring:89-106 (2000).
Wanders, et al., "Peroxisomes, lipid metabolism and lipotoxicity", *Biochim Biophys Acta.*, 1801(3):272-80 (2010).
Wang, et al., "The 21-Aminosteroid Tirilazad Mesylate Protects Against Liver Injury via Membrane Stabilization Not Inhibition of Lipid Peroxidation," *J. Pharm. Exp. Ther.* 277(2):714-20 (1996).
Wang, et al., "Anti-inflammatory and anti-oxidant activity of anionic dendrimer-N-acetyl cysteine conjugates in activated microglial cells", *Intl J Pharma*, 377(1-2):159-68 (2009).
Wang, et al., "Inhibition of bacterial growth and intramniotic infection in a guinea pig model of chorioamnionitis using PAMAN dendrimers", *Intl J Pharma*, 395(1-2):298-308 (2010).
Wang, et al., "Synthesis characterization and in vitro activity of dendrimer-streptokinase conjugates", *Bioconjugate Chem.*, 18(3):791-9 (2007).
Wang, et al., "The role of autophagy in the neurotoxicity of cationic PAMAM dendrimers", *Biomaterials*, 35:7588-97 (2014).
Wang, et al., "N-acetylcysteine reduces lipopolysaccharide-sensitized hypoxic-ischemic brain injury", *Ann. Neurol.*, 61:263-71 (2006).
Waseem, et al., "Exogenous ghrelin modulates release of pro-inflammatory and anti-inflammatory cytokines in LPS stimulated macrophages through distinct signaling pathways", *Surgery*, 143(3):334-42 (2008).
Wells, et al., "Neuroprotection by minocycline facilitates significant recovery from spinal cord injury in mice", *Brain*, 126:162-37 (2003).
Wenzel, et al., "Prevention of Photoreceptor Apoptosis by Activation of the Glucocorticoid Receptor," *Invest. Ophthalmol. Vis. Sci.*, 42(7):1653-9 (2001).
Wheeler, et al., "A defect of sphingolipid metabolism modifies the properties of normal appearing white matter in multiple sclerosis", Brain, 131:3092-3102 (2008).
Wiegand et al., "Agar and broth dilution methods to determine the minimal inhibitory concentration (MIC) of antimicrobial substances", *Nature protocols*, 3:163-75 (2008).
Wiesinger, et al., "The genetic landscape of X-linked adrenoleukodystrophy: inheritance, mutations, modifier genes, and diagnosis", *Appl Clin Genet.*, 8:109-21 (2015).
Win-Shwe, et al., "Effects of PAMAM dendrimers in the mouse brain after a single intranasal instillation", *Toxicol. Lett*, 228:207-18 (2014).

(56) References Cited

OTHER PUBLICATIONS

Winterbourn and Metodiewa, "Reactivity of biologically important thiol compounds with superoxide and hydrogen peroxide", *Free Radic Biol Med.*,27:322-8 (1999).
Wipi, et al., "Synthesis of anti-inflammatory α-and β-linked acetamidopyranosides as inhibitors of toll-like receptor 4 (TLR4)", *Tetrahedron Ltr.*, 56(23):3097-3100 (2015).
Wiwattanapatapee, et al., "Anionic PAMAM dendrimers rapidly cross adult rat intestine in vitro! a potential oral delivery system", *Pharr». Res.*,2:991-98 (2004).
Wiwattanapatapee, et al., "Dendrimers conjugates for colonic delivery of 5-aminosalicylic acid", *J Control Release*, 88:1-9 (2003).
Wolf, et al., "DARS-associated leukoencephalopathy can mimic a steroid-responsive neuroinflammatory disorder", *Neurology*, 84(3):226-30 (2015).
Wohlfart, et al., "Transport of drugs across the blood-brain barrier by nanoparticles", *J Control Release*, 161(2):264-73 (2012).
Wolinsky and Grinstaff, "Therapeutic and diagnostic applications of dendrimers for cancer treatment", *Adv. Drug Deliv Rev.*, 60 (9):1037-55 (2008).
Woller and Cloninger, "The lectin-binding properties of six generations of mannose-functionalized dendrimers", *Org Lett.*, 4(1):7-10 (2002).
Writer, et al., "Lipid peptide nanocomplexes for gene delivery and magnetic resonance imaging in the brain", *J Control Release*, 162(2):340-8 (2012).
Wu, et al., "Multivalent, bifunctional dendrimers prepared by click chemistry", *Chem Commun (Camb)*, (46):5775-7 (2005).
Wu, et al., "Preparation and characterization of novel physically cross-linked hydrogels composed of poly(vinyl alcohol) and amine-terminated polyamidoamine dendrimer", *Macromolecular Bioscience*, 4(2):71-5 (2004).
Xu, et al., "Effect of N-acelylcysteine on lipopolysaccharide-induced intra-uterine fetal death and intra-uterine growth retardation in mice", *Toxicol. Sci.*, 8B:525-33 (2005).
Yan and Sun, "Distribution of intracerebral ventricularly administered neurotropfiins in rat brain end its correlation with trk receptor expression",*Exp Neurol.*, 127:23-36 (1994).
Yang, et al., "Stealth dendrtmers for drug delivery: correlation between PEGylation, cytocompatibility, and drug payload", *J Mater Sci Mater Med.*, 19:1991-7 (2008).
Yang, et al., "Dendrimers for Pharmaceutical and Biomedical Applications," *J.Biomater. Sci. Polymer Ed.* 17:3-19 (2006).
Yang, et al., "Fas and Activation-Induced Fas Ligand Mediate Apoptosis of T Cell Hybridomas: Inhibition of Fas Ligand Expression by Retinoic Acid and Glucocorticoids," *J. Exp. Med.*, 181:1673-82 (1995).
Yeh, et al., "A study of glutathione status in the blood and tissues of patients with breast cancer", *Cell. Biochem. Funct.*, 24:555-9 (2006).
Yip, et al., "Intravenous administration of oral N-acetyl cysteine", *Crit Care Med.*,26:40-3 (1998).
Yiyun, et al., "Polyamidoamine dendrimers used as solubility enhancers of ketoprofen", *Eu J Med Chem.*, 40:1390-3 (2005).
You, et al., "Reducible poly(2 dimethylaminoethyl methacrylate) Synthesis, cylotoxicity, and gene delivery activity", *J. Controlled Release*, 122:217-25 (2007).
Zafarullah, et al., "Molecular mechanisms of N acetyl cysteine actions", *Cell Mol Life Sci.*,60:6-20 (2003).
Zamecnik, "The extracellular space and matrix of gliomas.", *J., Acta Neuropathol*, 110(5):435-442 (2005).
Zeiss, et al., "CNTF Induces Dose-Dependent Alterations in Retinal Morphology in Normal and Rcd-1 Canine Retina," *Exp. Eye Res.*, 82(3):395-404 (2006).
Zeng, et al., "Identification of Sequential Events and Factors Associated With Microglial Activation, Migration, and Cytotoxicity in Retinal Degeneration in rd Mice," *Invest. Ophthalmol. Vis. Sci.* 46(8):2992-9 (2005).

Zhang, et al., "Neuroprotection of Photoreceptors by Minocycline in Light-Induced Retinal Degeneration," *Invest. Ophthalmol. Vis. Sci.*, 45:2753-9 (2004).
Zhang, et al., "Conjugation of Polyamidoamine Dendrimers on Biodegradable Mircoparticles for Nonviral Gene Delivery", *Bioconjugate Chemistry*, 18(6): 2068-76 (2007).
Zhang, et al., "Evaluation of multivalent dendrimers based on melamine: kinetics of thiol-disulfide exchange depends on the structure of the dendrimer ", *J Am Chem Soc.*, 25:5086-94 (2003).
Zhang, et al., "Uniform brain tumor distribution and tumor associated macrophage targeting of systemically administered dendrimers", *Biomaterials*, 52:507-16 (2015).
Zheng, et al., "Multimodal nanoprobes evaluating physiological pore size of brain vasculatures in ischemic stroke models", *Adv Healthc Mater.*, 3(11):1909-18 (2014).
Zhuo, et al., "In vitro release of 5-fluorouracil with cyclic core dendritic polymer", *J Control Release*,57:249-57 (1999).
Zimmermann, et al., "Extracellular matrix of the central nervous system: from neglect to challenge", *Histochem Cell Biol*, 130(4):635-53 (2008).
Zugates, et al., "Synthesis of polys amino esters) with thiol-reactive side chains for DNA delivery", *J Am. Chem. Soc.*, 12B:12726-34 (2006).
Alexiou, et al., "Magnetic Drug Targeting-Biodistribution of the Magnetic Carrier and the Chemotherapeutic agent Mitoxantrone after Locoregional Cancer Treatment", J Drug Targeting, 11(3):139-49 (2003).
Alizadeh, et al., "Tumor-associated macrophages are predominant carriers of cyclodextrin-based nanoparticles into gliomas", Nanomedicine, 6:382-90 (2010).
Apparaju, et al., "Pharmokinetics of gemcitabine in tumor and non-tumor extracellular fluid of brain: an in vivo assessment in rats employing intracerebral microdialysis", Cancer Chemother Pharmacol., 61:223-9 (2008).
Badie, et al., "In Vitro Modulation of Microglia Motility by Glioma Cells Is Mediated by Heptocyte Growth Factor/Scatter Factor", Neurosurgery, 44:1077-83 (1999).
Badie, et al., "Flow cycometric characterization of tumor-associated macrophages in experimental gliomas", Neurosurgery, 46(4):957-62 (2000).
Badie, et al., "Role of Microglia in Glioma Biology", Microscopy Res Tech., 54:106-13 (2001).
Balakrishnan, et al., "Nanomedicine in cerebral palsy", Intl J Nanomedicine, 8:4183-95 (2013).
Bertossi, et al., "Ultrastructural and Morphometric Investigation of Human Brain Capillaries in Normal and Peritumoral Tissues", Ultrastructural Pathology, 21:41-9 (1997).
Blasberg, et al., "Transport of α-Aminoisobutyric Acid Across Brain Capillary and Cellular Membranes", J Cerebral Blood Flow Metab, 3:8-32 (1983).
Boche, et al., "Review: Activation patterns of microglia and their identification in the human brain", Neuropath Applied Neurobiol., 39:3-18 (2013).
Bregy, et al., "The role of Gliadel wafers in the treatment of high-grade gliomas", Exp Rev Anticancer Therapy, 13(12):1453-61 (2013).
Brigger, et al., "Negative preclinical results with stealth nanospheres-encapsulated Doxorubicin in an orthotopic murine brain tumor model", J Controlled Release, 100:29-40 (2004).
Cabral, et al., "Accumulation of sub-100 nm polymeric micelles in poorly permeable tumours depends on size", Nature Nanotechnology, 6:815-23 (2011).
Chauhan, et al., "Strategies for advancing cancer nanomedicine", Nature Materials, 12:958-62 (2013).
Chekhonin, et al., "Targeted delivery of liposomal nanocontainers to the peritumoral zone of glioma by means of monoclonal antibodies against GFAP and the extracellular loop of Cx43", Nanomedicine, 8:63-70 (2012).
Chertok, et al., "Glioma Selectivity of Magnetically Targeted Nanoparticles: A Role of Abnormal Tumor Hydrodynamics", J Controlled Release, 122(3):315-23 (2007).

(56) References Cited

OTHER PUBLICATIONS

Chertok, el al., "Substantiating in vivo magnetic brain tumor targeting of cationic iron oxide nanocarriers via adsorptive surface masking", Biomaterials, 30:6780-7 (2009).
Choi, et al., "Renal clearance of quantum dots", Nature Biotechnology, 25(10):1165-70 (2007).
Choi, et al., "Dynamic fluorescence imaging for multiparametric measurement of tumor vasculature", J Biomedical Optics, 16(4):046008 (2011).
Chouinard-Pelletier, et al., "Use of inert gas jets to measure the forces required for mechanical gene transfection", BioMedical Eng OnLine, 11(67):1-12 (2012).
Curthoys, et al., "Proximal Tubule Function and Response to Acidosis", Clin J Am Soc Nephrol, 9:1627-38 (2014).
Da Fonseca, et al., "Microglia and Macrophages in Malignant Gliomas: Recent Discoveries and Implications for Promising Therapies", Clin Dev Immunol., Article ID 264124:1-5 (2013).
Dai, et al., "Intrinsic targeting of inflammatory cells in the brain by polyamidoamine dendrimers upon subarachnoid administration", Nanomedicine 5(9):1317-29 (2010).
Dave, et al., "The pharmacokinetics of letrozole in brain and brain tumor in rats with orthotypically implanted C6 glioma, assessed using intracerebral microdialysis", Cancer Chemother Pharmacol, 72:349-57 (2013).
Dinda, et al., "A transmission and scanning electron microscopic study of tumoral and peritumoral microblood vessels in human gliomas", J Neuro-Oncology, 16:149-58 (1993).
Dreaden, et al., "Small Molecule-Gold Nanorod Conjugates Selectively Target and Induce Macrophage Cytotoxicity Towards Breast Cancer Cells", Small J, 8(18):2819-22 (2012).
El Andaloussi, et al., "Stimulation of TLR9 with CpG ODN Enhances Apoptosis of Glioma and Prolongs the Survival of Mice with Experimental Brain Tumors", Glia, 54:526-35 (2006).
Gabrusiewicz, et al., "Characteristics of the Alternative Phenotype of Micrglia/ Macrophages and its Modulation in Experimental Gliomas", PLoS ONE, 6(8): e23902 1-12 pages (2011).
Galarneau, et al., "Increased Glioma Growth in Mice Depleted of Macrophages", Cancer Research, 67(18):8874-81 (2007).
Giese, et al., "Cost of Migration: Invasion of Malignant Gliomas and Implications for Treatment", J Clinical Oncology, 21(8):1624-36 (2003).
Haga, et al., "Involvement of the Multidrug Resistance Protein 3 in Drug Sensitivity and Its Expression in Human Glioma", Jp J Cancer Res., 92:211-19 (2001).
Heath, et al., "Nanotechnology and Cancer", Ann Rev Med., 59:251-65 (2008).
Hirano, et al., "Vascular Structures in Brain Tumors", Human Pathology, 6(5):611-21 (1975).
Hobbs, et al., "Regulation of transport pathways in tumor vessels: Role of tumor type and microenvironment", PNAS, 95:4607-12 (1998).
Huang, et al., "Size-Dependent Localization and Penetration of Ultrasmall Gold Nanoparticles in Cancer Cells, Multicellular Spheroids, and Tumors in Vivo", ACS Nano, 6(5):4483-93 (2012).
Huo, et al., "Superior Penetration and Retention Behavior of 50 nm Gold Nanoparticles in Tumors", Cancer Research, 73(1):319-30 (2012).
Hussain, et al., "The role of human glioma-infiltrating microglia/ macrophages in mediating antitumor immune responses", Neuro-Oncology, 8:261-79 (2006).
Hussain, et al., "A Novel Small Molecule Inhibitor of Signal Transducers and Activators of Transcription 3 Reverses Immune Tolerance in Malignant Glioma Patients", Cancer Research, 67(20):9630-6 (2007).
Jackson, et al., "Quantum Dots are Phagocytized by Macrophages and Colocalize with Experimental Gliomas", Neurosurgery, 60:524-30 (2007).
Jain, et al. "Delivering nanomedicine to solid tumors", Ntl Rev Clinical Oncology, 7(11):653-64 (2010).

Komohara, et al., "Possible involvement of the the M2 anti-inflammatory macrophage phenotype in growth of human gliomas", J Pathology, 216:15-24 (2008).
Kostarelos, et al., "Binding and Interstitial Penetration of Liposomes within Avascular Tumor Spheroids", Intl J Cancer, 112:713-21 (2004).
Kostarelos, et al., "Engineering Lipid Vesicles of Enhanced Intratumoral Transport Capabilities: Correlating Liposome Characteristics with Penetration into Human Prostate Tumor Spheroids", J Liposome Res., 15:15-27 (2005).
Lee, et al., "Blood Volume in the Rat", J Nuclear Med., 25:72-6 (1985).
Li, et al., "The molecular profile of microglia under the influence of glioma", Neuro-Oncology, 14(8):958-78 (2012).
Liebner, et al., "Claudin-1 and claudin-5 expression and tight junction morphology are altered in blood vessels of human glioblastoma multiforme", Acta Neuropathol., 100:323-31 (2000).
Locke, et al., "PET imaging of tumor associated macrophages using mannose coated 64Cu liposomes", Biomaterials, 33:7785-93 (2012).
Markovic, et al., "Minocycline reduces glioma expansion and invasion by attenuating microglial MT1-MMP expression", Brain, Behavior, Immunity, 25:624-8 (2011).
Meyers, et al., "Nanoparticles for imaging and treating brain cancer", Nanomedicine (Lond), 8(1):123-43 (2013).
Mildner, et al., "Microglia in the adult brain arise from Ly-6ChiCCR2+ monocytes only under defined host conditions", Nature Neuroscience, 10(12):1544-53 (2007).
Nakashima, et al., "In-vivo Microdialysis Study of the Distribution of Cisplatin into Brain Tumor Tissue after Intracarotid Infusion in Rats With 9L Malignant Glioma", J Pharma Pharmacol., 49:777-80 (1997).
Nitta, et al., "Expression of granulocyte colony stimulating factor and granulocyte-macrophage colony stimulating factor genes in human astrocytoma cell lines and in glioma specimens", Brain Research, 571:19-25 (1992).
Noell, et al., "Selective enrichment of hypericin in malignant glioma: Pioneering in vivo results", Intl J Oncology, 38:1343-8 (2011).
Okada, et al., Tumor-associated macrophage/microglia infiltration in human gliomas is correlated with MCP-3, but not MCP-1, Intl J Oncology, 34:1621-7 (2009).
Orr, et al., "Adenosine A2A receptor mediates microglial process retraction", Nat Neurosci., 12(7):872-8 (2009).
Parney, et al., "Flow cytometry and in vitro analysis of human glioma-associated macrophages", J Neurosurg., 110(3):572-82 (2009).
Perrault, et al., "Mediating Tumor Targeting Efficiency of Nanoparticles Through Design", Nano Lttrs, 9(5):1909-15 (2009).
Recinos, et al., "Combination of Intracranial Temozolomide With Intracranial Carmustine Improves Survival When Compared With Either Treatment Alone in a Rodent Glioma Model", Neurosurgery, 66:530-7 (2010).
Rippe, et al., "Effects of glomerular filtration rate on Ficoll sieving coefficients (theta) in rats", Kidney Intl, 69:1326-32 (2006).
Rittierodt, et al., "Repetitive doxorubicin treatment of glioblastoma enhances the PGP expression—a special role for endothelial cells", Exp Toxic Pathol., 55:39-44 (2003).
Roggendorf, et al., "Distribution and characterization of microglia/ macrophages in human brain tumors", Acta Neuropathol, 92:288-93 (1996).
Sadekar, et al., "Comparative Biodistribution of Pamam Dendrimers and HPMA Copolymers in Ovarian Tumor-Bearing Mice", Biomacromolecules, 12(1):88-96 (2011).
Sarin, et al., "Physiologic upper limit of pore size in the blood-tumor barrier of malignant solid tumors", J Translational Medicine, 7(51):1-12 (2009).
Schädlich, et al., "Tumor Accumulation of NIR Fluorescent PEG-PLA Nanoparticles: Impact of Particle Size and Human Xenograft Tumor Model", ACS Nano, 5(11):8710-20 (2011).
Schwartzbaum, et al., "Epidemiology and molecular pathology of glioma", Nature Clin Practice Neurology, 2(9):494-503 (2006).
Siegal, et al., "Doxorubicin encapsulated in sterically stabilized liposomes for the treatment of brain tumor model: biodistribution and therapeutic efficacy", J Neurosurgery, 83:1029-37 (1995).

(56) References Cited

OTHER PUBLICATIONS

Siegal, "Which drug or drug delivery system can change clinical practice for brain tumor therapy", Neuro-Oncology, 15(6):656-69 (2013).
Suzuki, et al., "Regulation of cell migration and cytokine production by HGF-like protein (HLP)/macrophage stimulating protein (MSP) in primary microglia", Biomed Res., 29(2):77-84 (2008).
Tang, et al., "Synthesis and Biological Response of Size-Specific, Monodisperse Drug-Silica Nanoconjugates", ACS Nano, 6(5):3954-66 (2012).
Tang, et al., "Size-Dependent Tumor Penetration and in Vivo Efficacy of Monodisperse Drug-Silica Nanoconjugates", Mol Pharma., 10:883-92 (2013).
Tyler, et al., "A thermal gel depot for local delivery of paclitaxel to treat experimental brain tumors in rats", J Neurosurgery, 113:210-17 (2010).
Tzeng, et al., "Therapeutic nanomedicine for brain cancer", Therapeutic Delivery, 4(6):1-29 (2013).
Van Handel, et al., "Selective uptake of multi-walled carbon nanotubes by tumor macrophages in a murine glioma model", J Neuroimmunology, 208:3-9 (2009).
Venishetty, et al., "Increased brain uptake of docetaxel and ketoconazole loaded folate-grafted solid lipid nanoparticles", Nanomedicine. 9:111-21 (2013).
Wohlfart, et al., "Kinetics of transport of doxorubicin bound to nanoparticles across the blood-brain barrier", J Controlled Release, 154:103-7 (2011).
Wong, et al., "Multistage nanoparticle delivery system for deep penetration into tumor tissue", PNAS, 108(6):2426-31 (2011).
Wu, et al., "Oligo(ethylene glycol)-Based Thermosensitive Dendrimers and Their Tumor Accumulation and Penetration", J Am Chem Soc., 136:3145-55 (2014).
Yabroff, et al., "Patterns of care and survival for patients with glioblastoma multiforme diagnosed during 2006", Neuro-Oncology, 14(3):351-9 (2012).
Yoshii, et al., "Intercapillary Distance in the Proliferating Area of Human Glioma", Cancer Research, 48:2938-41 (1988).
Yu, et al., "Synthesis of Paclitaxel-Conjugated β-Cyclodextrin Polyrotaxane and Its Antitumor Activity", Angewandte Chemie Intl Ed., 52:7272-7 (2013).
Zhai, et al., "Microglia/Macrophages Promote Glioma Progression", Glia, 59(3):472-85 (2011).
Zhou, et al., "Highly penetrative, drug-loaded nanocarriers improve treatment of glioblastoma", PNAS, 110(29):11751-6 (2013).
Zhu, et al., "Systemic Delivery of Neutralizing Antibody Targeting CCL2 for Glioma Therapy", J Neurooncol, 104(1):83-92 (2011).
Zhu, et al., Targeting of Tumor-Associated Macrophages Made Possible by PEG-Sheddable, Mannose-Modified Nanoparticles, Mol Pharma., 10:3525-30 (2013).
Akinc, et al., "Exploring polyethylenimine-mediated DNA transfection and the proton sponge hypothesis", J Gene Med, . 7(5): 657-63 (2005).
Aslam, et al., "Antibacterial and antifungal activity of cicerfuran and related 2-arylbenz.ofurans and stilbenes", Microbiol Res., 164:191-5 (2009).
Baek, et al., "Sybthesis and protein binding properties of T-antigen containing glycoPAMAM dendrimers", Bioorganic Med Chem., 10(1):11-7 (2002).
Beloosesky, et al., "Maternal N-acetyl cys1ein suppress fetal inflammatory cytokine responses to material lipopolysaccharide", Am J Obstet Gynenol., 195:1053-7 (2006).
Bourne, et al., "Dendrimers, a new class of candidate topical microbicides with activity against herpes simplex virus infection", Antimicrobial Agents Chemotherapy, 44:2471-4 (2000).
Buhimschi, et al., "Protective effect of n-acetylcysteine against fetal death and preterm labor induced by matemal inflammation", Am K Obstet Gynecol., 188:203-8 (2003).

De Kozak , et al., "Tumor Necrosis Factor and Nitric Oxide Production by Resident Retinal Glial Cells From Rats Presenting Hereditary Retinal Degeneration," Ocul. Immunol. Infiamm. 5(2):85-94 (1997).
Di Biase, et al., "Free radical release in C6 glial cells enriched in hexacosanoic acid: implication for X-linked adrenoleukodystrophy pathogenesis", Neurochem. Int. 44:215-21 (2004).
Dilger and Baker, "Oral N-acetyl L-cysteine is a safe and effective precursor of cysteine", J. Anim. Sci., J9:1-26 (2007b).
Downs, et al., "Long-Term Safety of Repeated Blood-Brain Barrier Opening via Focused Ultrasound with Microbubbles in Non-Human Primates Performing a Cognitive Task", Plos One, 10(5):e0125911 (2015).
Esfand, et Al., "Poly(amidoamine) (PAMAM) dendrimers: from biomimicry to drug delivery and biomediCBI applications", Drug Discov Today, 6:427-36 (2001).
Ethier-Chiasson, et al., "Modulation of placental pro1ein expression of OLR1: implication in pregnancy-related disorders", Reproduction, 136: 491-502 (2008).
Filipovska, et al., "Delivery of antisense peptide nucleic acids (PNAs) to the cytosol by disulphide conjugation to a lipophilic cation", FFBS Lett., 556:180-6 (2004).
Gonzalez, et al., "Glucocorticoids Antagonize AP-1 by Inhibiting the Activation/Phosphorylation of JNK Without Affecting Its Subcellular Distribution," J.Cell Biol. 150(5):1199-208 (2000).
Good, et al., "Lactobacillus rhamnosus HN001 decreases the severity of necrotizing enterocolitis in neonatal mice and preterm piglets: evidence in mice for a role of TLR9", Am J Physiol Gastrointest Liver Physiol., 306(11):G1021-32 (2014).
Higdon, et al., "Resveratrol," Linus Pauling Institute Micronutrient Information Center, http://lpi.oregonstate.edu/mic/dietary-factors/phytochemicals/resveratrol, accessed (Oct. 2015).
Jaffe , et al., "Safety and Pharmacokinetics of an Intraocular Fluocinolone Acetonide Sustained Delivery Device," Invest. Ophthalmol. & Vis. Sci. 41:3569-75 (2000).
Je and Kim., "Antimicrobial action of novel chitin deriva1ive", Biochim Biophys Acta, 1760:104-9 (2006a).
Kaminskas, et al., "The impact of molecular weight and PEG chain length on the systemic pharmacokinetics of PEGylated poly I-lysine dendrimers", Mol Pharm., 5(3): 449-63 (2008).
Khan, et al., "Administration of N-acetyl cys1eine after focal cerebral ischemia protects brain and reduces inflammation in a rat model of experimental sboke", J Neurosci Res.,4:519-27 (2004).
Khandare, et al., "Synthesis, cellular transport, and activity of polyamidoamine dendrimer-methylprednisolone conjugates", Bioconjugate Chem. 16:330-7 (2005b).
Kim and Wogan, "Mutagenesis of1he supF gene of pSP189 replicating in AD293 cells cocultivated with activated macrophages: roles of nitric oxide and reactive oxygen species", Chem. Res. Toxicol., 19:1483-91 (2006).
Kobayashi, et al., "Comparison of the Macromolecular MR Contrast Agents with Ethylenediamine-Core Versus Ammonia-Core Generation-6 Polyamidoamine Dendrimer", Bioconjugate Chem., 12:100-7 (2001c).
Kommareddy and Arniji, "Preparation and evaluation of thiol-modified gelatin nanoparticles for intracellular DNA delivery in response to glutathione", Bioconjugate Chem., 16:1423-32 (2005).
Lopez, et al., "Antibacterial activity and cyto1oxicity of PEGylated poly(amidoamine) dendrimers", Mol Biosyst., 5:1148-56 (2009).
Louwerse, et al., "Randomized, double-blind, controlled trial of acetylcysteine in amyotrophic lateral sclerosis", Arch. Neurol., 52:559-64 (1995).
Majoros, et al., "Poly(amidoannine) dendrimer-based multifunctional engineered nanodevice for cancer therapy", J Med Chem., 48(19):5892-9 (2005).
Malik, et al., "Dendrimers relationship between structure and biocompatibility in vitro and preliminary studies on the biodistributiom of 125l-labeled polyamidoamine dendrimers in vivo", J Control Release, 65:133-48 (2000).
Medline Plus, Blindness and vision loss, http://www.nlm.nih.gov/medlineplus/ency/article/003040.htm, accessed Jan. 23, 2013.

(56) References Cited

OTHER PUBLICATIONS

Noack, et al., "Nitrosative stress in primary gllal cultures after induction of the inducible isoform of nitric oxide synthase (i-NOS)", Toxicology, 148:133-42 (2000).
Pikkemaat, et al.,"Dendritic PARAS EST Contrast Agents for Magnetic Resonance Imaging", Contrast Media Mol. Imaging, 2:229-39 (2007).
Romero, et al., "Inflammation in pregnancy: its roles in reproductive physiology, obstetncal complications, and fetal injury", Nutr Rev., 65:5194-202 (2007a).
Roy, et al., "Oral gene delivery with chitosan-DNA nanoparticles gnerates immunologic protection in a murine model of peanut allergy", Nature Med., 5:387-91 (1999)., Free Radic Biol Med. ,45:686-99 (1999).
Rui, et al., "Displasmenylcholine-folate liposomes: an efficient vehicle for intracellular drug delivery", J Am Chem Soc., 120(44):11213-18 (1998).
Teo, et al., "Preventing acute gut wall damage in infectious diarrhoeas with glycosylated dendrimers", EMBO Mol Med., 4:866-81 (2012).
Tomalia, et al.,"Dendrimers as Multi-Purpose Nanodevices for Oncology Drug Delivery and Diagnostic Imaging", Biochemical Society Transactions, 35(1):61-7 (2007).
Ugvvumadu, "Role of antibiotic therapy for bacterial vaginosis and intermediate flora in pregnancy". Best Pactice Research, 21:391-402 (2007).
Wiwattanapatapee, et al., "Anionic PAMAM dendrimers rapidly cross adult rat intestine in vitro! a potential oral delivery system", Pharr». Res.,2:991-98 (2000).
Berger, et al., "Current and future pharmacological treatment strategies in x-linked adrenoleukodystrophy", Brain Pathol., 20(4):845-56 (2010).
Hossain, et al., "Comparative study of microtubuke inhibitors-Estramustine and natural podophyllotoxi conjugated PAMAM dendrimer on glioma cell proliferation", European Journal of Medicinal Chemistry, 68:47-57 (2013).
Jonas, et al., "Intravitreal triamcinolone acetonide for exudative age related macular degeneration", Br J Ophthalmol., 87(4):462-8 (2003).
Leukodystropy, National Organization for Rare Disorders, pp. 1-20, https://rarediseases.org/rare-diseases/leukodystrophy/, retrieved from the internet Sep. 5, 2017.
Lintas, et al., "Genome-wide expression studies in autism spectrum disorder, rett syndrome, and down syndrome", Neurobiol. Disease, 45:57-68 (2012).
Madaan, et al., "Dendrimers in drug delivery and targeting: Drug-dendrimer interactions and toxicity issues ", Journal of pharmacy & bioallied sciences, 6.3: 139 (2014).
Nance, et al., "Systemic dendrimer-drug treatment of ischemia-induced neonatal white matter injury", Journal of Controlled Release, 214:112-120 (2015).
Polam, "Effect of Chorioamnionitis on Neurodevelopmental Outcome in Preterm Infants", Arch Pediatrics Adolesc. Med., 159(11):1004-1085 (2005).
Resident, "Injection Methods", Standard Clinical Technique, 2(6): 128-129 (2009). (Japanese Language Document with English Summary).
Bi, et al., "Synthesis of PAMAM dendrimer-based fast cross-linking hydrogel for biofabrication", Journal of Biomaterials Science, 26(11):669-682 (2015).
Bravo-Osuna, et al., "Interfacial Interaction between Transmembrane Ocular Mucins and Adhesive Polymers and Dendrimers Analyzed by surface Plasmon Resonance", Pharmaceutical Research, 29(8):2329-2340 (2012).
Grinstaff, et al., "Dendritic macromers for hydrogel formation: Tailored materials for ophthalmic, orthopedic, and biotech applications", Journal of Polymer Science Part A: Polymer Chemistry, 46(2):383-400 (2007).
Kemp, et al., "Gene redundancy and pharmacological gene therapy: Implications for X-linked adrenoleukodystrophy", Nature America Inc., 4(11):1261-1268 (1998).
Oelker, et el., "Ophthalmic adhesives: a materials chemistry perspective", Journal of Materials Chemistry, 18(22):2521 (2008).
Seelbach, et al., "Multivalent dendrimers presenting spatially controlled clusters of binding epitopes in thermoresponsive hyaluronan hydrogels", Acta Biomaterialia, 10(10):4340-4350 (2014).
Vandamme, et al., Poly(amidoamine) dendrimers as ophthalmic vehicles for ocular delivery of pilocarpine nitrate and tropicamide, J. Control. Rel., 102:23-28 (2005).
Anonymous, "Poly(amidoamine)" Wikipedia, 1-11 (Mar. 27, 2018).
Bagul, et al., "Heterolayered hybrid dendrimers with optimized sugar head groups for enhancing carbohydrate-protein interactions", Polymer Chemistry, 8(35):5354-5366 (2017).
Han, et al., "Convergent Synthesis of PAMAM Dendrimers Containing Tetra (ethyleneoxide) at Core Using Click Chemistry", Bulletin of the Korean Chemical Society, 33(10):3501-3504 (2012).
Ribeiro-Viana et al., "BODIPY-Labeled DC-SIGN-Targeting Glycodendrons Efficiently Internalize and Route to Lysosomes in Human Dendritic Cells", Biomacromolecules, 13(10):3209-3219 (2012).
Sharma, et al., "A fast track strategy toward highly functionalized dendrimers with different structural layers: and 'onion peel approach'", Polymer Chemistry, 6(9):1436-1444 (2015).
Shiao, et al., "Synthesis of Dense and Chiral Dendritic Polyols Using Glyconanosynthon Scaffolds", Molecules Online, 21(4):448 (2016).

\* cited by examiner

SEQUENCE LISTING

```
<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Arg Gly Asp Cys
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: Cyclic Peptide
<220> FEATURE:
<221> NAME/KEY: MISC_FEATURE
<222> LOCATION: (4)..(4)
<223> OTHER INFORMATION: D enantiomer

<400> SEQUENCE: 2

Arg Gly Asp Phe Cys
1               5

<210> SEQ ID NO 3
<211> LENGTH: 5
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: MISC_FEATURE
<222> LOCATION: (1)..(5)
<223> OTHER INFORMATION: Cyclic Peptide
<220> FEATURE:
<221> NAME/KEY: MISC_FEATURE
<222> LOCATION: (4)..(4)
<223> OTHER INFORMATION: D enantiomer

<400> SEQUENCE: 3

Arg Gly Asp Tyr Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: Cyclic Peptide
<220> FEATURE:
<221> NAME/KEY: MISC_FEATURE
<222> LOCATION: (4)..(4)
<223> OTHER INFORMATION: D enantiomer

<400> SEQUENCE: 4

Arg Ala Asp Tyr Cys
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Tyr Glu Gln Asp Pro Trp Gly Val Lys Trp Trp Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 6

Trp Glu Asp Tyr Gln Trp Pro Val Tyr Lys Gly Trp
1               5                   10

<210> SEQ ID NO 7
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (17)..(30)
<223> OTHER INFORMATION: D enantiomer

<400> SEQUENCE: 7

Tyr Glu Gln Asp Pro Trp Gly Val Lys Trp Trp Tyr Gly Gly Gly Ser
1               5                   10                  15
```

```
Lys Leu Ala Lys Leu Ala Lys Lys Leu Ala Lys Leu Ala Lys
                20              25              30

<210> SEQ ID NO 8
<211> LENGTH: 31
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (18)..(31)
<223> OTHER INFORMATION: D enantiomer

<400> SEQUENCE: 8

Trp Glu Asp Tyr Gln Trp Pro Val Tyr Lys Gly Trp Ser Gly Gly Gly
1               5                   10                  15

Ser Lys Leu Ala Lys Leu Ala Lys Lys Leu Ala Lys Leu Ala Lys
                20              25              30

<210> SEQ ID NO 9
<211> LENGTH: 14
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(14)
<223> OTHER INFORMATION: D enantiomer

<400> SEQUENCE: 9

Lys Leu Ala Lys Leu Ala Lys Lys Leu Ala Lys Leu Ala Lys
1               5                   10
```

SELECTIVE DENDRIMER DELIVERY TO BRAIN TUMORS

CROSS REFERENCE TO RELATED APPLICATIONS

This application is a 371 application of International Application No. PCT/US2015/045104 filed Aug. 13, 2015, which claims priority to and benefit of U.S. Provisional Application Nos. 62/036,675 filed Aug. 13, 2014, 62/036,839, filed Aug. 13, 2014, and 62/059,240 filed Oct. 3, 2014, the disclosures of which are hereby incorporated herein by reference in their entirety.

The Sequence Listing submitted as a text file named "JHU_C_13214_PCT_substitute_ST25.txt," created on Mar. 12, 2018, and having a size of 3,192 bytes is hereby incorporated by reference pursuant to 37 C.F.R. § 1.52(e)(5).

FIELD OF THE INVENTION

The present invention is generally in the field of delivery of chemotherapeutic, immunotherapeutic and palliative drugs to the brain for treatment of brain tumors and associated symptoms.

BACKGROUND OF THE INVENTION

A brain tumor is an abnormal growth of tissue in the brain or central spine that can disrupt proper brain function. Doctors refer to a tumor based on where the tumor cells originated, and whether they are cancerous (malignant) or not (benign). The least aggressive type of brain tumor is often called a benign brain tumor. They originate from cells within or surrounding the brain, do not contain cancer cells, grow slowly, and typically have clear borders that do not spread into other tissue. Malignant brain tumors contain cancer cells and often do not have clear borders. They are considered to be life threatening because they grow rapidly and invade surrounding brain tissue. Tumors that start in cells of the brain are called primary brain tumors. Primary brain tumors may spread to other parts of the brain or to the spine, but rarely to other organs. Metastatic or secondary brain tumors begin in another part of the body and then spread to the brain. These tumors are more common than primary brain tumors and are named by the location in which they begin.

There are over 120 types of brain and central nervous system tumors. Brain and spinal cord tumors are different for everyone. They than in different areas, develop from different cell types, and may have different treatment options. Often, low-grade tumors (grade I and II), which are not aggressive, are treated with watchful monitoring or surgery alone. Though all tumors are monitored with repeat scans, grade II tumors are watched more closely after surgery and over time to make sure there is no recurrence. Higher grade tumors (grade III and IV), which are malignant and can grow quickly, are more difficult to remove and require additional treatments beyond surgery, such as radiation or chemotherapy. Microscopic tumor cells can remain after surgery and will eventually grow back. All treatments, therefore, are intended to prolong and improve life for as long as possible.

For a low-grade brain tumor, surgery may be the only treatment needed especially if all of the tumor can be removed. If there is visible tumor remaining after surgery, radiation and chemotherapy may be used. For higher-grade tumors, treatment usually begins with surgery, followed by radiation therapy and chemotherapy. Additional treatment options for high-grade tumors include X-rays and other forms of radiation to destroy tumor cells or delay tumor growth; chemotherapy to kill rapidly dividing cells; targeted therapy which focuses on a specific element of a cell, such as molecules or pathways required for cell growth, in order to use them as a target; and locally or regionally delivered treatment that produces electric fields to disrupt the rapid cell division exhibited by cancer cells by creating alternating, "wave-like" electric fields that travel across their region of usage in different directions.

Successfully treating brain tumors can be challenging. The body's blood-brain barrier normally protects the brain and spinal cord from harmful chemicals entering those structures through the bloodstream. However, this barrier also keeps out many types of chemotherapy. Surgery can be difficult if the tumor is near a delicate part of the brain or spinal cord. Even when the surgeon can completely remove the original tumor, there may be parts of the tumor remaining that are too small to be seen or removed during surgery. Radiation therapy can damage healthy tissue.

A brain tumor and its treatment often cause side effects. In addition to treatment to slow, stop, or eliminate the tumor, an important part of care is relieving a person's symptoms and side effects. This approach is called palliative or supportive care, and it includes supporting the patient with his or her physical, emotional, and social needs. Pain medication to help manage the pain from headaches, a common symptom of a brain tumor. Often, corticosteroids are used to lower swelling in the brain, which can lessen pain from the swelling without the need for prescription pain medications. Antiseizure medication is used to help control seizures.

Surgery is commonly used to remove all or part of brain tumors. Sometimes, surgery cannot be performed because the tumor is located in a place the surgeon cannot reach or is near a vital structure; these tumors are called inoperable.

The goal of chemotherapy can be to destroy cancer cells remaining after surgery, slow a tumor's growth, or reduce symptoms. A chemotherapy regimen usually consists of a specific number of cycles given over a set period of time. A patient may receive one drug at a time or combinations of different drugs at the same time. Common ways to give chemotherapy include a pill or capsule that is swallowed (orally) or by intravenous (IV). Some drugs are better at going through the blood-brain barrier, and these drugs are often used for a brain tumor because of this ability. Gliadel wafers are one way to give the drug carmustine, which involves placing the wafers in the area where the tumor was removed during surgery. For people with glioblastoma, the latest standard of care is radiation therapy with daily low-dose temozolomide (Temodar), followed by monthly doses of temozolomide after radiation therapy for six months to one year. A combination of three drugs, lomustine (CeeNU), procarbazine (Matulane), and vincristine (Vincasar) have been used along with radiation therapy. This approach has helped lengthen the lives of patients with grade III oligodendroglioma with a 1p19q co-deletion when given either before or right after radiation therapy. It has also been shown to lengthen lives of patients when given after radiation therapy for low-grade tumors that could not be completely removed with surgery. The side effects of chemotherapy depend on the individual and the dose used, but they can include fatigue, risk of infection, nausea and vomiting, hair loss, loss of appetite and diarrhea. These side effects usually go away once treatment is finished. Rarely, certain drugs may cause some hearing loss. Others may cause kidney damage. Patients may be given extra fluid by IV to protect their kidneys. A complete list of cancer drugs can be found on the NCI website.

Anti-angiogenesis is focused on stopping angiogenesis, which is the process of making new blood vessels. Because a tumor needs the nutrients delivered by blood vessels to grow and spread, the goal of anti-angiogenesis therapies is to "starve" the tumor. Bevacizumab (Avastin®) is an anti-angiogenesis therapy used to treat glioblastoma multiform when prior treatment has not worked.

A remission is when the tumor cannot be detected in the body. A remission can be temporary or permanent. For most primary brain tumors, despite imaging tests showing that the tumor growth is controlled or there are no visible signs of a tumor, it is common for a brain tumor to recur.

In glioma, tumor associated microglia/macrophages (TAM) have been shown to participate in tumor growth, tumor invasion, angiogenesis and immune system evasion. TAM is subjected to reprogramming in the tumor microenvironment, leading to an alternate immunosuppressive tumorigenic M2 phenotype. (da Fonseca A C, Badie B. Clin Dev Immunol 2013:264124). A variety of microglia/macrophage modulating molecules has been shown to switch the phenotype of TAMs and decrease glioma progression and increase survival in preclinical studies (El Andaloussi A, et, al. Glia 2006; 54:526-35; Hussain S F, et, al. Cancer Res 2007; 67:9630-6; Gabrusiewicz K, et, al. PLoS One 2011; 6:e23902; Markovic D S, et, al. Brain Behav Immun 2011; 25:624-8). Target delivery of immunomodulatory molecules to TAMs may provide improved efficacy with reduced side effects.

Malignant glioma is the most common and most aggressive primary brain tumor and despite the advances in treatment, the median survival remains at 16.4 months. Key challenges faced in the development of effective therapies relate to (a) the ability of systemically delivered chemotherapeutic agents to penetrate the impaired blood brain tumor barrier (BBTB) and provide homogenous coverage across the entire solid tumor and (b) the ability to target specific cells. Although small molecule-based therapeutics can effectively distribute within the tumor tissue, they are limited by rapid tumor clearance and off-target extravasation potentially leading to adverse effects. Recent advances in nanotechnology have provided selective tumor accumulation. However, the size of most nanoparticles limits extravasation and tumor penetration, thus limiting homogeneous solid tumor coverage. Careful tuning of particle size and surface charge has been attempted in order to enhance the nanoparticle distribution profile in subcutaneous tumors. Unfortunately, achieving homogeneous coverage of orthotopic brain tumors has proven even more challenging. This may be attributed to the lower permeability of the BBTB compared to the blood-tumor barrier (BTB) in a subcutaneous tumor, the heterogeneous intervascular spaces and the high interstitial pressure in brain tumors. Although, some strategies have attempted nanoparticle delivery through the BBTB via absorptive uptake; passive diffusion through the leaky BBTB fenestrations has only been demonstrated with molecules smaller than 20 nm and unhindered diffusion through the BBTB has been achieved with molecules of 7 nm, thus limiting systemic administration of most nanoparticle based therapeutics.

It is therefore an object of the present invention to provide an improved method and reagents for delivering drugs to treat brain tumors.

SUMMARY OF THE INVENTION

A composition comprising poly(amidoamine) (PAMAM) hydroxyl-terminated dendrimers covalently linked to or complexed with at least one therapeutic, prophylactic or diagnostic agent for the treatment or alleviation of one or more symptoms of a brain tumor have been developed. The composition contains one or more ethylene diamine-core poly(amidoamine) (PAMAM) hydroxyl-terminated generation-4, 5, 6, 7, 8, 9, or 10 (G4-10-OH) dendrimers. The G6 dendrimers have demonstrated unexpectedly high uptake, and uniform distribution in to the entire brain tumor. The dendrimers provide a means for selective delivery through the blood brain barrier ("BBB") of chemotherapeutic, immunotherapeutic and palliative agents. The dendrimers also have the advantage that multiple therapeutic, prophylactic, and/or diagnostic agents can be delivered with the same dendrimers. In one embodiment, the dendrimers are complexed with or conjugated to two different classes of compounds, providing simultaneous delivery. The dendrimers may be administered alone by intravenous injection, or as part of a multi-prong therapy with radiation and/or surgery. In one embodiment, the dendrimers are covalently linked to at least one radiosensitizing agent, in an amount effective to suppress or inhibit the activity of DDX3 in the proliferative disease. In another embodiment, the dendrimers are covalently linked to at least one detectable moiety, in an amount effective to detect the tumor in the subject. In another embodiment, the dendrimer composition has multiple agents, such as a chemotherapeutic agent, immunotherapeutic agent, an anti-seizure agent, a steroid to decrease swelling, antibiotic, anti-antiogenic agent, and/or a diagnostic agent, complexed with or conjugated to the dendrimers.

The dendrimer composition is preferably administered systemically, most preferably via intravenous injection. The composition may be administered prior to or immediately after surgery, radiation, or both. The composition may be designed for treatment of specific types of tumors, such as gliomas, or through targeting tumors associated with microglia/macrophages (TAM).

The examples demonstrated that hydroxyl terminated PAMAM dendrimers demonstrate unique favorable pharmacokinetic characteristics in a glioblastoma tumor model following systemic administration. Dendrimers rapidly accumulate and are selectively retained in the tumor tissue. This is due at least in part to the small size and near neutral surface charge which allow homogeneous distribution of the dendrimer through the entire solid tumor. Dendrimers homogeneously distribute through the extracellular matrix reaching the entire tumor and peritumoral area. Dendrimers intrinsically target neuroinflammation and accumulate in the tumor associated microglia/macrophages (TAMs). Increasing the generation of dendrimers from 4 to 6 can significantly increase dendrimer accumulation in the tumor without affecting their homogeneous distribution and targeting of TAMs. The generation 4 and 6 hydroxyl terminated PAMAM dendrimers can leak through the blood brain tumor barrier and selectively accumulate in glioblastoma, not the peritumoral area, following systemic administration. However, the dendrimers also accumulate in the peritumoral area, thereby having an effect on the migrating front of glioblastoma. These dendrimers intrinsically target tumor associated microglia/macrophages and are retained in these cells over at least 48 hours. There is no significant accumulation of dendrimers in the contralateral hemisphere ('healthy') where the dendrimers remain in the blood vessel lumen.

Generation 4 (G4) dendrimers rapidly and selectively accumulate and are retained in the tumor tissue despite their rapid clearance from the circulation. Based on fluorescence quantification and high resolution fluorescence microscopy dendrimers accumulate over the first 8 hours and are still retained in the tumor at 48 hours. Increasing the generation of dendrimers from 4 to 6 can significantly increase dendrimer accumulation, AUC and retention in the tumor ~100-fold without affecting their homogeneous distribution and targeting of TAMs.

BRIEF DESCRIPTION OF THE DRAWINGS

FIG. 1A is a graph of D-Cy5 concentration in brain areas 15 minutes, 1 hour, 4 hours, 8 hours, 24 hours and 48 hours following systemic administration. The accumulation is expressed as µg of D-Cy5 per g of tissue. FIG. 1B is a graph of the area under the curve ("AUC") of D-Cy5. The AUC at 48 hours demonstrates the significant difference in dendrimer exposure between the tumor and the contralateral hemisphere.

FIG. 4A is a graph of the image based cell count of the Iba1+ microglia/macrophages population per mm² area in the tumor, ipsilateral hemisphere and contralateral hemisphere. FIG. 4B is a graph of the image based measurement of microglia cell surface to volume ratio as an indication of activation and phagocytic activity of microglia/macrophages in healthy brain, contralateral hemisphere and ipsilateral hemisphere of a tumor inoculated brain and tumor tissue. 1+ cells D-Cy5 co-localization with Iba1+ TAMs and D-Cy5 co-localization with DAPI+ cells. Results are expressed as percent of the total DAPI+ cell population. There is no statistical significance between microglia uptake and cell uptake. Statistical $*p<0.05$; $**p<0.001$ Statistical analysis is based on 3-5 different slices.

FIG. 6A is the biodistribution is expressed in percent of injected dose per organ: D-Cy5 accumulation in kidney, urine and other organs. FIG. 6B is a graph of the time dependent concentration of D-Cy5 in spleen, liver, kidney and serum. Concentration is expressed in percent of injected dose per g of tissue. FIG. 6C is a graph of the fluorescence based quantification of the plasma pharmacokinetics of D-Cy5.

FIG. 8A shows that G6 dendrimers showed higher serum concentration and prolonged serum half-life than G4 dendrimers, which contributed to the higher tumor accumulation and targeting of G6 dendrimers. The dendrimer concentration was demonstrated as percentage of total injected dose per milliliter of serum. FIG. 8B showed that for G4 dendrimers, kidney had most dendrimer accumulation (20%-30%), significantly higher than dendrimer accumulation in liver and spleen (~0.3%) at different time points. For G6 dendrimers, the increase of size greatly decreased the renal filtration and kidney accumulation. The kidney concentration of G6 dendrimers was more than 10 fold less than G4 dendrimers (~1%), and started to show clearance from kidney starting from 48 hours. The liver accumulation of G6 dendrimers was similar to G4 dendrimers, while spleen showed ~5 fold higher accumulation, possibly due to the increased uptake by monocytes.

DETAILED DESCRIPTION OF THE INVENTION

I. Definitions

Figures 1A, 1B, 1C:
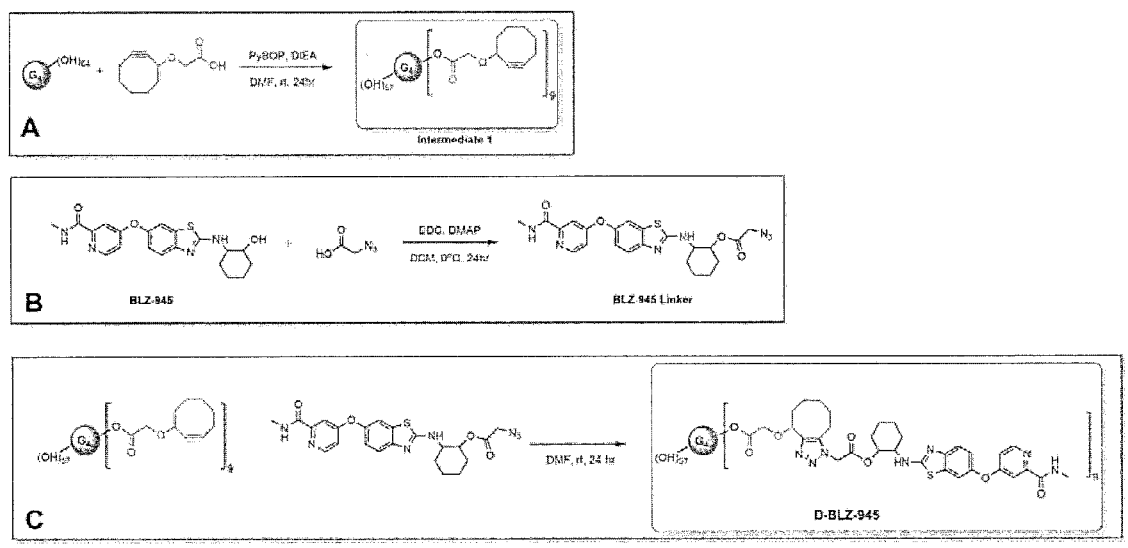
FIGS. 1A-1C show a synthetic scheme for conjugating a small molecule, BLZ-945, to a G4 hydroxyl-terminated dendrimer.

The term "therapeutic agent" refers to an agent that can be administered to prevent or treat one or more symptoms of a disease or disorder. Examples include, but are not limited to, a nucleic acid, a nucleic acid analog, a small molecule, a peptidomimetic, a protein, peptide, carbohydrate or sugar, lipid, or surfactant, or a combination thereof.

The term "treating" refers to preventing or alleviating one or more symptoms of a disease, disorder or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The phrase "therapeutically effective amount" refers to an amount of the therapeutic agent that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

II. Formulation

A. Dendrimers

The term "dendrimer" as used herein includes, but is not limited to, a molecular architecture with an interior core, interior layers (or "generations") of repeating units regularly attached to this initiator core, and an exterior surface of terminal groups attached to the outer most generation. Examples of dendrimers include, but are not limited to, PAMAM, polyester, polylysine, and PPI. The PAMAM dendrimers can have carboxylic, amine and hydroxyl terminations and can be any generation of dendrimers including, but not limited to, generation 1 PAMAM dendrimers, generation 2 PAMAM dendrimers, generation 3 PAMAM dendrimers, generation 4 PAMAM dendrimers, generation 5 PAMAM dendrimers, generation 6 PAMAM dendrimers, generation 7 PAMAM dendrimers, generation 8 PAMAM dendrimers, generation 9 PAMAM dendrimers, or generation 10 PAMAM dendrimers. Dendrimers suitable for use include, but are not limited to, polyamidoamine (PAMAM), polypropylamine (POPAM), polyethylenimine, polylysine, polyester, iptycene, aliphatic poly(ether), and/or aromatic polyether dendrimers. Each dendrimer of the dendrimer complex may be of similar or different chemical nature than the other dendrimers (e.g., the first dendrimer may include a PAMAM dendrimer, while the second dendrimer may comprise a POPAM dendrimer). In some embodiments, the first or second dendrimer may further include an additional agent. The multiarm PEG polymer includes a polyethylene glycol having at least two branches bearing sulfhydryl or thiopyridine terminal groups; however, embodiments disclosed herein are not limited to this class and PEG polymers bearing other terminal groups such as succinimidyl or maleimide terminations can be used. The PEG polymers in the molecular weight 10 kDa to 80 kDa can be used.

A dendrimer complex includes multiple dendrimers. For example, the dendrimer complex can include a third dendrimer; wherein the third-dendrimer is complexed with at least one other dendrimer. Further, a third agent can be complexed with the third dendrimer. In another embodiment, the first and second dendrimers are each complexed to a third dendrimer, wherein the first and second dendrimers are PAMAM dendrimers and the third dendrimer is a POPAM dendrimer. Additional dendrimers can be incorporated without departing from the spirit of the invention. When multiple dendrimers are utilized, multiple agents can also be incorporated. is not limited by the number of dendrimers complexed to one another.

As used herein, the term "PAMAM dendrimer" means poly(amidoamine) dendrimer, which may contain different cores, with amidoamine building blocks. The method for making them is known to those of skill in the art and generally, involves a two-step iterative reaction sequence that produces concentric shells (generations) of dendritic β-alanine units around a central initiator core. This PAMAM core-shell architecture grows linearly in diameter as a function of added shells (generations). Meanwhile, the surface groups amplify exponentially at each generation according to dendritic-branching mathematics. They are available in generations G0-10 with 5 different core types and 10 functional surface groups. The dendrimer-branched polymer may consist of polyamidoamine (PAMAM), polyester, polyether, polylysine, or polyethylene glycol (PEG), polypeptide dendrimers.

In accordance with some embodiments, the PAMAM dendrimers used can be generation 4 dendrimers, or more, with hydroxyl groups attached to their functional surface groups. The multiarm PEG polymer comprises polyethylene glycol having 2 and more branches bearing sulfhydryl or thiopyridine terminal groups; however, embodiments are not limited to this class and PEG polymers bearing other terminal groups such as succinimidyl or maleimide terminations can be used. The PEG polymers in the molecular weight 10 kDa to 80 kDa can be used.

In some embodiments, the dendrimers are in nanoparticle faun and are described in detail in international patent publication No. WO2009/046446.

Preparation of PAMAM-BLZ-945

As a non-limiting example, below is a synthetic scheme for conjugating a small molecule, BLZ-945, to a hydroxyl-terminated fourth generation PAMAM dendrimer (PAMAM-OH), using acetic acid, 2-(2-cyclooctyn-1-yloxy) acid and 2-azidoacetic acid as linkers. See FIGS. 1A-1C Initially, the hydroxyl-terminated fourth generation PAMAM dendrimer (PAMAM-OH) is functionalized into clickable bifunctional dendrimer (intermediate 1) with 9 clickable groups on the surface using 2-(2-cyclooctyn-1-yloxy) acid (FIG. 1A). BLZ-945 is reacted with 2-azido-acetic acid to form azide-functionalized intermediate via an ester bond (FIG. 1B). The resulting azide on the 2-azido-acetyl linker is further reacted with the clickable groups of the bifunctional dendrimer to get dendrimer-BLZ-945 conjugate. (FIG. 1C) There are approximately nine molecules of BLZ-945 conjugated to one molecule of the dendrimer.

The scheme described above is not limited to BLZ-945. Other small molecules, for example, a small molecule inhibitor of a Signal Transducer and Activator of Transcription (STAT) protein such as WP1066, and other small molecules such as minocycline and cyclosporine A can be conjugated to the dendrimers as immunomodulatory molecules for TAMs targeting therapies.

B. Coupling Agents and Spacers

Dendrimer complexes can be formed of therapeutically active agents or compounds (hereinafter "agent") conjugated or attached to a dendrimer or multiarm PEG. The attachment can occur via an appropriate spacer that provides a disulfide bridge between the agent and the dendrimer. The dendrimer complexes are capable of rapid release of the agent in vivo by thiol exchange reactions, under the reduced conditions found in body.

The term "spacers" as used herein is intended to include, compositions used for linking a therapeutically active agent to the dendrimer. The spacer can be either a single chemical entity or two or more chemical entities linked together to bridge the polymer and the therapeutic agent or imaging agent. The spacers can include any small chemical entity, peptide or polymers having sulfhydryl, thiopyridine, succinimidyl, maleimide, vinylsulfone, and carbonate terminations.

The spacer can be chosen from among a class of compounds terminating in sulfhydryl, thiopyridine, succinimidyl, maleimide, vinylsulfone and carbonate group. The spacer can comprise thiopyridine terminated compounds such as dithiodipyridine, N-Succinimidyl 3-(2-pyridyldithio)-propionate (SPDP), Succinimidyl 6-(3-[2-pyridyldithio]-propionamido)hexanoate LC-SPDP or Sulfo-LC-SPDP. The spacer can also include peptides wherein the peptides are linear or cyclic essentially having sulfhydryl groups such as glutathione, homocysteine, cysteine and its derivatives, arg-gly-asp-cys (RGDC) (SEQ ID NO:1), cyclo (Arg-Gly-Asp-d-Phe-Cys) (c(RGDfC)) (SEQ ID NO:2), cyclo(Arg-Gly-Asp-D-Tyr-Cys) (SEQ ID NO:3), cyclo (Arg-Ala-Asp-d-Tyr-Cys) (SEQ ID NO:4). The spacer can be a mercapto acid derivative such as 3 mercapto propionic acid, mercapto acetic acid, 4 mercapto butyric acid, thiolan-2-one, 6 mercaptohexanoic acid, 5 mercapto valeric acid and other mercapto derivatives such as 2 mercaptoethanol and 2 mercaptoethylamine. The spacer can be thiosalicylic acid and its derivatives, (4-succinimidyloxycarbonyl-methyl-alpha-2-pyridylthio)toluene, (3-[2-pyridithio]propionyl hydrazide. The spacer can have maleimide terminations wherein the spacer comprises polymer or small chemical entity such as bis-maleimido diethylene glycol and bis-maleimido triethylene glycol, Bis-Maleimidoethane, bismaleimidohexane. The spacer can comprise vinylsulfone such as 1,6-Hexane-bis-vinylsulfone. The spacer can comprise thioglycosides such as thioglucose. The spacer can be reduced proteins such as bovine serum albumin and human serum albumin, any thiol terminated compound capable of forming disulfide bonds. The spacer can include polyethylene glycol having maleimide, succinimidyl and thiol terminations.

The therapeutically active agent, imaging agent, and/or targeting moiety can be either covalently attached or intramolecularly dispersed or encapsulated. The dendrimer is preferably a PAMAM dendrimer up to generation 10, having carboxylic, hydroxyl, or amine terminations. The PEG polymer is a star shaped polymer having 2 or more arms and a molecular weight of 10 kDa to 80 kDa. The PEG polymer has sulfhydryl, thiopyridine, succinimidyl, or maleimide terminations. The dendrimer is linked to the targeting moiety, imaging agents, and/or therapeutic agents via a spacer ending in disulfide, ester or amide bonds.

C. Therapeutic, Prophylactic and Diagnostic Agents

The term "dendrimer complexes" as used herein refers to the dendrimer conjugated to or complexed with one or more therapeutic, prophylactic, or diagnostic agent. The dendrimer complex, when administered by i.v. injection, can preferentially cross the blood brain barrier (BBB) only under diseased condition and not under normal conditions. Preferably the agent(s) is attached or conjugated to PAMAM dendrimers or multiarm PEG, which are capable of preferentially releasing the drug intracellularly under the reduced conditions found in vivo. The dendrimer complexes linked to an agent can be used to perform several functions including targeting, localization at a diseased site, releasing the drug, and imaging purposes. The dendrimer complexes can be tagged with or without targeting moieties such that a disulfide bond between the dendrimer and the agent or imaging agent is formed via a spacer or linker molecule.

Representative therapeutic (including prodrugs), prophylactic or diagnostic agents can be peptides, proteins, carbohydrates, nucleotides or oligonucleotides, small molecules, or combinations thereof. Representative oligonucleotides include siRNAs, microRNAs, DNA, and RNA.

The term "chemotherapeutic agent" generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Examples of chemotherapeutic agents include alkylating agents, angiogenesis inhibitors, modulators of tumor immune response, aromatase inhibitors, antimetabolites, anthracyclines, antitumor antibiotics, platinum compounds, topoisomerase inhibitors, radioactive isotopes, radiosensitizing agents, checkpoint inhibitors, PD1 inhibitors, APRKinase inhibitors, plant alkaloids, glycolytic inhibitors and prodrugs thereof.

Representative chemotherapeutics commonly used in treating brain tumors include taxols such as paclitaxel, BCNU, camptothecin, doxycycline, cisplatin, and derivatives, analogues and prodrugs thereof.

Examples of PD-1 inhibitors include, for example, MDX-1106 is a genetically engineered, fully human immunoglobulin G4 (IgG4) monoclonal antibody specific for human PD-1, and pembrolizumab, recently approved by the US FDA.

Therapeutic agents can include agents which enhance the effect of a different therapy, such as radiation. As used herein, the term "a radiation dose sensitizer" means any agent, which when contacted with a cell, population of cell or tissue, increases the susceptibility of that cell, population of cell or tissue to ionizing radiation. In some embodiments, the radiosensitizer is a DDX3 inhibitor, such as the compound RK-33, or a salt, solvate, stereoisomer, or derivative thereof.

Therapeutic agents include agents which alleviate one or more symptoms of the brain tumor. For example, agents which reduce swelling associated with the tumor may be delivered via the dendrimers. Examples include anti-inflammatory agents such as steroids, for example, methyl prednisone, dexamethasone, and fluocinolone acetonide, nonsteroidal anti-inflammatory agents such as COX-2 inhibitors, gold compound anti-inflammatory agents, immunosuppressive agents, salicylate anti-inflammatory agents, ranibizumab, minocycline, and rapamycin. Other anti-inflammatory drugs include nonsteroidal drug such as indomethacin, aspirin, acetaminophen, diclofenac sodium and ibuprofen.

A peptide drug can be any sequence that is active on TAMs or cancer cells. Examples include Peptides (M2pep with the sequence YEQDPWGVKWWY (SEQ ID NO:5) and scM2pep with the sequence WEDYQWPVYKGW (SEQ ID NO:6)) with a Lys3Gly3Ser linker and a C-terminal biotin tag were purchased from Elim Biopharmaceuticals at >95% purity. KLA materials were synthesized and purified at >95% purity as follows: M2pepKLA (YEQDPWGVKWWYGGGS-D[KLAKLAK]$_2$ (SEQ ID NO:7)), scM2pepKLA (WEDYQWPVYKGWSGGGS-D[KLAKLAK]$_2$ (SEQ ID NO:8)), and KLA (D[KLAKLAK]$_2$ (SEQ ID NO:9)).

Examples for immunotherapeutic agents targeting TAMS can include colony stimulating factor-1 (CSF-1) receptor inhibitor such as BLZ-945 and PLX3397, MAPKinase inhibitors such as PD98059, a small molecule inhibitor of STAT (e.g. WP1066), Minocycline, and cyclosporine A.

Other exemplary therapeutic agents include vasodilators and anti-infective agents. Antibiotics include beta-lactams such as penicillin and ampicillin, cephalosporins such as cefuroxime, cefaclor, cephalexin, cephydroxil, cepfodoxime and proxetil, tetracycline antibiotics such as doxycycline and minocycline, microlide antibiotics such as azithromycin, erythromycin, rapamycin and clarithromycin, fluoroquinolones such as ciprofloxacin, enrofloxacin, ofloxacin, gatifloxacin, levofloxacin and norfloxacin, tobramycin, colistin, or aztreonam as well as antibiotics which are known to possess anti-inflammatory activity, such as erythromycin, azithromycin, or clarithromycin. Other agents having activity as anti-excitotoxic agents such as valproic acid, D-aminophosphonovalerate, D-aminophosphonoheptanoate, inhibitors of glutamate formation/release, such as baclofen, and NMDA receptor antagonists can also be administered.

In some embodiments, the molecules can include antibodies, for example, daclizumab, bevacizumab (AVASTIN®), ranibizumab (LUCENTIS®), basiliximab, ranibizumab, and pegaptanib sodium or peptides like SN50, and antagonists of NF.

Exemplary diagnostic agents include paramagnetic molecules, fluorescent compounds, magnetic molecules, and radionuclides, x-ray imaging agents, and contrast media. These may also be ligands or antibodies which are labelled with the foregoing or bind to labelled ligands or antibodies which are detectable by methods known to those skilled in the art.

Exemplary diagnostic agents include dyes, fluorescent dyes, Near infra-red dyes, SPECT imaging agents, PET imaging agents and radioisotopes. Representative dyes include carbocyanine, indocarbocyanine, oxacarbocyanine, thüicarbocyanine and merocyanine, polymethine, coumarine, rhodamine, xanthene, fluorescein, boron-dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

Representative SPECT or PET imaging agents include chelators such as di-ethylene tri-amine penta-acetic acid (DTPA), 1,4,7,10-tetra-azacyclododecane-1,4,7,10-tetraacetic acid (DOTA), di-amine dithiols, activated mercaptoacetyl-glycyl-glycyl-gylcine (MAG3), and hydrazidonicotinamide (HYNIC).

Representative isotopes include Tc-94m, Tc-99m, In-111, Ga-67, Ga-68, $Gd^{3+}$, Y-86, Y-90, Lu-177, Re-186, Re-188, Cu-64, Cu-67, Co-55, Co-57, F-18, Sc-47, Ac-225, Bi-213, Bi-212, Pb-212, Sm-153, Ho-166, and Dy-i66.

Targeting moieties include folic acid, RGD peptides either linear or cyclic, TAT peptides, LHRH and BH3.

D. Devices and Formulations

The dendrimers can be administered parenterally by subdural, intravenous, intra-amniotic, intraperitoneal, or subcutaneous routes.

The carriers or diluents used herein may be solid carriers or diluents for solid formulations, liquid carriers or diluents for liquid formulations, or mixtures thereof.

For liquid formulations, pharmaceutically acceptable carriers may be, for example, aqueous or non-aqueous solutions, suspensions, emulsions or oils. Parenteral vehicles (for subcutaneous, intravenous, intraarterial, or intratissue injection) include, for example, sodium chloride solution, Ringer's dextrose, dextrose and sodium chloride, lactated Ringer's and fixed oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

The dendrimers can also be administered in an emulsion, for example, water in oil. Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Formulations suitable for parenteral administration can include antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous vehicles can include fluid and nutrient replenishers, electrolyte replenishers such as those based on Ringer's dextrose. In general, water, saline, aqueous dextrose and related sugar solutions, and glycols such as propylene glycols or polyethylene glycol are preferred liquid carriers, particularly for injectable solutions.

Injectable pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Trissel, 15th ed., pages 622-630 (2009)).

Formulations for convection enhanced delivery ("CED") include solutions of low molecular weight sales and sugars such as mannitol.

III. Methods of Treatment

A. Disorders or Diseases to be Treated

The dendrimer complex composition, including dendrimers linked to one or more therapeutic, prophylactic and/or diagnostic agents, can selectively target microglia and astrocytes. Effective blood-brain tumor barrier (BBTB) penetration and uniform solid tumor distribution significantly enhance therapeutic delivery to brain tumors. Hydroxyl-functionalized, generation-4 or 6 poly(amidoamine) (PAMAM) dendrimers, with their small size, near neutral surface charge, selectively localize in cells associated with neuroinflammation.

As used herein, the term "proliferative disease" includes cancer and other diseases such as benign and malignant neoplasias and hyperplasias. The term cancer, includes cancers of the CNS and brain, including, but not limited to, gliomas, glioblastoma, gliosarcoma, astrocytoma, oligodendroglioma, ependymoma, meningioma, medulloblastoma, ganglioma, Schwannoma, craniopharyngioma, cordomas and pituitary tumors.

The tumors may also be of a different origin than the brain. For example, the tumors may have originated as alveolar rhabdomyosarcoma, bone cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The dendrimers are administered in a dosage dependent on the tumor size and type, location, and other treatments, as well as the agents to be delivered. Typically, an attending physician will decide the dosage of the composition with which to treat each individual subject, taking into consideration a variety of factors, such as age, body weight, general health, diet, sex, compound to be administered, route of administration, and the severity of the condition being treated. In general the timing and frequency of administration will be adjusted to balance the efficacy of a given treatment or diagnostic schedule with the side-effects of the given delivery system. Exemplary dosing frequencies include continuous infusion, single and multiple administrations such as hourly, daily, weekly, monthly or yearly dosing.

It will be understood by those of ordinary skill that a dosing regimen can be any amount and for any length of time sufficient to treat a brain tumor to reduce size, metastasis, or rate of growth, or to alleviate one or more symptoms such as swelling, pain, or seizures. Physicians routinely determine the length and amounts of therapy to be administered.

B. Adjunct or Combination Therapies

The dendrimer complexes can be administered in combination with one or more additional therapeutically active agents, which are known to be capable of treating brain tumors or the symptoms associated therewith.

For example, the dendrimers may be administered to the brain via intravenous administration or during surgery to remove all or a part of the tumor. The dendrimers may be used to deliver chemotherapeutic agents, immunotherapeutic agents, agents to enhance adjunct therapy such as of a subject undergoing radiation therapy, wherein the poly(amidoamine) (PAMAM) hydroxyl-terminated dendrimers are covalently linked to at least one radiosensitizing agent, in an amount effective to suppress or inhibit the activity of DDX3 in the proliferative disease in the brain.

It will be understood by those of ordinary skill in the art, that in addition to chemotherapy, surgical intervention and radiation therapy are also used in treatment of cancers of the CNS. Radiation therapy, as used herein, means administering ionizing radiation to the subject in proximity to the location of the cancer in the subject. In some embodiments, the radiosensitizing agent is administered in 2 or more doses and subsequently, ionizing radiation is administered to the subject in proximity to the location of the cancer in the subject. In further embodiments, the administration of the radiosensitizing agent followed by the ionizing radiation can be repeated for 2 or more cycles.

Typically, the dose of ionizing radiation varies with the size and location of the tumor, but is dose is in the range of 0.1 Gy to about 30 Gy, preferably in a range of 5 Gy to about 25 Gy.

In some embodiments, the ionizing radiation is in the form of sterotactic ablative radiotherapy (SABR) or sterotactic body radiation therapy (SBRT).

C. Imaging and Diagnostics

The dendrimers are also useful in a method for imaging TAM associated with a proliferative disease in a subject. The dendrimers are linked to at least one detectable moiety, administered to the subject intravenously in an amount effective to detect the TAM in the subject.

The dendrimer compositions can be formulated for theranostic purposes. In other words, the dendrimer compositions can comprise multiple compositions which include at least one biologically active agent and at least one detectable moiety. In some cases the at least one biologically active agent and at least one detectable moiety can be the same molecular entity. Thus, the dendrimer compositions can be used to detect the proliferative disease or tumor in the body of the subject and deliver a biologically active agent to the tumor or TAM simultaneously.

The present invention will be further understood by reference to the following non-limiting examples.

Example 1: Administration of Fluorescently Labeled Dendrimer to Gliomas in Rats

Materials and Methods.

The following agents were purchased: hydroxyl terminated ethylenediamino-core PAMAM dendrimer (referred to as dendrimer throughout, unless otherwise specified) (Dendritech, Midland, Mich.), Methanol (HPLC grade), DMF (HPLC grade), stainless steel beads (Fisher Scientific, Waltham, Mass.); and Cyanine 5 (Cy5) (GE Healthcare Life Science, Pittsburgh, Pa.). For confocal microscopy: nuclei counterstain, 4',6-diamidino-2-phenylindole, dihydrochloride (DAPI), Alexa Fluor® 594 Goat Anti-Rabbit IgG (H+L) Antibody (Molecular Probes, Eugene, Oreg.); Fluorescent mounting media (Dako, Santa Clara, Calif.); Anti-Iba1, Rabbit (Wako, Osaka, Japan); Lectin from *Bandeiraea simplicifolia* (BSI-B4) (Sigma-Aldrich, St. Louis, Mo.); Anti-GFAP 488 (eBioscience, San Diego, Calif.); Fluorescein isothiocyanate-dextran (FITC-dextran), average molecular weight 70,000 (Sigma Aldrich, St. Louis, Mo.).

Synthesis of Dendrimer Cy5 (D-Cy5) Conjugates

D-Cy5 was prepared through two steps following the method of *Mol Pharmaceutics*, 10:4560 (2013). Briefly, hydroxyl-terminated PAMAM dendrimer was surface-modified with amine groups to make a bifunctional dendrimer. 6-(Fmoc-amino)caproic acid was used to produce a Fmoc-protected bifunctional dendrimer intermediate that was eventually de-protected by re-dissolving in piperidine/DMF mixture. Cy5 dye with N-hydroxysuccinimide monoester was reacted with amine groups on the surface of bifunctional dendrimer. The 'crude' products were further extensively purified by dialysis. The final D-Cy5 conjugate was characterized using $^1$H NMR, high-performance liquid chromatography (HPLC) and gel permeation chromatography (GPC). The conjugate was stored as a solid powder at −20° C. and reconstituted at 10 mg/ml with sterile 0.9% NaCl on the day of administration.

Tumor Inoculation.

Female Fischer 344 rats, weighing 125-175 g each (Harlan Bioproducts, Indiana, Ind.), were housed in standard facilities and given free access to food and water. 9 L gliosarcoma intracranial implantation was performed as described in Neurosurgery 2010, 66, 530-7; J. Neurosurg. 2010, 113, 210-7. Briefly, the 9 L gliosarcoma (obtained from the Brain Tumor Research Center, UCSF, San Francisco, Calif.) was maintained in the flank of F344. Tumor was surgically excised from the flank of the carrier animal, sectioned into 1 mm$^3$ pieces and placed in sterile 0.9% NaCl on ice for intracranial implantation. Rats were anesthetized and a midline scalp incision was made to identify the sagittal and coronal sutures. A burr hole was made 3 mm lateral to the sagittal suture and 5 mm posterior to the coronal suture. The dura was incised, and using a surgical microscope and gentle suction a small cortical area was resected. A tumor piece was placed in the resection cavity and the skin was closed using surgical staples. All animals were treated in accordance with the policies and guidelines of the Johns Hopkins University Animal Care and Use Committee.

D-Cy5 Administration for Quantification and Immunofluorescence.

For tail vein injections, animals were immobilized and their tails were heated to induce vasodilation. 3 mg/300 μl of the dendrimer-Cy5 solution was administered per animal. For imaging of dendrimer and dextran distribution, 3 animals were co-injected with a 0.9% NaCl solution of 2 mg D-Cy5 and 2 mg dextran-FITC in 300 μl.

To study the dynamics of dendrimer accumulation in the tumor brain, D-Cy5 was injected into 27 tumor inoculated rats when the average tumor size was 6 mm in diameter and then animals were sacrificed at fixed time points (15 minutes, 1 hour, 4 hours, 8 hours, 24 hours, and 48 hours). Magnetic resonance imaging was used to measure intracranial tumor size. Blood was drawn through cardiac puncture and immediately centrifuged to collect plasma. Brains were harvested and flash frozen on dry ice for fluorescence spectroscopy based quantification or placed in 4% formalin solution for immunofluorescence.

To study the dendrimer cell uptake, D-Cy5 injection was performed in 3 tumor inoculated rats and 3 healthy rats, and animals were sacrificed 24 hours after the injection. Brains were harvested and placed in 4% formalin for immunofluorescence study.

To study the pharmacokinetics and biodistribution of dendrimer in plasma and systemic organs D-Cy5 was injected into 15 tumor-inoculated rats which were placed in metabolic cages for urine collection and animals were subsequently euthanized at fixed time points (15 minutes, 1 hour, 4 hours, 8 hours, 24 hours, and 48 hours). Organs were harvested and flash frozen on dry ice for fluorescence spectroscopy-based quantification or placed in 4% formalin for immunofluorescence.

Fluorescence Spectroscopy

Fluorescence-based quantification of D-Cy5 conjugates followed the protocol in Lesniak, Mol Pharm. 2013 Dec. 2; 10(12):4560-71. Briefly, 100-150 mg of frozen tissue was homogenized in 1 ml of methanol using a homogenizer (TissueLyser LT, Giagen) in 2 ml DNA LoBind Eppendorf tubes and subsequently sonicated. Suspensions were diluted to 100 mg/ml and centrifuged at 15,000 rpm for 15 minutes at 4° C. The resulting supernatants were subjected to fluorescence spectroscopy. Importantly, prior studies showed that D-Cy5 was stable in plasma, and could be recovered from the tissue intact, without appreciable release of the conjugated Cy5.

For the brain tissue, precise dissection of the tumor was performed and the peritumoral area was defined as up to 1 mm away from the tumor dissection plane. In the contralateral hemisphere 100 mg of the caudate/putamen with the surrounding white matter area was dissected and used for analysis. For plasma and urine samples a sample of 100 μl of plasma and urine was mixed with 900 μl of phosphate buffer (0.1M) and analyzed by fluorescence spectroscopy.

Fluorescence spectra of D-Cy5 conjugates and that obtained from tissue extracts were recorded using a Shimadzu RF-5301 Spectrofluorophotometer (Kyoto, Japan). D-Cy5 calibration curves were constructed, following every experiment, under different slit widths using the maximum emission wavelength of 662 nm after recording spectra from 650 nm to 720 nm with excitation wavelength of 645 nm. The D-Cy5 concentration was measured in methanol or phosphate buffer (0.1 M) in solutions ranging from 1 ng/ml to 100 μg/ml. The slit width was chosen based on the observed fluorescence level of different sample sets. For biological samples with low levels of D-Cy5 (i.e. brain, lung, heart), the excitation and emission slit width was set at 10; for biological samples with high levels of D-Cy5, (i.e. urine and kidney) excitation and emission slit width was set at 3. For the remaining biological samples, excitation slit width of 5 and emission slit width of 10 were used. All calibration curves exhibited linearity with $R^2$~0.99. Fluorescence registered from tissue of non D-Cy5 injected healthy and tumor inoculated rats was subtracted from the values observed from samples of D-Cy5 injected tissue in order to account for tissue autofluorescence.

Concentration of D-Cy5 conjugate in the brain was expressed in μg per g of tissue. The concentration of D-Cy5 conjugate in the other organs was expressed in percentage (%) of injected dose per g of tissue or % of injected dose per organ. Concentrations of the D-Cy5 conjugate in urine and blood were expressed in % of injected dose per ml or % of injected dose in total amount of urine or plasma. Total plasma concentration was calculated based on the weight of the animal (J. Nucl. Med., 1985, 26, 72-6). The brain and plasma quantification data were analyzed to calculate the area under the curve (AUC) and the brain to serum ratio.

The permeation constant ($K_{in}$) and the initial volume of distribution ($V_i$) were calculated in the brain tumor (Nanomedicine (Lond) 2013, 9, 111-21; J. Cereb. Blood Flow Metab. 1983, 3, 8-32). The brain to serum ratio and the area under the curve of the serum ($AUC_{(serum)}$(t) to serum concentration (Serum(t)) were calculated for each time point and linear regression analysis was performed in order to get the $K_{in}$ and $V_i$ based the following equation:

$$\frac{\text{Brain}(t)}{\text{Serum}(t)} = K_{in} \frac{AUC_{serum}(t)}{\text{Serum}(t)} + V_i$$

Figures 3A, 3B:
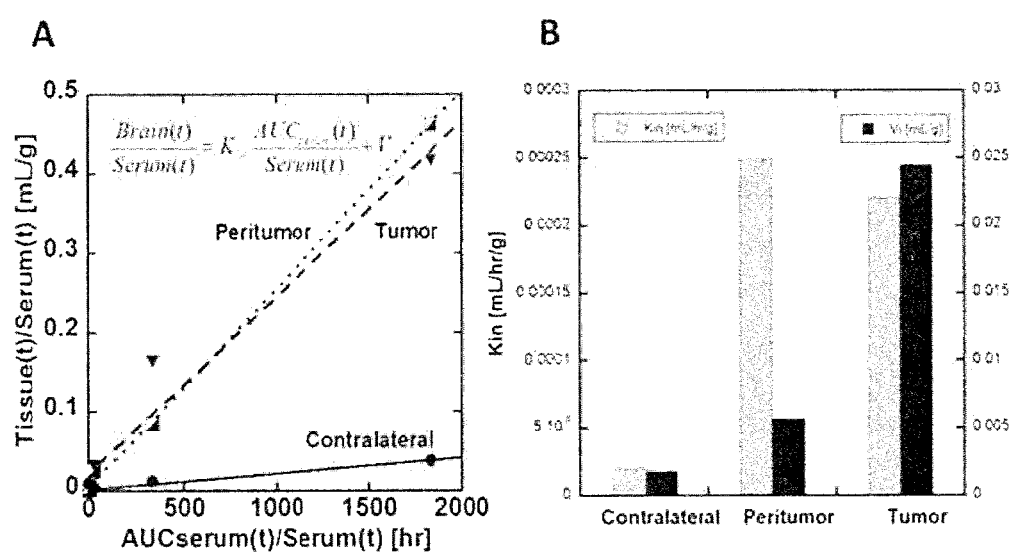
FIG. 3A is a graph of the linear curve fitting of brain quantification data. The $R^2$ for contralateral, peritumor and tumor are 0.98, 0.99 and 0.96 respectively.
FIG. 3B shows calculation of permeation constant (Kin) and initial volume of distribution (Vi) in tumor, peritumoral area and contralateral hemisphere based on brain pharmacokinetics data, Tissue (t)/serum (t) (mL/g) versus AUC serum t/Serum (t) (hr).

For all three regions in the brain, the multiple time-point regression analysis showed good linearity with $R^2$ equal to 0.98, 0.99, and 0.96 for the contralateral hemisphere, the peritumoral, and the tumor region, respectively (FIG. 3A).

Immunofluorescence

Freshly harvested tissues were fixed in 4% formalin for 24 hours, followed by a gradient of sucrose solutions before cryosection. Tissues were then sectioned transversely into 30 μm-thick slices using a Leica CM 1905 cryostat. Slices were stained with DAPI (nuclei), rabbit anti-Iba1 antibody for microglia/macrophages, and goat anti-rabbit 595 secondary antibody. Some slices were stained with isolectin for endothelial cell staining. Slices were then imaged using a confocal LSM 710 microscope (Carl Zeiss; Hertfordshire, UK) under 5×, 20×, 40× and 63× magnifications. For each slice of tumor-inoculated brains, images where acquired for the tumor, tumor border and contralateral hemisphere. For control (non-tumor) brains, 1-3 representative images were acquired. Settings were optimized to avoid background fluorescence based on non-injected control rat brains. Laser power, pinhole, gain, offset and digital gain were selected separately for each magnification and kept constant throughout the entire study.

Software

For image processing Zen software was used, any adjustments in brightness and contrast were kept constant throughout the same magnification images. No adjustments were done on the Cy5 channel. Imaris software was used for cell counting, co-localization and microglia surface to volume ratio measurements. Microsoft Excel 2010 and KaleidaGraph 4.0 were used for all calculations, curve fitting and figure plotting related to the pharmacokinetic study.

Cell Count and Co-Localization

For microglia/macrophage cell count 20× 13×13 tile scan images were analyzed and 3-5 slices were analyzed per region. The function 'spots' was used to identify Iba1+ microglia/macrophages. A diameter threshold of 4.15 μm was set to eliminate the objects smaller than microglia cells and an intensity threshold of 26.801 based on 'Quality' analysis was set to eliminate the background signal.

To study co-localization 40×, 4×4 tile scan images were used and 3-5 slides were analyzed per region. The function 'spots' was used to identify DAPI+ nuclei, Iba1+ microglia/macrophages and D-Cy5+ cells. For cells with D-Cy5 uptake, the spots with D-Cy5 and DAPI co-localization were counted; for microglia cells with D-Cy5 uptake, the spots with DAPI, anti-Iba1 and D-Cy5 co-localization were counted. Estimated diameters were applied to eliminate the spots with size smaller than cells, and signal thresholds were applied based on 'Quality' analysis. The function co-localize spots was used by counting the spots where D-Cy5 signal and cell signal are within 10 μm next to each other.

For surface to volume ratio analysis of the microglia cells, 3D representation of microglia morphology was acquired in confocal microscope using 40× magnification, with 3×3 tile scan, extending 10 μm in the z direction in z-stack. The function 'surfaces' was used and the individual Iba1+ microglia/macrophages were analyzed for surface and volume of each cell. Tumor area, ipsilateral (non-tumor area), contralateral area, and non-tumor brains were analyzed, approximately 150 cells were included for each region. The threshold settings were based on the diameter of cells (*Nat. Neurosci.* 2009, 12, 872-8).

Statistical Analysis

Statistical analysis of data was carried out by student's t-test and one-way ANOVA followed by Games-Howell tests with SPSS 18.0 (IBM, Inc.), as needed. Differences were considered statistically significant at $p<0.05$.

Results

Pharmacokinetics of Systemically Delivered D-Cy5 in Intracranial Brain Tumor

Figures 2A, 2B:
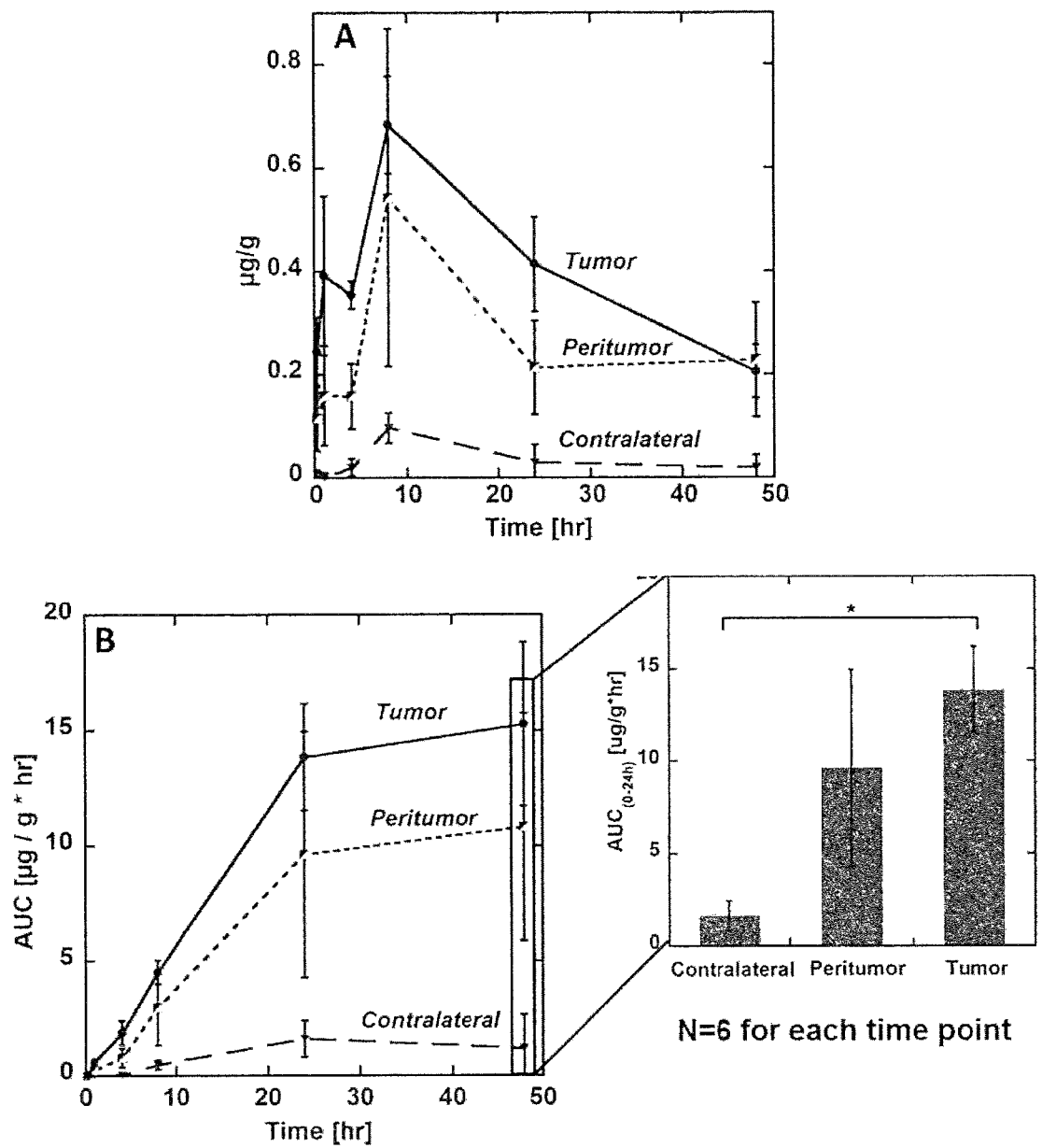
FIGS. 2A and 2B are graphs illustrating D-Cy5 pharmacokinetics in the brain (tumor, peritumoral area and contralateral hemisphere) of a rodent 9 L gliosarcoma model.

FIGS. 2A and 2B show the pharmacokinetic analysis of D-Cy5 in different regions of tumor bearing rodent brain: tumor, peritumor and contralateral hemisphere. The AUC at 48 hours was listed separately to demonstrate the large difference between tumor and contralateral hemisphere. Based on fluorescence confocal microscopy, dendrimers rapidly accumulated throughout a 5 mm tumor, as early as fifteen minutes after systemic administration.

In contrast, in the 'healthy' contralateral hemisphere, dendrimers outlined the blood vessels, and were not observed in the parenchyma using confocal microscopy images of tumor inoculated rodent brain following systemic administration of D-Cy5. Images indicate the homogeneous distribution of D-Cy5 in the tumor and the restriction of dendrimer in the blood vessel lumen. Fifteen minutes after systemic administration, the dendrimer was dispersed throughout the entire intracranial tumor parenchyma. This distribution was not influenced by the heterogeneity in the tumor parenchyma. There was no appreciable cellular uptake at this time point. At 4 hours post systemic dendrimer administration, the extracellular distribution in the tumor region had decreased, which was accompanied by an increased uptake by Iba1+ inflammatory cells. The contralateral hemisphere showed relatively minimal D-Cy5 fluorescence at all the time points.

In order to assess the kinetics of dendrimer accumulation in the brain, a recently developed fluorescence-based semi-quantification method for D-Cy5 was used. The use of the near IR Cy5 wavelength overcomes the tissue autofluorescence challenges. The high sensitivity of this method (0.1 ng/g of tissue) allowed detection of dendrimer accumulation at specific anatomic locations. In accordance with the confocal microscopy results, dendrimer rapidly accumulated in the tumor and peritumoral area, with a peak concentration occurring at 8 hours. See FIG. 3A. Dendrimer gradually cleared from the tumor at a rate of ~0.01 μg/g/hour, and from the peritumoral area at a rate of ~0.007 μg/g/hour, reaching a concentration of 0.2 μg/g of tissue, 48 hours after initial systemic injection. In the contralateral hemisphere, the dendrimer accumulation also peaked at 8 hours, at a concentration ~8-fold lower than that found in the tumor area. At 24 hours, traces of dendrimer (0.03 μg/g) could be detected in the contralateral hemisphere and a ~14 fold higher accumulation in the tumor was observed. At 48 hours the AUC was 10 times higher in the tumor area in comparison to the contralateral hemisphere, indicating significantly higher ($p<0.05$) overall exposure of the dendrimer to the tumor. The high and selective retention of dendrimer in the tumor and peritumoral area was visualized in a low magnification image of the tumor stained for astrocytes 24 hours following the administration of dendrimer.

The vasculature and the amount of BBTB disruption have been demonstrated to differ significantly between the tumor core and a tumor border which may play a significant role in drug accumulation. Therefore, blood vessel endothelial cells were stained in order to examine the difference in vasculature and, therefore, perfusion between the tumor and the peritumoral area. As expected, the peritumoral area and the tumor border showed dramatically denser vasculature than the tumor core. However, the dendrimer distribution appeared to be uniform in the tumor.

To further understand the kinetics of dendrimer penetration in the tumor the permeation constant ($K_{in}$) and the initial volume of distribution ($V_i$) in the tumor, peritumoral area and contralateral hemisphere, were calculated. See FIG. 3B. $K_{in}$ describes the influx of dendrimer from the blood to the brain, and was 10 fold higher in the tumor and peritumoral area comparison to the contralateral hemisphere, indicating the increased penetration of dendrimers and increased permeability and perfusion of the tumor tissue. $V_i$ represents the volume of the brain compartments in rapid equilibrium with plasma, differed significantly between the tumor and the peritumoral area indicating a larger volume of rapid equilibration in the tumor core. In tumor xenografts the hypoxic tumor core has increased vascular permeability in comparison to the tumor border and in glioblastoma specifically a distinct difference in the morphology of the BBTB between the tumor core and the peritumoral area has been shown, which may contribute to the rapid distribution in the tumor core as opposed to the peritumoral area.

Bio-Distribution of D-Cy5: Imaging-Based Study in Intracranial Brain Tumor

Figure 4A:
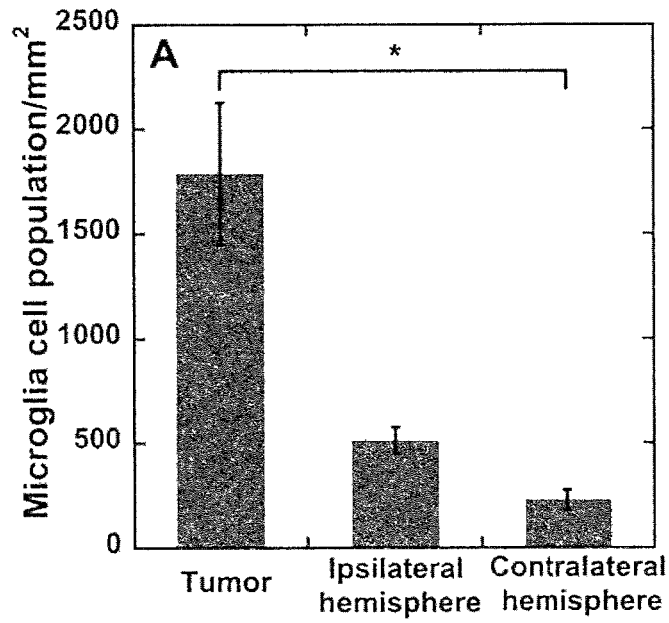
FIGS. 4A and 4B depict the characterization of microglia cells (population and activation) in a 9 L gliosarcoma inoculated rodent brain using Imaris software.
Figure 4B:
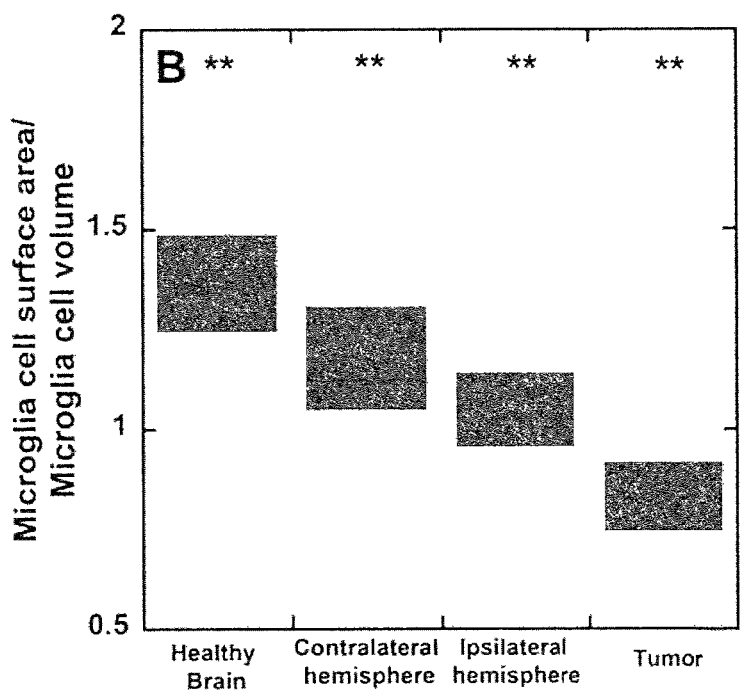

To study the dendrimer distribution in the tumor and peritumoral area, D-Cy5 was co-injected with linear dextran-FITC (70 kDa, ~6.5 nm radius) which has approximately twice the size of dendrimer. The tumor was clearly identified based on the increased density of DAPI-positive nuclei. See FIGS. 4A and 4B. At each time point, the dendrimer distributed homogeneously throughout the whole tumor region and a markedly decreased signal was observed 24 hours after injection. See FIG. 5. In comparison, signal from dextran-FITC was only observed around the tumor border and not in the tumor core, even when the laser power and gain settings were increased to see the background signal in the FITC channel. Higher magnification images showed that dendrimer rapidly distributed and delineated the extracellular matrix (ECM) leading to a reticular pattern of distribution and gradual accumulation in the cells. On the contrary, dextran showed limited distribution throughout the extracellular matrix but high signal could be seen within the blood vessel lumen fifteen minutes after injection. At later time points, limited amounts of dextran were retained in the tissue presumably due to low cellular uptake.

Characterization of Tumor Associated Microglia/Macrophages and Cell Uptake of Dendrimer Gliomas produce chemo-attractants and growth factors that promote recruitment and proliferation of microglia/macrophages. In human glioblastoma up to 30% of cells can be tumor associated macrophages. The microglial distribution was determined in different anatomic locations of the 9 L tumor model, which suggested that the concentration of TAM in this tumor model is similar to that seen in human glioblastoma. The microglia population per $mm^2$ was 9-fold higher within the tumor as compared to the contralateral hemisphere and 2.5-fold higher in healthy brain tissue of the ipsilateral hemisphere as compared to the contralateral TAM is reprogrammed in the tumor microenvironment, leading to an alternate immunosuppressive M2 phenotype. However, a number of studies have suggested sustained phagocytic activity of TAM in glioma. The phagocytic activity of TAM has been suggested to play a key role in nanoparticle uptake. When microglia/macrophages change from a resting to an activated form, their morphology is modified from ramified to amoeboid indicative of their increased phagocytic activity. In order to assess the morphology of TAM in the 9 L tumor model the surface to volume ratio of the immune cell population (Iba1+) in different anatomical locations was characterized. The surface to volume ratio (StoV ratio) is considered a 'measure' of microglial activation. The results indicate that the microglia/macrophages within the tumor and surrounding the tumor had a significantly ($p<0.001$) lower StoV ratio in comparison to the immune cells in the contralateral hemisphere, and in a healthy brain. The mean StoV ratio for tumor associated microglia was lower than 1, indicative of their amoeboid state and phagocytic activity. Image based cell count of the Iba1+ microglia/macrophages population per $mm^2$ area in the tumor, ipsilateral hemisphere and contralateral hemisphere. Image based measurement of microglia cell surface to volume ratio as an indication of activation and phagocytic activity of microglia/macrophages in healthy brain, contralateral hemisphere and ipsilateral hemisphere of a tumor inoculated brain and tumor tissue. 1+ cells D-Cy5 co-localization with Iba1+ TAMs and D-Cy5 co-localization with DAPI+ cells. Results are expressed as percent of the total DAPI+ cell population. There is no statistical significance between microglia uptake and cell uptake. Statistical *$p<0.05$; **$p<0.001$ Statistical analysis is based on 3-5 different slices. See FIGS. 4A and 4B.

Figure 5:
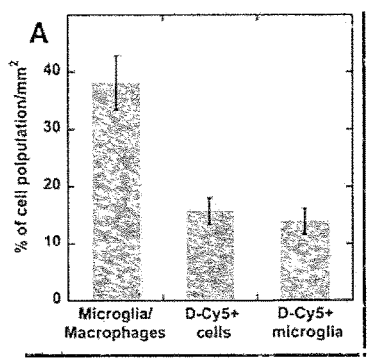
FIG. 5 is a graph of the D-Cy5 cell localization analysis 24 hours following administration using image based measurement of Iba-1+ cells D-Cy5 co-localization with Iba1+ TAMs and D-Cy5 co-localization with DAPI+ cells. Results are expressed as percent of the total DAPI+ cell population. There is no statistical significance between microglia uptake and cell uptake.

The localization of D-Cy5 in the Iba1+ microglia/macrophages cells was then calculated. At 24 hours post systemic administration, dendrimers localized in the Iba1+ TAM. Iba1+ microglia/macrophages were calculated to comprise 38% of the total tumor cell population (FIG. 5). Co-localization indicated that approximately half of the TAM population took up dendrimers and that the total population of dendrimer-positive cells did not differ quantitatively from the population of dendrimer-positive Iba1+ microglia/macrophages. Therefore, dendrimers were taken up almost exclusively by tumor associated macrophages within the tumor tissue, while other cells within the tumor region did not have measurable dendrimer uptake. In the tumor border (1 mm from the tumor edge based on DAPI stain) the dendrimer-positive microglia/macrophages were substantially reduced, reflecting the difference in the biological processes between the tumor core and the tumor border. Dendrimer was not present in the ipsilateral non-tumor region or in the contralateral hemisphere.

D-Cy5 cell localization analysis 24 hours following administration was performed using image based measurement of Iba-1+ cells D-Cy5 co-localization with Iba1+ TAMs and D-Cy5 co-localization with DAPI+ cells. Results are expressed as percent of the total DAPI+ cell population. There is no statistical significance between microglia uptake and cell uptake. High magnification (40×) fluorescence confocal imaging of different anatomic locations of a 9 L gliosarcoma inoculated brain.

Systemic Biodistribution of D-Cy5

After 24 hours systemic administration, fluorescence-quantification of extracted D-Cy5, suggested that 56% of the dendrimer was excreted through the urine, while 32% remained in the kidneys. This correlates well with the low serum levels (0.66%, FIG. 6A) at this same time point. After 24 hours systemic administration, only 2.5% of the dendrimers were accumulated in other major organs. 1.5% of these dendrimers were retained in the liver and spleen representing the elimination by the reticuloendothelial system (RES). Trace amounts accumulated in the brain, lung, and heart.

Figures 6A, 6B, 6C:
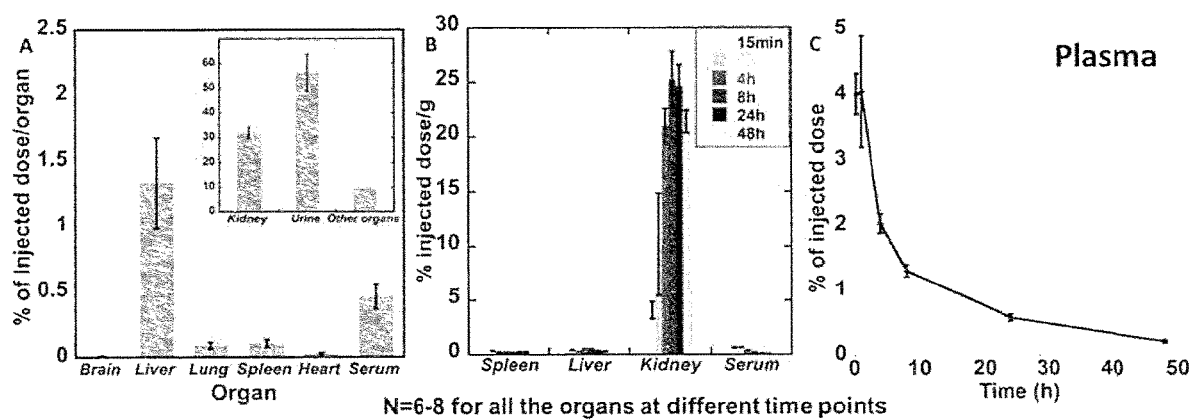
FIGS. 6A-6C are graphs based on the fluorescence based quantification of D-Cy5 in major organs (brain, liver, lung, spleen, heart, and kidney), serum and urine of 9 L gliosarcoma rodent model 24 hours following D-Cy5 administration.
Figures 8A, 8B:
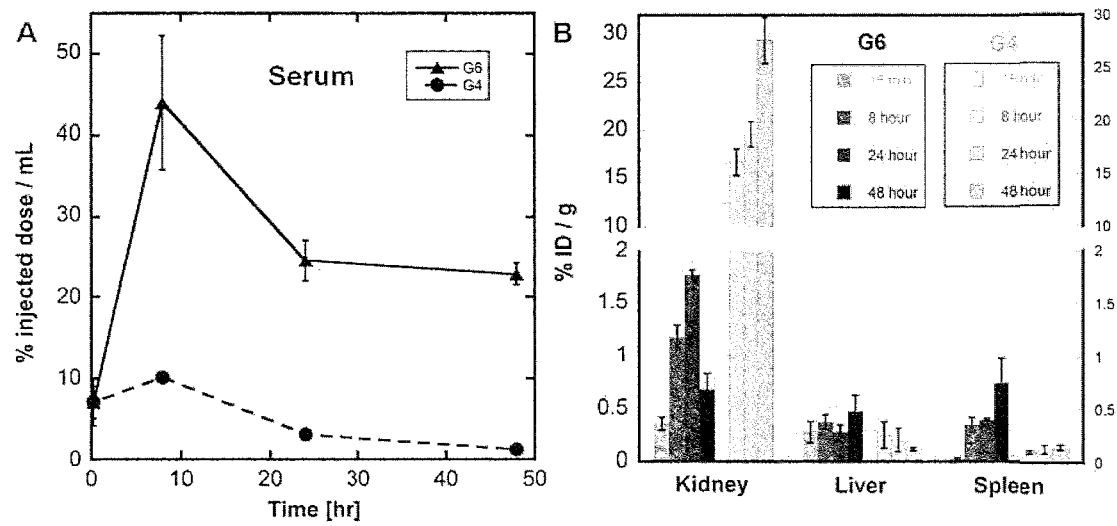
FIGS. 8A and 8B are graphs showing the G4 and G6 dendrimer concentration in serum and major organs: kidney, liver, spleen as a function of time.

To better understand the kinetics, dendrimer concentration in the serum and major organs was measured over time (FIG. 6B). The kidney had an increasing accumulation at all chosen time points up to 24 hours. After 48 hours from systemic administration, the amount of dendrimer in the kidneys began to decrease. Dendrimer serum level decreased rapidly with only 4% of the injected dose observed 15 minutes after systemic injection (FIG. 8A).

FIG. 6A shows the fluorescence based quantification of D-Cy5 in major organs (brain, liver, lung, spleen, heart, and kidney), serum and urine of 9 L gliosarcoma rodent model 24 hours following D-Cy5 administration. The biodistribution is expressed in percent of injected dose per organ; (inserted panel): D-Cy5 accumulation in kidney, urine and other organs. (6B) Time dependent concentration of D-Cy5 in spleen, liver, kidney and serum. Concentration is expressed in percent of injected dose per g of tissue. (57C) Fluorescence based quantification of the plasma pharmacokinetics of D-Cy5.

Renal Accumulation and Distribution

The high concentration of dendrimer in the renal system led to the study of the distribution in the kidney in order to assess the sites of accumulation. Based on fluorescence microscopy, the dendrimer accumulated in the renal cortex. Dendrimer co-localized with anti-GFAP antibody which stained the peritubular fibroblasts. No presence of dendrimer was observed in the glomeruli. There was no significant difference in terms of the clearance through the kidneys among healthy and tumor-bearing rats.

SUMMARY AND CONCLUSIONS

Malignant glioma is the most common primary brain tumor and results in more years of life lost than any other tumor. Numerous traditional small molecule chemotherapeutic drugs in preclinical and clinical trials fail to have a drastic impact in the natural history of the disease due to their low accumulation and rapid clearance from the tumor following systemic administration.

At 48 hours the dendrimer accumulation in the brain tumor is 11 fold higher than that in the contralateral hemisphere. This ratio stands out in comparison to other non-targeted nanoparticles and is comparable to actively targeted magnetic nanoparticles. Importantly, high retention is also observed in the peritumoral area. Glioblastoma cells are highly infiltrative and can be found in anatomic locations with intact blood brain barrier; thus achieving high retention at the peritumoral area is of distinct importance for the design of an effective therapeutic vehicle. Selective retention of dendrimers in the tumor and peritumoral area in combination with low circulation half-life allows for specific delivery of chemotherapeutics with limited off target effects.

Example 2: Hydroxyl Terminated Generation 6 PAMAM Dendrimers as Therapeutic Vehicles for the Treatment of Glioblastoma Materials and Methods The materials and methods are as described in Example 1, with the exception that both generation 4 and 6 hydroxyl terminated PAMAM dendrimers were utilized.

To study the dynamics of dendrimer accumulation in the tumor brain, dendrimers were injected into tumor inoculated rats when the average tumor size was 6 mm in diameter and then animals were sacrificed at different time points.

Results

The efficacy of chemotherapeutics is directly associated with the amount of accumulation in the tumor. Increasing the dendrimer size from generation 4 to generation 6 increased their hydrodynamic diameter from ~4.3 nm to ~6.7 nm without significantly influencing their ζ-potential (Table 1). Hydrodynamic diameter (size) and surface charge (ζ-potential) were measured using dynamic light scattering in PBS, pH 7.4 at room temperature. Molecular weight was provided by the supplier.

TABLE 1

Physiochemical properties of hydroxyl terminated dendrimers with generation 4 (G4-OH) and generation 6 (G6-OH). Dendrimer MW (kDa) Size + SEM (nm) ζ-potential + SEM (mV)

| | MW (kDa) | Size ± SEM (nm) | ζ-potential ± SEM (mV) |
|---|---|---|---|
| G4-OH | 14.1 | 4.3 ± 0.2 | +4.5 ± 0.1 |
| G6-OH | 58.0 | 6.7 ± 0.1 | 0.25 ± 0.4 |

Example 1 shows that G4 dendrimers selectively accumulate in TAMS when administered systemically in 9 L gliosarcoma inoculated rats at 24 hr post D-Cy5 administration. However, the increase of size allowed G6 dendrimers to avoid the rapid clearance caused by renal filtration and to circulate longer in the blood, allowing a better localization and retention. G6 dendrimers showed higher serum concentration and prolonged serum half-life than G4 dendrimers, which contributed to the higher tumor accumulation and targeting of G6 dendrimers.

Figures 7A, 7B, 7C:
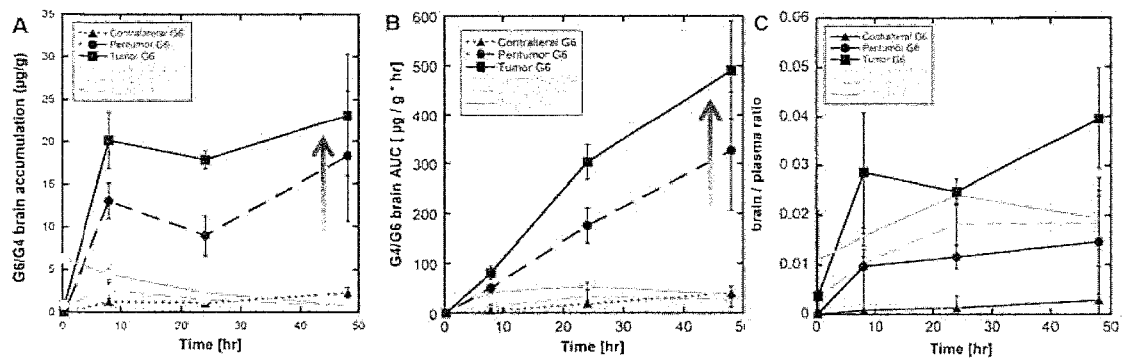
FIGS. 7A-7C are graphs of the comparison of accumulation (µg of dendrimer/g of brain tissue) (FIG. 7A) between G6 and G4 dendrimers in a tumor bearing brain as a function of time. The accumulation of G4 dendrimers in the tumor/peritumor peaked around 8 hours post injection, and gradually decreased, while G6 dendrimer concentration in tumor/peritumor continuously increased. At 48 hours, G6 concentration was almost 100 fold higher than G4 dendrimers concentration in the tumor; the area under curve (AUC) plot (FIG. 7B) which demonstrates G6 dendrimers have around 100 fold higher brain tumor exposure than G4 dendrimers within 48 hours. When the dendrimer concentration in the brain is normalized by the dendrimer concentration in the serum, the brain to serum ratio is an indication of the brain targeting ability. G6 dendrimers showed higher tumor targeting ability than G4 dendrimers at all the time points (FIG. 7C).

FIGS. 7A-7C are graphs of the comparison of accumulation (μg of dendrimer/g of brain tissue) (FIG. 7A) between G6 and G4 dendrimers in a tumor bearing brain as a function of time. The accumulation of G4 dendrimers in the tumor/peritumor peaked around 8 hours post injection, and gradually decreased, while G6 dendrimers concentration in tumor/peritumor continuously increased. At 48 hours, G6 concentration was almost 100-fold higher than G4 dendrimers concentration in the tumor; the area under curve (AUC) plot (FIG. 7B) which demonstrates G6 dendrimers have around 100 fold higher brain tumor exposure than G6 dendrimers within 48 hours.

When the dendrimer concentration in the brain is normalized by the dendrimer concentration in the serum, the brain to serum ratio is an indication of the brain targeting ability. G6 dendrimers showed higher tumor targeting ability than G4 dendrimers at all the time points (FIG. 6C). The dendrimer concentration was demonstrated as percentage of total injected dose per milliliter of serum. For G4 dendrimers, kidney had the most dendrimer accumulation (20%-30%), significantly higher than dendrimer accumulation in liver and spleen (~0.3%) at different time points. For G6 dendrimers, the increase of size greatly decreased the renal filtration and kidney accumulation. The kidney concentration of G6 dendrimers was more than 10 fold less than G4 dendrimers (~1%), and started to showed the evidence of clearance from kidney starting from 48 hours. The liver accumulation of G6 dendrimers was similar to G4 dendrimers, while spleen showed ~5 fold higher accumulation, possibly due to the increased uptake by monocytes). The high serum concentration provides a driving force for G6 dendrimers to diffuse across the blood-brain tumor barrier and better target tumor while accumulate in the tumor with 100-fold higher concentration and AUC (at 48 hours) compared with G4 dendrimers (FIG. 7B).

The high frequency of glioblastoma recurrence occurs from the individual cells that survive the aggressive treatment. For this reason it is important that any therapeutic vehicle be able to reach every tumor cell. Recent studies in the nanotechnology field have underlined that efficient distribution of nanoparticles throughout the tumor tissue as a prerequisite for efficacy. Most of these studies revealed that nanoparticles with a size range between 10-50 nm could uniformly distribute through the solid tumor, when administered into the tumor. Larger nanoparticles with size of sub-100 nm, are less likely to distribute homogeneously in the whole tumor bed, due to the fibrotic tissue, where no blood vessel exist, interweaving in between the nest of cancer cells forms diffusion barrier against the homogeneous distribution of molecules. However, the homogeneous distribution of nanoparticles also requires them to uniformly extravasate from vasculature without any hindrance. In the case of glioblastoma, this requirement further decreased the upper limit for size cutoff to 10 nm, considering the smaller fenestration and pore size in cranial tumors compared with subcutaneous tumor Unhindered diffusion through the BBTB has been achieved with molecules of 7 nm.

The charge density also influences the penetration of nanoparticles. It is important for nanoparticles to maintain neutral or slightly positive charge instead of strongly cationic to prevent the electrostatically derived binding-site barrier effect. As a result, G4 OH PAMAM dendrimers with hydrodynamic diameter of 4.3 nm and neutral surface charge can rapidly distribute through the intervascular spaces in 15 mins and homogeneously cover the entire 5 mm tumor. Increasing the generation to G6 not only retains the dendrimers' ability to homogeneously distribute in the brain tumor, but also prevents dendrimers from clear out from tumor parenchyma rapidly.

G4 and G6 dendrimers were co-injected intravenously into the tumor bearing rats through tail vein. The brain was fixed and cryo-sectioned axially. See FIGS. 8A and 8B. FIGS. 8A and 8B are graphs showing the G4 and G6 dendrimers concentration in serum and major organs: kidney, liver, spleen as a function of time. FIG. 8A shows that G6 dendrimers showed higher serum concentration and prolonged serum half-life than G4 dendrimers, which contributed to the higher tumor accumulation and targeting of G6 dendrimers. The dendrimer concentration was demonstrated as percentage of total injected dose per milliliter of serum. The liver accumulation of G6 dendrimers was similar to G4 dendrimers, while spleen showed ~5 fold higher accumulation, possibly due to the increased uptake by monocytes.

G4 dendrimers had a faster excretion rate than G6 dendrimers. FIG. 8B showed that for G4 dendrimers, kidney had most dendrimer accumulation (20%-30%), significantly higher than dendrimer accumulation in liver and spleen (~0.3%) at different time points. For G6 dendrimers, the increase of size greatly decreased the renal filtration and kidney accumulation. The kidney concentration of G6 dendrimers was more than 10 fold less than G4 dendrimers (~1%), and started to show clearance from kidney starting from 48 hours. For G4 dendrimer, excretion from the blood vessel to tumor tissue started immediately (~15 min) after i.v. injection, followed with clearance from tumor after 8 hours. After 24 hours post injection, G4 dendrimers were retained in the cells. For G6 dendrimers, the presence of dendrimers in the tumor tissue was not observed immediately after administration. The concentration of G6 dendrimers gradually increased in the whole observation period. At 48 hours post administration, G6 dendrimers showed the highest concentration in the tumor and peritumor area. Their homogeneous distribution in glioblastoma including the tumor cell migrating front and their retention in the tumor for at least 48 hours confirms the desirability if the dendrimers for efficient delivery of therapeutics.

In addition to homogeneous distribution across the tumor bed upon systemic administration, dendrimers can also accumulate in the peritumoral region, where deep, active perivasal and perineural invasion of glioma cells into normal nervous tissue occurs. Various techniques have been applied for the targeting of peritumoral region such as the using of GFAP specific monoclonal antibodies to modify the nanoparticles' surface property and the using of magnetic field to guide the accumulation of magnetic nanoparticles For dendrimers, without any modification or addition of targeting ligands, the area under curve (AUC) in peritumoral region reaches 60% of that in the tumor region, indicating the ability of dendrimers to intrinsically target peritumoral area.

Finally, dendrimers target neuroinflammatory cells and largely as well as exclusively localize in TAMs while resting ramified microglia in the non-tumor region do not take up dendrimers. Dendrimer specific accumulation in TAMs with low accumulation in the reticuloendothelial system and rapid clearance from the circulation provides a unique advantage for the delivery of antiglioma therapies targeting TAMs.

Modifications and variations of the methods and materials described herein will be apparent to those skilled in the art and are intended to be encompassed by the claims.

We claim:

1. A method of treating a brain tumor comprising systemically administering to a subject having a brain tumor a composition comprising
poly(amidoamine) (PAMAM) hydroxyl-terminated dendrimers selected from the group consisting of generation 4 generation 5, generation 6, generation 7, generation 8, generation 9, and generation 10 PAMAM dendrimers, covalently linked to or complexed with one or more modulators of tumor immune response,
wherein the dendrimers are not conjugated to targeting moieties,
wherein the hydrodynamic diameter of the dendrimers covalently linked to or complexed with the modulators is less than 10 nm, have a surface charge of about zero, and
wherein the composition is in a dosage effective to suppress or inhibit the growth of the brain tumor in the brain of the subject.

2. The method of claim 1, wherein the PAMAM dendrimer is a generation 6 PAMAM dendrimer.

3. The method of claim 1, wherein the one or more modulators of tumor immune response are selected from the group consisting of colony stimulating factor-1 (CSF-1) receptor inhibitors, MAPKinase inhibitors, inhibitors of STAT, and combinations thereof.

4. The method of claim 3, wherein the CSF-1 receptor inhibitor is selected from the group consisting of BLZ-945 and PLX3397.

5. The method of claim 3, wherein the MAPKinase inhibitor is PD98059.

6. The method of claim 3, wherein the inhibitor of STAT is WP1066.

7. The method of claim 1, wherein the modulators of tumor immune response are selected from the group consisting of YEQDPWGVKWWY (SEQ ID NO:5), WEDYQWPVYKGW (SEQ ID NO:6), YEQDPWGVKWWYGGGS-D[KLAKLAK]2 (SEQ ID NO:7), WEDYQWPVYKGWSGGGS-D[KLAKLAK]$_2$ (SEQ ID NO:8), D[KLAKLAK]$_2$ (SEQ ID NO:9), and combinations thereof.

8. The method of claim 1, wherein the dendrimers conjugated to modulators of tumor immune response are in an amount effective to reduce growth of the brain tumor.

9. The method of claim 1, wherein the one or more modulators of tumor immune response are selected from the group consisting of peptides, proteins, carbohydrates, nucleotides, oligonucleotides, and combinations thereof.

10. The method of claim 1, wherein the one or more modulators of tumor immune response are selected from the group consisting of anti-inflammatory agents, and immunosuppressive agents.

11. The method of claim 10, wherein the anti-inflammatory agents are selected from the group consisting of steroidal anti-inflammatories, non-steroidal anti-inflammatory agents, gold compound anti-inflammatory agents, immunosuppressive agents, salicylate anti-inflammatory agents, ranibizumab, minocycline, and rapamycin.

12. The method of claim 1, further comprising administering dendrimers having bound thereto diagnostic agents selected from the group consisting of paramagnetic molecules, fluorescent compounds, magnetic molecules, radionuclides, x-ray imaging agents, contrast media, fluorescent dyes, Near infra-red dyes, SPECT imaging agents, PET imaging agents, and radioisotopes.

13. The method of 12, wherein the diagnostic agent is a dye selected from the group consisting of carbocyanine, indocarbocyanine, oxacarbocyanine, thüicarbocyanine and merocyanine, polymethine, coumarine, rhodamine, xanthene, fluorescein, boron~dipyrromethane (BODIPY), Cy5, Cy5.5, Cy7, VivoTag-680, VivoTag-S680, VivoTag-S750, AlexaFluor660, AlexaFluor680, AlexaFluor700, AlexaFluor750, AlexaFluor790, Dy677, Dy676, Dy682, Dy752, Dy780, DyLight547, Dylight647, HiLyte Fluor 647, HiLyte Fluor 680, HiLyte Fluor 750, IRDye 800CW, IRDye 800RS, IRDye 700DX, ADS780WS, ADS830WS, and ADS832WS.

14. The method of claim 12, wherein the SPECT or PET imaging agent is a chelator selected from the group consisting of di-ethylene tri-amine penta-acetic acid (DTPA), 1,4,7,10-tetra-azacyclododecane-1,4,7,10-tetraacetic acid (DOTA), di-amine dithiols, activated mercaptoacetyl-glycyl-glycyl-gylcine (MAG3), and hydrazidonicotinamide (HYNIC).

15. The method of claim 12, wherein the radioisotopes are selected from the group consisting of Tc-94m, Tc-99m, In-111, Ga-67, Ga-68, Gd3+, Y-86, Y-90, Lu-177, Re-186, Re-188, Cu-64, Cu-67, Co-55, Co-57, F-18, Sc-47, Ac-225, Bi-213, Bi-212, Pb-212, Sm-153, Ho-166, and Dy-i66.

16. The method of claim 1, for treating a brain tumor in a subject undergoing radiation therapy further comprising administering to the subject dendrimers covalently linked to at least one radiosensitizing agent, in an amount effective to suppress or inhibit the activity of DDX3 in the tumor in the subject.

17. The method of claim 16, wherein the radiosensitizing agent is administered in two or more doses and then administering ionizing radiation to the subject in proximity to the location of the tumor in the subject, optionally repeating administration of the radiosensitizing agent followed by the ionizing radiation for 2 or more cycles.

18. The method of claim 16, wherein the ionizing radiation dose is between 0.1 Gy and 30 Gy.

19. The method of claim 16, wherein the radiation is stereotactic ablative radiotherapy (SABR) or sterotactic body radiation therapy (SBRT).

20. The method of claim 16, wherein the radiosensitizing agent is RX-33.

21. The method of claim 1, wherein the tumor originates as a cancer selected from the group consisting of alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer.

22. The method of claim 1, wherein the tumor is a brain cancer selected from the group consisting of neoplasias, hyperplasias and cancers of the central nervous system.

23. The method of claim 22, wherein the cancer is a glioma.

24. The method of claim 1, wherein the dendrimer composition is formulated with liposomes, particles, suspensions, solutions or emulsions.

25. The method of claim 1, wherein the composition is administered to the subject in a time period selected from the group consisting of daily, weekly, biweekly, monthly, and bimonthly.

26. A formulation for use in the method of claim 1 comprising poly(amidoamine) (PAMAM) hydroxyl-terminated dendrimers selected from the group consisting of generation 4 generation 5, generation 6, generation 7, generation 8, generation 9, and generation 10 PAMAM dendrimers, covalently linked to or complexed with one or more modulators of tumor immune response,
wherein the dendrimers are not conjugated to targeting moieties,
wherein the hydrodynamic diameter of the dendrimers covalently linked to or complexed with the modulators is less than 10 nm, have a surface charge of about zero,
the dendrimer conjugates targeting tumor-associated macrophages (TAMs),
wherein the formulation comprises the dendrimers in a dosage effective to suppress or inhibit the growth of the brain tumor in the brain of the subject.

27. The method of claim 1, wherein the dosage is in an amount effective to slow, stop, or eliminate the brain tumor with reduced side effects relative to treatment with the same modulators of tumor immune response administered without conjugation to a dendrimer.

28. The method of claim 1, wherein the cell surface to volume ratio of tumor associated microglia in the brain is lower than 1 compared to untreated control.

29. The method of claim 22 wherein the cancer is selected from the group consisting of gliomas, glioblastoma, astrocytoma, oligodendroglioma, ependymoma, meningioma, medulloblastoma, ganglioma, Schwannoma, craniopharyngioma, cordomas, and pituitary tumors.

* * * * *

UNITED STATES PATENT AND TRADEMARK OFFICE
CERTIFICATE OF CORRECTION

PATENT NO. : 10,918,720 B2
APPLICATION NO. : 15/502739
DATED : February 16, 2021
INVENTOR(S) : Rangaramanujam et al.

It is certified that error appears in the above-identified patent and that said Letters Patent is hereby corrected as shown below:

In the Claims

Claim 1, Column 27, Lines 42-43, replace "generation 4 generation 5" with --generation 4, generation 5--.
Claim 1, Column 27, Line 51, replace "have a surface charge" with --having a surface charge--.
Claim 26, Column 30, Line 26, replace "generation 4 generation 5" with --generation 4, generation 5--.
Claim 26, Column 30, Line 34, replace "have a surface charge" with --having a surface charge--.

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*